(12) United States Patent
van Deutekom

(10) Patent No.: US 9,499,818 B2
(45) Date of Patent: Nov. 22, 2016

(54) METHODS AND MEANS FOR EFFICIENT SKIPPING OF AT LEAST ONE OF THE EXONS 51-53, 55, 57 AND 59 OF THE HUMAN DUCHENNE MUSCULAR DYSTROPHY GENE

(71) Applicants: Academisch Ziekenhuis Leiden, Leiden (NL); Prosena Technologies B.V., Leiden (NL)

(72) Inventor: Judith Christina Theodora van Deutekom, Dordrecht (NL)

(73) Assignees: BioMarin Technologies, B.V., Leiden (NL); Academisch Ziekenhuis Leiden, Leiden (NL)

( * ) Notice: Subject to any disclaimer, the term of this patent is extended or adjusted under 35 U.S.C. 154(b) by 0 days.

(21) Appl. No.: 14/631,686

(22) Filed: Feb. 25, 2015

(65) Prior Publication Data

US 2015/0166996 A1     Jun. 18, 2015

Related U.S. Application Data

(63) Continuation of application No. 13/094,571, filed on Apr. 26, 2011, now abandoned, which is a continuation of application No. PCT/NL2009/050113, filed on Mar. 11, 2009, which is a continuation of application No. PCT/NL2008/050673, filed on Oct. 27, 2008.

(51) Int. Cl.
| | |
|---|---|
| *C07H 21/04* | (2006.01) |
| *C12N 15/113* | (2010.01) |
| *A61K 31/56* | (2006.01) |
| *A61K 31/57* | (2006.01) |
| *A61K 38/17* | (2006.01) |
| *A61K 45/06* | (2006.01) |
| *A61K 48/00* | (2006.01) |
| *A61K 31/7088* | (2006.01) |

(52) U.S. Cl.
CPC ............. *C12N 15/113* (2013.01); *A61K 31/56* (2013.01); *A61K 31/57* (2013.01); *A61K 38/1719* (2013.01); *A61K 45/06* (2013.01); *A61K 31/7088* (2013.01); *A61K 48/00* (2013.01); *C12N 2310/11* (2013.01); *C12N 2310/315* (2013.01); *C12N 2310/321* (2013.01); *C12N 2310/3233* (2013.01); *C12N 2320/33* (2013.01)

(58) Field of Classification Search
CPC .................................................. C12N 15/111
See application file for complete search history.

(56) References Cited

U.S. PATENT DOCUMENTS

| | | | |
|---|---|---|---|
| 5,034,506 A | 7/1991 | Summerton et al. | 528/391 |
| 5,418,139 A | 5/1995 | Campbell | 435/7.21 |
| 5,541,308 A | 7/1996 | Hogan et al. | 536/23.1 |
| 5,593,974 A | 1/1997 | Rosenberg et al. | 514/44 |
| 5,608,046 A | 3/1997 | Cook et al. | |
| 5,624,803 A | 4/1997 | Noonberg et al. | 435/6 |
| 5,627,263 A | 5/1997 | Ruoslahti et al. | 530/327 |
| 5,658,764 A | 8/1997 | Pergolizzi et al. | 435/91.2 |
| 5,741,645 A | 4/1998 | Orr et al. | 435/6 |
| 5,766,847 A | 6/1998 | Jäckle et al. | 435/6 |
| 5,853,995 A | 12/1998 | Lee | 435/6.12 |
| 5,869,252 A | 2/1999 | Bouma et al. | 435/6 |
| 5,916,808 A | 6/1999 | Kole et al. | 435/375 |
| 5,962,332 A | 10/1999 | Singer et al. | 436/94 |
| 5,968,909 A | 10/1999 | Agrawal et al. | 514/44 |
| 5,976,879 A | 11/1999 | Kole et al. | 435/375 |
| 6,124,100 A | 9/2000 | Jin | 435/6 |
| 6,130,207 A | 10/2000 | Dean et al. | 514/44 |
| 6,133,031 A | 10/2000 | Monia et al. | 435/375 |
| 6,165,786 A | 12/2000 | Bennett et al. | 435/366 |
| 6,172,208 B1 | 1/2001 | Cook | 536/23.1 |
| 6,172,216 B1 | 1/2001 | Bennett et al. | 536/24.5 |
| 6,210,892 B1 | 4/2001 | Bennett et al. | 435/6 |
| 6,251,589 B1 | 6/2001 | Tsuji et al. | 435/6 |
| 6,280,938 B1 | 8/2001 | Ranum et al. | 435/6 |
| 6,300,060 B1 | 10/2001 | Kantoff et al. | 435/6 |
| 6,322,978 B1 | 11/2001 | Kahn et al. | 435/6 |
| 6,329,501 B1 | 12/2001 | Smith et al. | 530/329 |
| 6,355,481 B1 | 3/2002 | Li et al. | 435/331 |
| 6,355,690 B1 | 3/2002 | Tsuji | 514/706 |
| 6,369,038 B1 | 4/2002 | Blumenfeld et al. | 514/44 |

(Continued)

FOREIGN PATENT DOCUMENTS

| | | | | |
|---|---|---|---|---|
| AU | WO 2006000057 A1 * | 1/2006 | | C12N 15/113 |
| CA | 2319149 | 10/2001 | | C07H 21/00 |
| CA | 2526893 | 11/2004 | | A61K 31/7088 |
| EP | 438512 A1 | 7/1991 | | C12Q 1/68 |
| EP | 558697 | 9/1993 | | A61K 48/00 |
| EP | 614977 A2 | 9/1994 | | C12N 15/12 |
| EP | 850300 | 7/1998 | | C12N 15/11 |
| EP | 1054058 | 5/2000 | | C12N 15/113 |
| EP | 1015628 A1 | 7/2000 | | C12Q 1/68 |
| EP | 1133993 | 9/2001 | | A61K 31/56 |

(Continued)

OTHER PUBLICATIONS

Sironi et al., "The dystrophin gene is alternatively spliced throughout its coding sequence," FEBS Letters 517, pp. 163-166, 2002.

(Continued)

*Primary Examiner* — Dana Shin

(74) *Attorney, Agent, or Firm* — Sunstein Kann Murphy & Timbers LLP

(57) ABSTRACT

The invention relates to a method where a molecule is used for inducing and/or promoting the skipping of at least one of the exons 51-53, 55, 57 and 59 of the DMD pre-mRNA in a patient, preferably in an isolated cell of a patient. The method comprising providing the cell and/or the patient with a molecule. The invention also relates to the molecule and its composition that is being used for inducing exon skipping.

17 Claims, 4 Drawing Sheets

(56) References Cited

U.S. PATENT DOCUMENTS

Figure 1:
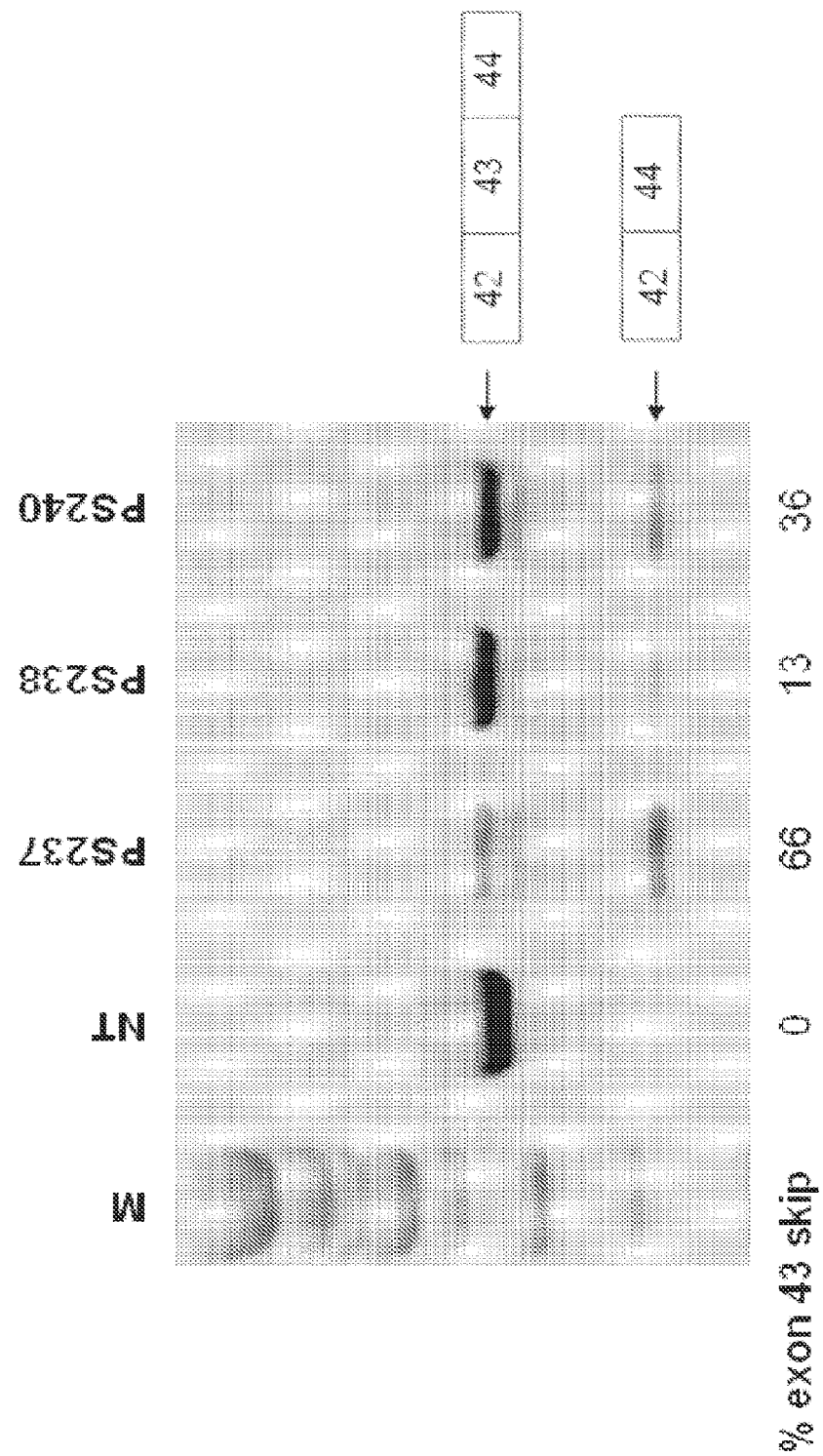

| | | | |
|---|---|---|---|
| 6,379,698 B1 | 4/2002 | Leamon | 424/450 |
| 6,399,575 B1 | 6/2002 | Smith et al. | 514/16 |
| 6,514,755 B1 | 2/2003 | Koob et al. | 435/320.1 |
| 6,623,927 B1 | 9/2003 | Brahmachari et al. | 435/6 |
| 6,653,466 B2 | 11/2003 | Matsuo | 536/24.3 |
| 6,653,467 B1 | 11/2003 | Matsuo et al. | 536/24.5 |
| 6,670,461 B1 | 12/2003 | Wengel et al. | 536/23.1 |
| 6,727,355 B2 | 4/2004 | Matsuo et al. | 536/24.5 |
| 6,794,192 B2 | 9/2004 | Parums et al. | 436/15 |
| 6,902,896 B2 | 6/2005 | Ranum et al. | 435/6 |
| 6,982,150 B2 | 1/2006 | Sheetz et al. | 435/7.2 |
| 7,001,994 B2 | 2/2006 | Zhu | 536/4.1 |
| 7,034,009 B2 | 4/2006 | Pavco et al. | 514/44 |
| 7,118,893 B2 | 10/2006 | Ranum et al. | 435/91.2 |
| 7,189,530 B2 | 3/2007 | Botstein et al. | 435/69.1 |
| 7,202,210 B2 | 4/2007 | Wolfman et al. | 514/12 |
| 7,250,404 B2 | 7/2007 | Felgner et al. | 514/44 |
| 7,355,018 B2 | 4/2008 | Glass | 530/399 |
| 7,405,193 B2 | 7/2008 | Lodish et al. | 514/2 |
| 7,442,782 B2 | 10/2008 | Ranum et al. | 536/23.1 |
| 7,514,551 B2 | 4/2009 | Rabbani et al. | 536/26.6 |
| 7,534,879 B2 | 5/2009 | van Deutekom | 536/24.5 |
| 7,589,189 B2 | 9/2009 | Ichiro et al. | 536/24.5 |
| 7,655,785 B1 | 2/2010 | Bentwich | 536/24.1 |
| 7,771,727 B2 | 8/2010 | Fuselier et al. | 424/185.1 |
| 7,807,816 B2 | 10/2010 | Wilton et al. | 536/24.5 |
| 7,902,160 B2 | 3/2011 | Matsuo et al. | 514/44 |
| 7,960,541 B2 | 6/2011 | Wilton et al. | 536/24.5 |
| 8,084,601 B2 | 12/2011 | Popplewell et al. | 536/24.5 |
| 8,232,384 B2 | 7/2012 | Wilton et al. | 536/24.5 |
| 8,324,371 B2 | 12/2012 | Popplewell et al. | 536/24.5 |
| 8,450,474 B2 | 5/2013 | Wilton et al. | 536/24.5 |
| 8,455,634 B2 | 6/2013 | Wilton et al. | 536/24.5 |
| 8,455,635 B2 | 6/2013 | Wilton et al. | 536/24.5 |
| 8,455,636 B2 | 6/2013 | Wilton et al. | 536/24.5 |
| 8,476,423 B2 | 7/2013 | Wilton et al. | 536/24.5 |
| 8,486,907 B2 | 7/2013 | Wilton et al. | 514/44 |
| 8,524,880 B2 | 9/2013 | Wilton et al. | 536/24.5 |
| 8,637,483 B2 | 1/2014 | Wilton et al. | 514/44 A |
| 2001/0056077 A1 | 12/2001 | Matsuo | 514/44 |
| 2002/0049173 A1 | 4/2002 | Bennett et al. | 514/44 |
| 2002/0055481 A1 | 5/2002 | Matsuo et al. | 514/44 |
| 2002/0115824 A1 | 8/2002 | Engler et al. | 530/524 |
| 2002/0165150 A1 | 11/2002 | Ben-Sasson | 514/12 |
| 2003/0045488 A1 | 3/2003 | Brown et al. | 514/44 |
| 2003/0073215 A1 | 4/2003 | Baker et al. | 435/183 |
| 2003/0082763 A1 | 5/2003 | Baker et al. | 435/183 |
| 2003/0082766 A1 | 5/2003 | Baker et al. | 435/183 |
| 2003/0109476 A1 | 6/2003 | Kmiec et al. | 514/44 |
| 2003/0124523 A1 | 7/2003 | Asselbergs et al. | 435/6 |
| 2003/0134790 A1 | 7/2003 | Langenfeld | 514/12 |
| 2003/0235845 A1 | 12/2003 | van Ommen et al. | 435/6 |
| 2003/0236214 A1 | 12/2003 | Wolff et al. | 514/44 |
| 2004/0101852 A1 | 5/2004 | Bennett et al. | 435/6 |
| 2004/0132684 A1 | 7/2004 | Sampath et al. | 514/44 |
| 2004/0226056 A1 | 11/2004 | Roch et al. | 800/12 |
| 2005/0048495 A1 | 3/2005 | Baker et al. | 435/6 |
| 2005/0096284 A1 | 5/2005 | McSwiggen | 514/44 |
| 2005/0222009 A1 | 10/2005 | Lamensdorf et al. | 514/7 |
| 2005/0246794 A1* | 11/2005 | Khvorova | A61K 31/713 800/286 |
| 2005/0277133 A1 | 12/2005 | McSwiggen | 435/6 |
| 2005/0288246 A1 | 12/2005 | Iversen et al. | 514/44 |
| 2006/0024715 A1 | 2/2006 | Liu et al. | 435/6 |
| 2006/0074034 A1 | 4/2006 | Collins et al. | 514/44 |
| 2006/0099612 A1 | 5/2006 | Nakao et al. | 435/6 |
| 2006/0148740 A1 | 7/2006 | Platenburg | 514/44 |
| 2006/0160121 A1 | 7/2006 | Mounts et al. | 435/6 |
| 2007/0021360 A1 | 1/2007 | Nyce et al. | 514/44 |
| 2007/0082861 A1 | 4/2007 | Matsuo et al. | 514/44 |
| 2007/0134655 A1 | 6/2007 | Bentwich | 435/6 |
| 2007/0141628 A1 | 6/2007 | Cunningham et al. | 435/7.1 |
| 2007/0275914 A1 | 11/2007 | Manoharan et al. | 514/44 |
| 2007/0292408 A1 | 12/2007 | Singh et al. | 424/130.1 |
| 2008/0015158 A1 | 1/2008 | Ichiro et al. | 514/44 |
| 2008/0039418 A1 | 2/2008 | Freier | 514/44 |
| 2008/0113351 A1* | 5/2008 | Naito | A61K 31/713 435/6.11 |
| 2008/0207538 A1 | 8/2008 | Lawrence et al. | 514/41 |
| 2008/0249294 A1 | 10/2008 | Haeberli et al. | 536/24.5 |
| 2009/0099066 A1 | 4/2009 | Moulton et al. | 514/7 |
| 2010/0081627 A1 | 4/2010 | Sampath et al. | 514/47 |
| 2010/0099750 A1 | 4/2010 | McSwiggen et al. | 514/44 R |
| 2010/0130591 A1* | 5/2010 | Sazani | C12N 15/111 514/44 A |
| 2010/0168212 A1 | 7/2010 | Popplewell et al. | 514/44 R |
| 2010/0248239 A1 | 9/2010 | Highsmith, Jr. et al. | 435/6 |
| 2011/0015253 A1 | 1/2011 | Wilton et al. | 514/44 A |
| 2011/0015258 A1 | 1/2011 | Wilton et al. | 514/44 R |
| 2011/0166081 A1 | 7/2011 | Campbell et al. | 514/20.9 |
| 2011/0263682 A1 | 10/2011 | De Kimpe et al. | 514/44 A |
| 2011/0263686 A1 | 10/2011 | Wilton et al. | 514/44 A |
| 2011/0294753 A1 | 12/2011 | De Kimpe et al. | 514/40 |
| 2012/0022144 A1 | 1/2012 | Wilton et al. | 514/44 A |
| 2012/0022145 A1 | 1/2012 | Wilton et al. | 514/44 A |
| 2012/0029057 A1 | 2/2012 | Wilton et al. | 514/44 A |
| 2012/0029058 A1 | 2/2012 | Wilton et al. | 514/44 A |
| 2012/0029059 A1 | 2/2012 | Wilton et al. | 514/44 A |
| 2012/0029060 A1 | 2/2012 | Wilton et al. | 514/44 A |
| 2012/0041050 A1 | 2/2012 | Wilton et al. | 514/44 A |
| 2012/0046348 A1 | 2/2012 | Vaillant et al. | 514/44 R |
| 2012/0108652 A1 | 5/2012 | Popplewell et al. | 514/44 A |
| 2012/0202752 A1 | 8/2012 | Lu | 514/20.9 |
| 2013/0116310 A1 | 5/2013 | Wilton et al. | 514/44 A |
| 2013/0211062 A1 | 8/2013 | Watanabe et al. | 536/24.5 |
| 2013/0217755 A1 | 8/2013 | Wilton et al. | 514/44 A |
| 2013/0253033 A1 | 9/2013 | Wilton et al. | 514/44 A |
| 2013/0253180 A1 | 9/2013 | Wilton et al. | 536/24.5 |
| 2013/0274313 A1 | 10/2013 | Wilton et al. | 514/44 A |
| 2013/0331438 A1 | 12/2013 | Wilton et al. | 514/44 A |
| 2014/0343266 A1 | 11/2014 | Watanabe et al. | 536/23.1 |

FOREIGN PATENT DOCUMENTS

| | | | | |
|---|---|---|---|---|
| EP | | 1160318 | 12/2001 | A61P 21/00 |
| EP | | 1191097 | 3/2002 | A01K 67/027 |
| EP | | 1191098 | 3/2002 | A61K 47/02 |
| EP | | 1380644 | 1/2004 | A61K 31/00 |
| EP | | 1487493 A2 | 12/2004 | A61K 47/48 |
| EP | | 1495769 | 1/2005 | A61K 47/48 |
| EP | | 1501931 | 2/2005 | C12N 15/11 |
| EP | | 1544297 | 6/2005 | C12N 15/11 |
| EP | | 1567667 A1 | 8/2005 | C12Q 1/68 |
| EP | | 1568769 | 8/2005 | C12N 15/11 |
| EP | | 1 619 249 A1 | 1/2006 | C12N 15/11 |
| EP | | 1857548 A1 | 11/2007 | C12N 15/11 |
| EP | | 2 119 783 A1 | 11/2009 | C12N 15/11 |
| EP | | 2 135 948 A2 | 12/2009 | C12N 15/11 |
| KR | | 2003/0035047 | 5/2003 | A61K 48/00 |
| KR | WO 2006121277 A1 * | | 11/2006 | C12Q 1/6895 |
| NL | WO 2006112705 A2 * | | 10/2006 | C12N 15/111 |
| WO | WO 93/01286 A2 | | 1/1993 | C12N 15/11 |
| WO | WO 95/16718 A1 | | 6/1995 | C08F 255/02 |
| WO | WO 95/21184 | | 8/1995 | C07H 19/16 |
| WO | WO 95/30774 | | 11/1995 | C12Q 1/68 |
| WO | WO 97/12899 | | 4/1997 | C07H 21/04 |
| WO | WO 97/30067 | | 8/1997 | C07H 21/00 |
| WO | WO 98/18920 A1 | | 5/1998 | C12N 15/12 |
| WO | WO 98/43993 | | 10/1998 | C07H 21/00 |
| WO | WO 98/49345 A1 | | 11/1998 | C12Q 1/68 |
| WO | WO 98/53804 A1 | | 12/1998 | A61K 31/00 |
| WO | WO 99/16871 | | 4/1999 | C12N 15/11 |
| WO | WO 99/55857 | | 11/1999 | C12N 15/11 |
| WO | WO 99/63975 | | 12/1999 | A61K 31/00 |
| WO | WO 00/24885 A2 | | 5/2000 | C12N 15/11 |
| WO | WO 00/76554 | | 12/2000 | A61K 48/00 |
| WO | WO 01/16312 A2 | | 3/2001 | C12N 15/11 |
| WO | WO 01/59102 A2 | | 8/2001 | C12N 15/11 |
| WO | WO 01/79283 A1 | | 10/2001 | C12N 15/87 |
| WO | WO 01/83503 | | 11/2001 | C07H 21/00 |
| WO | WO 01/083695 | | 11/2001 | C07K 14/47 |
| WO | WO 02/02406 A1 | | 1/2002 | B65B 9/02 |

(56) References Cited

FOREIGN PATENT DOCUMENTS

| | | | |
|---|---|---|---|
| WO | WO 02/24906 | 3/2002 | ............ C12N 15/11 |
| WO | WO 02/26812 | 4/2002 | ............ C07K 14/47 |
| WO | WO 02/29006 A2 | 4/2002 | |
| WO | WO 02/29056 | 4/2002 | ............ C07K 14/47 |
| WO | WO 03/002739 A1 | 1/2003 | ............ C12N 15/11 |
| WO | WO 03/013437 | 2/2003 | |
| WO | WO 03/014145 A2 | 2/2003 | ............... C07K 7/00 |
| WO | WO 03/037172 | 5/2003 | ............ A01N 37/18 |
| WO | WO 03/062258 A1 | 7/2003 | ............ C07H 21/02 |
| WO | WO 03/095647 | 11/2003 | ............ C12N 15/11 |
| WO | WO 2004/11060 A2 | 2/2004 | |
| WO | WO 2004/015106 | 2/2004 | ............ C12N 15/11 |
| WO | WO 2004/016787 | 2/2004 | ............ C12N 15/11 |
| WO | WO 2004/037854 A1 | 5/2004 | ............. C07K 1/04 |
| WO | WO 2004/047741 A2 | 6/2004 | |
| WO | WO 2004/048570 | 6/2004 | ............ C12N 15/11 |
| WO | WO 2004/083432 | 9/2004 | ............ C12N 15/11 |
| WO | WO 2004/083446 | 9/2004 | |
| WO | WO 2004/101787 | 11/2004 | ............ C12N 15/11 |
| WO | WO 2004/108157 A2 | 12/2004 | ............ A61K 39/395 |
| WO | WO 2005/019453 A2 | 3/2005 | ............ C12N 15/11 |
| WO | WO 2005/023836 A2 | 3/2005 | |
| WO | WO 2005/035550 | 4/2005 | |
| WO | WO 2005/085476 A1 | 9/2005 | ............... C12Q 1/68 |
| WO | WO 2005/086768 | 9/2005 | |
| WO | WO 2005/105995 A2 | 11/2005 | ............ C12N 15/11 |
| WO | WO 2005/115439 | 12/2005 | ............ A61K 38/18 |
| WO | WO 2005/115479 A2 | 12/2005 | ............ A61K 48/00 |
| WO | WO 2005/116204 A1 | 12/2005 | ............ C12N 15/09 |
| WO | WO 2006/007910 | 1/2006 | ............ A61K 31/56 |
| WO | WO 2006/017522 | 2/2006 | ............ A61K 48/00 |
| WO | WO 2006/031267 | 3/2006 | ............ C12N 15/11 |
| WO | WO 2006/054262 A2 | 5/2006 | |
| WO | WO 2006/083800 | 8/2006 | |
| WO | WO 2006/108052 | 10/2006 | ............ A61K 47/48 |
| WO | WO 2006/121960 A2 | 11/2006 | ............ C12N 15/11 |
| WO | WO 2007/002904 A2 | 1/2007 | ............... C12Q 1/68 |
| WO | WO 2007/004979 A1 | 1/2007 | ............ A61K 38/00 |
| WO | WO 2007/044362 | 4/2007 | ............ A61K 48/00 |
| WO | WO 2007/089584 | 8/2007 | ............ A61K 48/00 |
| WO | WO 2007/089611 A2 | 8/2007 | ............ C12N 15/11 |
| WO | WO 2007/123402 A2 | 11/2007 | ............ A61K 38/18 |
| WO | WO 2007/135105 A1 | 11/2007 | ............ C12N 15/11 |
| WO | WO 2008/011170 A2 | 1/2008 | ............... C12Q 1/68 |
| WO | WO 2008/018795 A1 | 2/2008 | ............ C12N 15/11 |
| WO | WO 2008/021136 A2 | 2/2008 | ............ A01K 67/027 |
| WO | WO 2008/039418 | 4/2008 | ............ A61K 31/454 |
| WO | WO 2008/043561 | 4/2008 | ............ A61K 48/00 |
| WO | WO 2008/103060 A1 | 8/2008 | ............ C12N 15/11 |
| WO | WO 2009/005793 A2 | 1/2009 | ............ A61K 48/00 |
| WO | WO 2009/008727 A2 | 1/2009 | ............ A61K 47/48 |
| WO | WO 2009/015384 A1 | 1/2009 | ............ A61K 38/00 |
| WO | WO 2009/054725 A2 | 4/2009 | ............ A61K 31/56 |
| WO | WO 2009/099326 A1 | 8/2009 | ............ A61K 48/00 |
| WO | WO 2009/101399 A1 | 8/2009 | ............ A61K 31/712 |
| WO | WO 2009/120887 A2 | 10/2009 | ............ A61K 47/48 |
| WO | WO 2009/135322 A1 | 11/2009 | ............... C12Q 1/68 |
| WO | WO 2009/139630 A2 | 11/2009 | ............ C12N 15/11 |
| WO | WO 2009/144481 A2 | 12/2009 | |
| WO | WO 2009/151600 A2 | 12/2009 | ............ C12N 15/12 |
| WO | WO 2010/044894 A1 | 4/2010 | ............ C07K 19/00 |
| WO | WO 2010/048586 A1 | 4/2010 | ............ C12N 15/113 |
| WO | WO 2010/050802 A2 | 5/2010 | ......... A61K 31/7105 |
| WO | WO 2010/110835 A1 | 9/2010 | ............... C12Q 1/68 |
| WO | WO 2010/115993 A1 | 10/2010 | ............ C12N 15/113 |
| WO | WO 2010/123369 A1 | 10/2010 | ............ C12N 15/113 |
| WO | WO 2011/032045 A1 | 3/2011 | ............ C07H 21/04 |
| WO | WO 2011/057350 A1 | 5/2011 | ............ C12N 15/113 |
| WO | WO 2011/078797 A2 | 6/2011 | ............ G06F 19/20 |
| WO | WO 2011/097641 A1 | 8/2011 | ............ C07H 21/04 |
| WO | WO 2012/029986 | 3/2012 | ............ C12N 15/113 |
| WO | WO 2012/150960 A1 | 11/2012 | ............ A61K 47/48 |
| WO | WO 2013/100190 | 7/2013 | ......... A61K 31/7088 |
| WO | WO 2013/170385 | 11/2013 | ......... A61K 31/7088 |

OTHER PUBLICATIONS

Aartsma-Rus et al., "Targeted exon skipping as a potential gene correction therapy for Duchenne Muscular Dystrophy," *Neuromuscular Disorder*, 2002, 571-577, vol. 12.

Aartsma-Rus et al., "Therapeutic antisense-induced exon skipping in cultured muscle cells from six different patients," *Human Molecular Genetics*, 2004, pp. 907-14, vol. 12, No. 8.

Aartsma-Rus et al., "Comparative analysis of antisense oligonucleotide analogs for targeted DMD exon 46 skipping in muscle cells," *Gene Ther.*, vol. 11, No. 18, pp. 1391-1398 (Sep. 2004).

Aartsma-Rus et al., "Antisense-Induced Multiexon Skipping for Duchenne Muscular Dystrophy Makes More Sense," *Am. J. Hum. Genet.*, 2004, pp. 83-92, vol. 74.

Aartsma-Rus et al., "Functional Analysis of 114 Exon-Internal AONs for Targeted Dmd Exon Skipping: Induction for Steric Hindrance of SR Protein Binding Sites," *Oligonucleotides* 15: 284-297, 2005.

Aartsma-Rus et al., "Therapeutic Modulation of DMD splicing by Blocking Exonic Splicing Enhancer Sites with Antisense Oligonucleotides," *Ann NY Acad Sci* 2006 pp. 74-76 vol. 1082.

Aartsma-Rus et al., "Exploring the Frontiers of Therapeutic Exon Skipping for Duchenne Muscular Dystrophy by Double Targeting within One or Multiple Exons," *Molecular Therapy*, pp. 1-7, 2006.

Aartsma-Rus et al., "Antisense Mediated exon skipping: A Versatile Tool with Therapeutic and Research Applications," *RNA* 2007, pp. 1609-24, vol. 13 No. 10.

Aartsma-Rus et al., "Antisense-Induced Exon Skipping for Duplications in Duchenne muscular Dystrophy," Jul. 5, 2007, *BMC Med. Genet.* 8:43.

Aartsma-Rus et al., "Guidelines for Antisense Oligonucleotide Design and Insight into Splice-modulation Mechanisms." *Molecular Therapy*, vol. 17, No. 3, pp. 548-553 Mar. 2009.

Aartsma-Rus et al., "Theoretic Applicability of Antisense-Mediated Exon Skipping for Duchenne Muscular Dystrophy," *Human Mutation*, vol. 30, No. 3, pp. 293-299, 2009.

Aartsma-Rus et al., "Exonic Sequences Provide Better Targets for Antisense Oligonucleotides Than Splice Site Sequences in the Modulation of Duchenne Muscular Dystrophy Splicing," *Oligonucleotides*, vol. 20, No. 2, 2010, pp. 69-77.

Abbs et al., "A convenient multiplex PCR system for the detection of dystrophin gene deletions: a comparative analysis with cDNA hybridisation shows mistypings by both methods, "*J. Med. Genet.*, 1991, pp. 304-311, vol. 28.

Academisch Ziekenhuis Leiden, Patentee's response during prosecution of opposed patent, dated Jan. 27, 2010.

Agrawal and Kandimalla et al., "Antisense therapeutics: is it as simple as complementary base recognition?" *Mol. Med. Today*, Feb. 2000, vol. 6, pp. 72-81.

Alter et al., "Systemic delivery of morpholino oligonucleotide restores dystrophin expression bodywide and Improves dystrophic pathology," *Nature Medicine*, Feb. 2006;12(2): 175-7, Epub, Jan. 29, 2006.

Anderson et al., "Correlated NOS-I[mu] and myf5 expression by satellite cells in mdx mouse muscle regeneration during NOS manipulation and deflazacort treatment," *Neuromuscular Disorders*, Jun. 2003, vol. 12(5): 388-395.

Anonymous, EPO-Munich, Translation of Japanese Patent Application No. 2000-125448 (D59), 31 pages, dated Sep. 27, 2000.

Anonymous, EPO-Munich, Translation of Japanese Patent Application No. 2000-256547(D61), 42 pages, dated Aug. 23, 2001.

Arap et al., "Steps toward mapping the human vasculature by phage display," *Nat. Med*, vol. 8, No. 2, pp. 121-127 (Feb. 2002).

Arechavala-Gomeza et al., "Comparative Analysis of Antisense Oligonucleotide Sequences for Targeted Skipping of Exon 51 During Dystrophin pre-mRNA Splicing in Human Muscle" *Hum Gene Ther*, pp. 798-810 vol. 18, No. 9, 2007.

Arruda, "The role of immunosuppression in gene and cell based treatments for Duchenne Muscular Dystrophy," Molecular Therapy, Jun. 2007, vol. 15(6): 1040-1041.

(56) References Cited

OTHER PUBLICATIONS

Arzumanov et al., "Inhibition of HIV-1 Tat-dependent trans activation by steric block chimeric 2'-0-methyl/LNA oligoribunucleotides," *Biochemistry*, 2001, vol. 40, pp. 14645-14654.

Austin et al. "Cloning and characterization of alternatively spliced isoforms of Dp71," *Hum. Mol. Genetics*, 1995, vol. 4, No. 9, pp. 1475-1483.

Austin et al., "Expression and synthesis of alternatively spliced variants of Dp71 in adult human brain." *Neuromuscular Disorders*. 10, 187-193, 2000.

Australian Patent Office, Australian Office Action for AU2009240879, dated Jun. 22, 2011.

Barabino et al., "Antisense proves targeted to an internal domain in US snRNP specifically inhibit the second stop of pre-mRNA splicing," *Nucleic Acids Res*. 20(17): 4457-4464, 1992.

Barany, "The ligase chain reaction in a PCR world," PCRMethods Appl., Aug. 1991; 1(1):5-16.

Beggs, et al., "Detection of 98% of DMD/BMD gene deletions by polymerase chain reaction," *Human Genetics*, vol. 86, pp. 45-48 (1990).

Bijvoet et al., "Recombinant Human Acid α-Glucosidase: High Level Production in Mouse Milk, Biochemical Characteristics, Correction of Enzyme Deficiency in GSDII KO mice," *Hum. Mol. Genet.*, vol. 7, No. 11, pp. 1815-1824 (Oct. 1998).

Bremmer-Bout et al., "Targeted exon skipping in transgenic HDMD mice: A model for direct preclinical screening of human-specific antisense oligonucleotides," *Mol. Ther*. Aug. 2004; 10(2):232-40.

Brett et al., "EST comparison indicates 38% of human m RNAs contain possible alternative splice forms," FEBS Lett 474(1): 83-86.

Brown et al., "Structure and mutation of the dystrophin gene," in Dystrophin. Gene, protein and cell biology, (Brown and Lucy, eds). Cambridge University Press, Cambridge, 1997, pp. 1-16.

Brown et al., "Gene delivery with synthetic (non-viral) carriers," *Int. J. Pharm*., vol. 229, Nos. 1-2, pp. 1-21 (Oct. 2001).

Buck et al., "Design Strategies and Performance of Custom DNA Sequencing Primers," *Biotechniques*, 27:528-536, 1999.

Burnett et al., "DNA sequence-specific polyamides alleviate transcription inhibition associated with long GAA. TTC repeats in Friedreich's ataxia," PNAS, pp. 11497-11502, vol. 103, No. 31, 2006.

Canadian Patent Office, Canadian Office Action for CA 2,524,255, dated Jul. 6, 2011.

Caplen et al., "Rescue of polyglutamine-mediated cytotoxicity by double-stranded RNA-mediated RNA interference," *Human molecular genetics*, pp. 175-184, vol. 11, No. 2, 2002.

Cartegni et al., Abstract, "Listening to silence and understanding nonsense: exonic mutations that affect splicing," *Nature Reviews Genetics*, Apr. 2002, pp. 285-298, vol. 3.

Case-Green and Southern, "Studies on the base pairing properties of deoxyinosine by solid phase hybridization to oligonucleotides," *Nucleic Acids Research*, 1994, vol. 22, No. 2, pp. 131-136.

Cavanaugh, Third-Party Submission Under 35 U.S.C. §122(e) and 37 C.F.R. §1.290 for U.S. Appl. No. 11/233,495, 6 pages, Jun. 5, 2013.

Chaubourt et al., "Muscular nitric oxide synthase ([mu]NOS) and utrophin, " *J. of Physiology Paris*, Jan.-Mar. 2002: vol. 96(1-2):43-52.

Coulter et al., "Identification of a new class of exonic splicing enhancers by in vivo selection," *Mol. Cell. Biol*. 17(4) 2143-50, 1997.

Crooke, "In Basic Principles of Antisense Therapeutics," Springer-Verlag, Eds, New York, 1998, pp. 1-50.

Dahlqvist et al., "Functional notch signaling is required for BMP4-induced inhibition of myogenic differentiation," *Development* 130:6089-6099, 2003.

De Angelis et al., "Chimeric snRNA molecules carrying antisense sequences against the splice junctions of exon 51 of the dystrophin pre-mRNA exon skipping and restoration of a dystrophin synthesis in delta 48-50 DMD cells," *PNAS*, Jul. 9, 2002, pp. 9456-9461, vol. 99, No. 14.

Denny et al., "Oligo-riboprobes. Tools for in situ hybridization," Histochemistry (1988) 89:481-493.

Duboc et al., "Effect of Prindopril on the Onset and Progression of Left Ventricular Dysfunction in Duchenne Muscular Dystrophy," *Journal of Amer. Coll. Cardiology*, 45(6): 855-7, Mar. 15, 2005.

Dickson et al., "Screening for antisense modulation of dystrophin pre-mRNA splicing," *Neuromuscul. Disord*., S67-70, Suppl. 1., 2002.

Dirksen et al., "Mapping the SF2/ASF Binding Sites in the Bovine Growth Hormone Exonic Splicing Enhancer," *The Journal of Biological Chemistry*, Sep. 15, 2000, pp. 29170-29177, vol. 275, No. 37.

Dorchies et al., "Green tea extract and its major polyphenol (-)-epigallocatechin gallate improve muscle function in a mouse model for Duchenne muscular dystrophy," *Am J Physiol Cell Physiol* 290: C616-C625, 2006; doi: 0.1152/ajpcell.00424.2005.

Dubowitz, Foreword, *Neuromuscular Disorders* 12 (2002) S1-S2; www.elsevier.com/locate/nmd.

Dubowitz, "Special Centennial Workshop—101st ENMC International Workshop: Therapeutic possibilities in Duchenne Muscular Dystrophy, Nov. 30-Dec. 2, 2001, Naarden, The Netherlands" *Neuromuscul Disord*. May 2002; 12(4):421-31.

Dunckley et al., "Modification of splicing in the Dystrophin gene in cultured MDX muscle cells by antisense oligoribonucleotides," *Hum Mol Genet*.,7(7):1083-90. 1995.

Dunckley et al., "Modulation of Splicing in the DMD Gene by Antisense Oligoribonucleotides," *Nucleosides & Nucleotides*, 1997, pp. 1665-1668, vol. 16, No. 7-9.

El-Andaloussi et al., "Induction of splice correction by cell-penetrating peptide nucleic acids," *J. Gene Med.*, vol. 8, No. 10, pp. 1262-1273 (Oct. 2006).

Erba et al., "Structure, chromosome location, and expression of the human gamma-actin gene: differential evolution, location, and expression of the cytoskeletal beta- and gamma-actin genes," *Mol. Cell. Biology*, 1988, 8(4):1775-89.

Errington et al., "Target selection for antisense oligonucleotide induced exon skipping in the dystrophin gene," *J Gene Med*. Jun. 2003; 5(6):518-27.

Espinos, E., et al., "Efficient Non-Viral DNA-Mediated Gene Transfer to Human Primary Myoblasts Using Electroporation," *Neuromuscular Disorders*, 10 (2001), pp. 341-349.

European Patent Office, International Search Report, International Application No. PCT/NL01/00697, dated Dec. 21, 2001.

European Patent Office, Partial European Search Report—Application No. EP 03 07 7205, dated Dec. 10, 2003 (5 pages).

European Patent Office, European Search Report Annex—Application No. EP 03 07 7205, dated Dec. 10, 2003 (1 page).

European Patent Office, International Search Report, International Application No. PCT/NL2004/000196, dated Oct. 28, 2004.

European Patent Office, International Search Report, PCT/NL2006/000209, Oct. 5, 2006.

European Patent Office, Office Action—Application No. EP 05 076 770.6, dated Jan. 29, 2007 (5 pages).

European Patent Office, International Search Report, International Application No. PCT/NL 2008/050673, dated Feb. 9, 2009.

European Patent Office, International Search Report, International Application No. PCT/NL 2008/050475, dated Jun. 25, 2009.

European Patent Office, International Search Report, International Application No. PCT/NL 2008/050470, dated Jul. 2, 2009.

European Patent Office, International Search Report for PCT/NL2009/050113 dated Jun. 30, 2010.

Fainsod A, et al., "The dorsalizing and neural inducing gene follistatin is an antagonist of BMP-4" *Mech Dev*. Apr. 1997; 63(1): 39-50.

Feener et al., "Alternative splicing of human dystrophin mRNA generates isoforms at the carboxy terminus," *Nature*, 338 (6215): 509-511, 1989.

(56) References Cited

OTHER PUBLICATIONS

Fluiter, "In Vivo tumor growth inhibition and biodistribution studies of locked nucleic acid (LNA) antisense oligonucleotides," *Nucl. Acids Research* 2003, vol. 31., No. 3., pp. 953-962.
Fu et al., "An Unstable Triplet Repeat in a Gene Related to Myotonic Muscular Dystrophy", *Science*, vol. 255, 1256-1258, 1992.
Furling et al., "Viral vector producing antisense RNA restores myotonic dystrophy myoblast functions", *Gene Therapy*, 10, 795-802, 2003.
Galderisi et al., "Myotonic dystrophy: antisense oligonucleotide inhibition of DMPK gene expression in vitro," *Biochem Biophys Res Commun* 221:750-754, 1996.
Galderisi et al., "Antisense Oligonucleotides as Therapeutic Agents," *Journal of Cellular Physiology*, vol. 181, pp. 251-257 (1999).
Garcia-Blanco et al., "Alternative splicing in disease and therapy," *Nat. Biotechnol.*, vol. 22, No. 5, pp. 535-546 (May 2004).
GenBank, GenBank accession No. AZ993191.1, 2M0278E12F mouse 10kb plasmid UUGC2M library Mus muscu genomic clone UUGC2M0278E12F, genomic survey sequence, entry created and last updated on Apr. 27, 2001.
GenBank, GenBank accession No. EW162121.1, rfat0126_k17. ylfatSus scrofa cDNA5-, mRNA sequence, entry created on Aug. 13, 2007, last updated on Mar. 3, 2011.
Ghosh et al., "Mannose 6-phosphate receptors: new twists in the tale," *Nat. Rev. Mol. Cell Biol.*, vol. 4, No. 3, pp. 202-212 (Mar. 2003).
Ginjaar et al., "Dystrophin nonsense mutation induces different levels of exon 29 skipping and leads to variable phenotypes within one BMD family," *European Journal of Human Genetics*, 8, 793-796, 2000.
Gollins et al., "High-efficiency plasmid gene transfer into dystrophic muscle," *Gene Ther.*, vol. 10, No. 6, pp. 504-512 (Mar. 2003).
Grady, "Promising Dystrophy Drug Clears Early Test," The New York Times, Dec. 27, 2007.
Granchelli et al., "Pre-clinical screening of drugs using the mdx mouse," *Neuromuscular Disorders*, Pergamon Pres. vol. 10 (4-5): 235-239, Jun. 2000.
Gryaznov, "Oligonucleotide N3'--> P5' phosphoramidates as potential therapeutic agents," *Biochemistry et Biophys*. Acta, 1999, vol. 1489, pp. 131-140.
GSK Press Release, "GSK and Prosensa Announce Primary Endpoint Not Met in Phase III Study of Drisapersen in Patients With Duchenne Muscular Dystrophy," *Prosensa Press Release*, 3 pages, Sep. 20, 2013.
Goemans, et al., "Systemic Administration of PRO051 in Duchenne's Muscular Dystrophy," *The New England Journal of Medicine*, vol. 364, No. 16, 11 pages, 2011.
Gramolini, et al, "Expression of the Utrophin Gene During Myogenic Differentiation," *Nucleic Acids Research*, 1999, vol. 27, No. 17, pp. 3603-3609.
Habara, et al., In vitro splicing analysis showed that availability of a cryptic splice site is not a determinant for alternative splicing patterns caused by +1G->A mutations in introns of the dystrophin gene, *J. Med. Genet*46:542-547, 2009, 6 pages.
Hagiwara et al., "A novel point mutation (G-1 to T) in a 5' splice donor site of intron 13 of the dystrophin gene results in exon skipping and is responsible for Becker muscular dystrophy," *Am J. Hum Genet*. Jan. 1994;54(1):53-61.
Handa et al., "The AUUCU repeats responsible for spinocerebellar ataxia type 10 form unusual RNA hairpins," *Journal of Biological Chemistry* 280(32):29340-29345 (2005).
Hansen, Product Development—Addition by subtraction, BioCentury, The Bernstein Report on BioBusiness, Jan. 7, 2008, p. A28 of 38.
Harding, et al., "The Influence of Antisense Oligonucleotide Length on Dystrophin Exon Skipping," *Molecular Therapy*, vol. 15, No. 1, pp. 157-166, Jan. 2007.

Hasholt et al., "Antisense downregulation of mutant huntingtin in a cell model," *Journal of Gene Medicine*, 2003, pp. 528-538, vol. 5, No. 6.
Hassan, "Keys to the Hidden Treasures of the Mannose 6-Phosphate/Insulin-Like Growth Factor 2 Receptor", *Am. J. Path.*, vol. 162, No. 1, pp. 3-6 (Jan. 2003).
Heemskerk et al., "In vivo comparison of 2'-O-methyl phosphorothioate and morpholino antisense oligonucleotides for Duchenne muscular dystrophy exon skipping," *J. Gene Medicine* (2009), 11:257-266.
Heemskerk et al., 2009 Development of Antisense-Mediated Exon Skipping as a Treatment for Duchenne Muscular Dystrophy Ann NY Acad Sci vol. 1175 pp. 71-79.
Heemskerk, et al. 2010 Preclinical PK and PD Studies on 2' O-methyl-phosphorothioate RNA antisense Oligonucleotides in the MDX Mouse Model Mol. Ther vol. 18(6) pp. 1210-1217.
Henderson et al., "The Basic Helix-Loop-Helix Transcription factor HESR1 Regulates Endothelial Cell Tube Formation," *The Journal of Biological Chemistry*, vol. 276, No. 9, pp. 6169-6176, 2001.
Highfield, "Hope for muscular dystrophy drug," *The Daily Telegraph*, Dec. 28, 2007.
Hoffman et al., "Somatic reversion/suppression of the mouse mdx phenotype in vivo." *J. of the Neurological Sciences*, 1990, 99: 9-25.
Hoffman, "Skipping toward Personalized Molecular Medicine," *N. England J. Med.*, Dec. 27, 2007, pp. 2719-2722, vol. 357, No. 26.
Hussey et al., "Analysis of five Duchenne muscular dystrophy exons and gender determination using conventional duplex polymerase chain reaction on single cells," *Molecular Human Reproduction*, 1999, pp. 1089-1094, vol. 5, No. 11.
Hyndman, "High affinity binding of transferrin in cultures of embryonic neurons from the chick retina.," Brain Res., Nov. 8, 1991;564(1):127-31.
Iezzi et al., "Deacetylase inhibitors increase muscle cell size by promoting myoblast recruitment and fusion through induction of follistation," *Development Cell* 6:673-684, 2004.
Ikezawa et al., "Dystrophin gene analysis on 130 patients with Duchenne Muscular dystrophy with a special reference to muscle mRNA analysis," *Brain & Develop.* 20:165-168, 1998.
Ito et al., "One of three examined purine-rich sequences selected from dystrophin exons exhibits splicing enhancer activity," *Acta Myologica*, vol. XX, pp. 151-153 (2001).
Ito et al., "Purine-Rich Exon Sequences are not Necessarily Splicing Enhancer Sequence in the Dystrophin Gene," *Kobe J. Med. Sci.* 47, 193/202, Oct. 2001.
Jou, et al., "Deletion Detection in the Dystrophin Gene by Multiplex Gap Ligase Chain Reaction and Immunochromatographic Strip Technology," *Human Mutation*, 5:86-93, 1995.
Karras et al., "Deletion of Individual Exons and Induction of Soluble Murine Interleukin-5 Receptor-alpha Chain Expression through Antisense Oligonucleotide-Mediated Redirection of Pre-mRNA Splicing," *Molecular Pharmacology*, pp. 380-387, vol. 58, 2000.
Katholieke Universieit Leuven, Letter from Katholike Universiteit Leuven to Dr. N. Goemans, Ghild Neurology, UZ dated Jan. 22, 2008, regarding a Phase 1/11, open label, escalating dose, pilot study to assess the effect, safety, tolerability and pharmacokinetics of multiple subcutaneous doses of PRO051 in patients with Duchenne Muscular Dystrophy. PRO051-02 (translation provided).
J.A. Kemp, Request for an Opinion under Section 74(A) in relation to Patent No. EP (UK) 1619249B in the name of Academisch Ziekenhuis Leden, 33 pages, dated Apr. 20, 2009.
Kendall et al., "Dantrolene Enhances Antisense-Mediated Exon Skipping in Human and Mouse Models of Duchenne Muscular Dystrophy," *Sci Transl* Med 4, 164ra160 (2012).
Kerr et al., "BMP Regulates Skeletal Myogenesis at Two Steps," Molecular Cellular Proteomics 2.9:976. 123.8, 2003, [Abstract].
Kinali et al., 2009 Local Restoration of Dystrophin Expression with the Morpholino Oligomer AVI-4658 in Duchenne Muscular Dystrophy: a Single-blind, Placebo-Controlled Dose-Escalation, Proof of Concept Study, *Lance Neurol*. vol. 8(10), pp. 918-928.
Kurreck et al., "Design of antisense oligonucleotides stabilized by locked nucleic acids," *Nucleic Acids Research*, 2002, vol. 30, No. 9, pp. 1911-1918.

(56) References Cited

OTHER PUBLICATIONS

Langlois et al., "Hammerhead ribozyme-mediated destruction of nuclear foci in myotonic dystrophy myoblasts," *Molecular therapy*, 2003, pp. 670-680, vol. 7, No. 5.

Laptev et al., "Specific inhibition of expression of a human collagen gene (COL1A1) with modified antisense oligonucleotides. The most effective target sites are clustered in double-stranded regions of the predicted secondary structure for the mRNA," *Biochemistry* 33(36):11033-11039, 1994.

Lee et al., "Receptor mediated uptake of peptides that bind the human transferrin receptor", *Eur. J. Biochem.* 268, 2004-2012, 2001.

Lewin, Genes VII, Chapter 22, Nuclear Splicing, pp. 704-705, Jan. 2000.

Liu et al., "Identification of functional exonic splicing enhancer motifs recognized by individual SR proteins," *Genes & Development*, 1998, pp. 1998-2012, vol. 12.

Liu et al., "A mechanism for exon skipping caused by nonsense or missense mutations in BRCA1 and other genes," *Nat Genet*, 27(1):55-8, Jan. 2001.

Liu et al., "Specific inhibition of Huntington's disease gene expression by siRNAs in cultured cells", *Proc. Japan Acad.* 79, Ser. B, 293-298, 2003.

Liu, et al., "Efficiency of DNA Transfection of Rat Heart Myoblast Cells H9c2(2-1) by Either Polyethyleneimine or Electroporation," *Appl Biochem Biotechnol* (2011) 164: 1172-1182.

Lonza, "Amaxa Cell Line Nucleofector Kit V" for C2C12, 4 pages, 2009.

Lu et al., "Massive Idiosyncratic Exon Skipping Corrects the Nonsense Mutation in Dystrophic Mouse Muscle and Produces Functional Revertant Fibers by Clonal Expansion," *The Journal Cell Biology*, Mar. 6, 2000, pp. 985-995, vol. 148, No. 5.

Lu et al., "Non-viral gene delivery in skeletal muscle: a protein factory," *Gene Ther.*, vol. 10, No. 2, pp. 131-142 (Jan. 2003).

Lu et al., "Functional Amounts of Dystrophin Produced by Skipping the Mutated Exon in the MDX Dystrophic Mouse," *Nat Med*, 8: 1009-1014, 2003.

Lu et al., "Systemic delivery of antisense oligoribonucleotide restores dystrophin expression in body-wide skeletal muscles," *Proc. Natl. Acad. Sci. USA.*, vol. 102, No. 1, pp. 198-203 (Jan. 2005).

Ludolph, D., et al., "Transcription Factor Families: Muscling in on the Myogenic Program," *Dept. of Biological Sciences*, Dec. 1995 9(15): 1595-604.

Mann et al., "Antisense-induced exon skipping and synthesis of dystrophin in the mdx mouse," *Proc Natl Acad Sci USA*, 98(1):42-7, Jan. 2, 2001.

Mann et al., "Improved antisense oligonucleotide induced exon skipping in the mdx mouse model of muscular dystrophy," *J Gene Med.* Nov.-Dec. 2002:4(6):644-54.

Martin and Castro, "Base pairing involving deoxyinosine: implications for probe design," *Nucleic Acids Research*, vol. 13, No. 24, 1985.

Martiniuk et al., "Correction of glycogen storage disease type II by enzyme replacement with a recombinant human acid maltase produced by over-expression in a CHO-DHFR(neg) cell line," *Biochem. Biophys. Res. Commun.*, vol. 276, No. 3, pp. 917-923, Abstract (Oct. 2000).

Matsuo et al., "Exon Skipping during Splicing of Dystrophin mRNA Precursor due to an Intraexon Deletion in the Dystrophin Gene of Duchenne Muscular Dystrophy Kobe," *J. Clin. Invest.* 87, 2127-2131, 1991.

Matsuo et al., "Partial deletion of a dystrophin gene leads to exon skipping and to loss of an intra-exon hairpin structure from the predicted mRNA precursor" *Biochem. Biophys. Res. Commun.* 182(2):495-500, 1992.

Matsuo, "Duchenne and Becker Muscular Dystrophy: From Gene Diagnosis to Molecular Therapy", *IUBMB Life*, vol. 53, pp. 147-152 (2002).

Matteucci, "Structural modifications toward improved antisense oligonucleotides" *Perspectives in Drug Disc and Design*, 1996, vol. 4, pp. 1-16.

McClorey et al., "Induced Dystrophin Exon Skipping in Human Muscle Explants," *Neuromuscul Disord*, pp. 583-590, vol. 16, No. 910, 2006.

McClorey et al., "Antisense oligonucleotide-induced exon skipping restores dystrophin expression in vitro in a canine model of DMD," *Gene Therapy*, vol. 13, pp. 1373-1381, 2006.

Medical News Today, LUMC and Prosensa report positive results of DMD study, Pharmaceutical Business Review Online, dated Dec. 28, 2007, <http://www.pharmaceutical-business-review.com/article.sub.--news.sub.- --print.asp?guid=8462FD44-F35D-4EOB-BC>.

Medical News Today, New Clinical Trial Results Show How Personalized Medicine Will Alter Treatment of Genetic Disorders, Medical News Today, Dec. 29, 2007 <http://www.medicalnewstoday.com/article/92777.php>.

Miller KJ et al., "Antisense oligonucleotides: strategies for delivery" *PSST* vol. 1, No. 9; Dec. 1998; pp. 377-386.

Monaco et al., "An Explanation for the Phenotypic Differences between Patients Bearing Partial Deletions of the DMD Locus," *Genomics*, 1988, pp. 90-95, vol. 2.

Moon et al., "Target site Search and effective inhibition of leukaemic cell growth by a covalently closed multiple anti-sense oligonucleotide to c-myb," *The Biochemical Journal*, Mar. 1, 2000, vol. 346 Pt 2, pp. 295-303.

Munroe, "Antisense RNA inhibits splicing of pre-mRNA in vitro" *EMBO J.* 7(8):2523-2532, 1988.

Muntoni et al., "A Mutation in the Dystrophin Gene Selectively Affecting Dystrophin Expression in the Heart." *J. Clin Invest*, vol. 96 Aug. 1995, 693-699.

Muntoni, et al., 149th ENMC International Workshop and 1st TREAT-NMD Workshop on: "Planning Phase I/II Clinical trials using Systemically Delivered Antisense Oligonucleotides in Duchenne Muscular Dystrophy," *Neuromuscular Disorders*, 2008, pp. 268-75, vol. 18.

Nakamura, et al., 2009 Exon Skipping Therapy for Duchenne Muscular Dystrophy Neuropathology vol. 29(4) pp. 494-501.

Nishio et al., "Identification of a novel first exon in the human dystrophin gene and of a new promoter located more than 500 kb upstream of the nearest known promoter," *J. Clin. Invest.* 94:1037-1042, 1994.

Onlo, Comparative analysis of AONs for inducing the skipping of exon 45 and 53 from the dystrophin gene in human control muscle cells, EP1619249, 3 pages, Aug. 23, 2013.

Onlo, Comparative Analysis of AONs for inducing the skipping of exon 53 from the dystrophin gene in human control muscle cells., EP1619249, 3 pages, Jan. 8, 2014.

Onlo Nederlandsch Octrooibureau, Grounds of Appeal,—EP1619249, 16 pages, Aug. 23, 2013.

Onlo Nederlandsch Octrooibureau, List of all submitted documents—EP1619249, 4 pages, Aug. 23, 2013.

Onlo Nederlandsch Octrooibureau, Reply to the Grounds of Appeal filed in Opposition Proceedings of EP1619249, 35 pages, dated Jan. 8, 2014.

Opalinska and Gewirtz, "Nucleic-acid therapeutics: basic principles and recent applications," *Nature Reviews Drug Discovery*, 2002, vol. 1, pp. 503-514.

Oxford Dictionary of English, Oxford Dictionary of English, 2nd Edition, Revised, Oxford University Press, p. 158, 2005.

O'Shaughnessy et al., "Superior Survival with Capecitabine Plus Docetaxel Combination Therapy in Anthracycline-Pretreated Patients with Advanced Breast Cancer: Phase III Trial Results," *Journal of Clinical Oncolo*, vol. 20 No. 12 Jun. 15, 2002: pp. 2812-2823.

C. Pallard, Letter from C. Pallard dated Jun. 10, 2014 re: Patentee in the Above-Identified Opposition Appeal Proceedings, 25 pages.

Patel et al., "The Function of Myostatin and strategies of Myostatin blockade-new hope for therapies aimed at promoting growth of skeletal muscle," *Neuromuscular Disorders* 15(2):117-126, 2005.

(56) References Cited

OTHER PUBLICATIONS

Peterson TC, et al., "Selective Down-Regulation of c-jun Gene Expression by Pentoxifylline and c-jun Antisense Interrupts Platelet-Derived Growth Factor Signaling: Pentoxifylline Inhibits Phosphorylation of c-Jun on Serine 73" *Mol Pharmacol.* Jun. 2002;61(6): 1476-88.

Phillips MI, "Antisense Inhibition and Adeno-Associated Viral Vector Delivery for Reducing Hypertension" *Hypertension,* 1997; vol. 29, 177-187.

Politano et al., "Gentamicin administration in Duchenne Patients with Premature stop codon. Preliminary results," *Acta Myologica* 22:15-21, 2003.

Popplewell, et al., Design of Phosphorodiamidate Morpholino Oligomers (PMOs) for the Induction of Exon Skipping of the Human *DMD* Gene Mol. Ther vol. 17(3) pp. 554-561 (2009).

Pramono et al., Abstract, "Induction of Exon Skipping of the Dystrophin Transcript in Lymphoblastoid Cells by Transfecting an Antisense Oligodeoxynucleotide Complementary to an Exon Recognition Sequence," *Biochemical and Biophysical Research Communications,* Sep. 13, 1996, pp. 445-449, vol. 226, No. 2.

Prosensa Therapeutics B.V., Letter from Prosensa Therapeutics B.V. To Federal Agency for Medicines and Health Products dated Jan. 9, 2008, regarding a Phase I/II, open label, escalating dose, pilot study to assess the effect, safety, tolerability and pharmacokinetics of multiple subcutaneous doses of PRO051 in patients with Duchenne muscular dystrophy.

Radley et al., "Duchenne muscular dystrophy: Focus on pharmaceutical and nutritional interventions," International J. of Biochem. and Cell Biol., vol. 39(3):469-477, Oct. 2006.

Rando, "Oligonucleotide-mediated gene therapy for muscular dystrophies," *Neuromuscular Disorders,* 2002, vol. 12, pp. S55-S60.

Reitter, B., "Deflazacort vs. Prednisone in Duchenne muscular dystrophy: trends of an ongoing study," *Brain Dev.* 1995; 17 Suppl1:39-43.

Reuser et al., "Uptake and Stability of Human and Bovine Acid α-Glucosidase in Cultured Fibroblasts and Skeletal Muscle Cells from Plycogenosis Type II Patients," *Exp. Cell Res.,* vol. 155, No. 1, pp. 178-189 (Nov. 1984).

Authorized Officer: Romano, Alper, International Search Report for PCT/NL2010/050230, dated Jun. 24, 2010, 5 pages.

Roberts et al., "Direct diagnosis of carriers of Duchenne and Becker muscular dystrophy by amplification of lymphocyte RNA," *Lancet,* 336 (8730-8731): 1523-6, 1990.

Roberts et al., "Direct detection of dystrophin gene rearrangements by analysis of dystrophin mRNA in peripheral blood lymphocytes," *Am. J. Hum. Genet.* 49(2): 298-310, 1991.

Roberts et al., "Exon structure of the human dystrophin gene," *Genomics,* 1993, vol. 16, No. 2, pp. 536-538, 1993.

Roberts et al., "Searching for the 1 in 2,400,000: a review of dystrophin gene point mutations," *Hum. Mut.* 4:1-11, 1994.

Rolland et al., "Over-activity of exercise-sensitive cation channels and their impaired modulation by IGF-1 in mdx native muscle fibers: beneficial effect of pentoxifylline," Dec. 2006; Epub Sep. 28, *Neurobiology Disease,* vol. 24(3): 466-474.

Rosen et al., "Combination Chemotherapy and Radiation Therapy in the Treatment of Metastatic Osteogenic Sarcoma," *Cancer* 35: 622-630, 1975.

Samoylova et al., "Elucidation of muscle-binding peptides by phage display screening," *Muscle Nerve,* vol. 22, No. 4, pp. 460-466 (Apr. 1999).

Sarepta Therapeutics Inc., "Sarepta Therapeutics and University of Western Australia Announce Exclusive Worldwide Licensing Agreement for Exon-Skipping Program in Duchenne Muscular Dystrophy," *News Release,* EP1619249, 3 pages, Apr. 11, 2013.

Scanlon, "Anti-genes: siRNA, ribozymes, and antisense," *Curr. Pharmaceutical Biotechnology,* 2004, vol. 5, pp. 415-420.

Schnell, "Declaration of Dr. Fred Schnell in Support of Appeal of the Opposition Division's Decision to Maintain EP-B1 1 619 249 in amended form," 6 pages, Jan. 8, 2014.

Segalat et al., "Capon expression in skeletal muscle is regulated by position, repair, NOS activity, and dystrophy," *Experimental Cell Research,* Jan. 2005, vol. 302(2): 170-179. cited by applicant.

Sertic et al., "Deletion screening of the Duchenne/Becker muscular dystrophy gene in Croatian population" *Coll. Antropol.* 1997, 1:151-156.

Shapiro and Senapathy, "RNA splice junctions of different classes of eukaryotes: sequence statistics and functional implications in gene expression." *Nucleic Acids Research,* 1987, vol. 15. No. 17, pp. 7155-7174.

Sherratt et al., "Exon Skipping and Translation in Patients with Frameshift Deletions in the Dystrophin Gene," *Am. J. Hum. Genet,* 1993, pp. 1007-1015, vol. 53.

Shiga et al., "Disruption of the Splicing Enhancer Sequence within Exon 27 of the Dystrophin Gene by a Nonsense Mutation Induces Partial Skipping of the Exon and Is Responsible for Becker Muscular Dystrophy," *J. Clin. Invest.,* Nov. 1997, pp. 2204-2210, vol. 100, No. 9.

Simoes-Wust et al., "bcl-xL Antisense Treatment Induces Apoptosis in Breast Carcinoma Cells," *Int. J. Cancer,* 2000, pp. 582-590, vol. 87.

Singh et al., "Proportion and pattern of dystrophin gene deletions in North Indian Duchenne and Becker muscular dystrophy patients," *Hum Genet,* 99: pp. 206-208, 1997.

Smith et al., "Muscle-specific peptide #5", Mar. 23, 1999. From: http://www.ebi.ac.uk/cgi-bin/epo/epofetch?AAW89659 downloaded Jul. 16, 2007 (XP 002442550).

Spitali, et al., Exon skipping mediated dystrophin reading frame restoration for small mutations *Hum Mut* vol. 30(11) pp. 1527-1534 (2009).

Squires, "An Introduction to Nucleoside and Nucleotide Analogues," *Antiviral Therapy*6 (Suppl. 3): 1-14, 2001.

Sterrenburg et al., "Gene expression of profiling highlights defective myogenesis in DMD patients and a possible role for bone morphogenetic protein 4," *Neurobiology of Disease* 23(1):228-236 (2006).

Summerton et al., "Morpholino Antisense Oligomers: Design, Preparation, and Properties," *Antisense & Nucleic Acid Drug Development,* vol. 7, pp. 187-195 (1997).

Summerton, "Morpholino antisense oligomers: the case for an RNase H-independent structural type," *Biochimica et Biophysica Acta* 1489, pp. 141-158, 1999.

Surono et al., "Six Novel Transcripts that Remove a Huge Intron Ranging from 250 to 800 kb Are Produced by Alternative Splicing of the 5' Region of the Dystrophin Gene in Human Skeletal Muscle," *BBRC* 239 895-899 (1997).

Surono et al., "Chimeric RNA/ethylene-Bridged Nucleic Acids Promote Dystrophin Expression in Myocytes of Duchenne Muscular Dystrophy by Inducing Skipping of the Nonsense Mutation-Encoding Exon Hum Gene Ther.," vol. 15(8) pp. 749-757 (2004).

Suter et al., "Double-target antisense U7 snRNAs promote efficient skipping of an aberrant exon in three human B-thalassemic mutations," Human Molecular Genetics, 1999, pp. 2415-2423, vol. 8, No. 13.

Suwanmanee et al., "Restoration of Human b-globin Gene Expression in Murine and Human IVS2-654 Thalassemic Erythroid Cells by Free Uptake of Antisense Oligonucleotides" Mol. Pharmacology 62(3):545-553.

Takeshima et al., "Modulation of In Vitro Splicing of the Upstream Intron by Modifying an Intra-Exon Sequence Which is Deleted from the Dystrophin Gene in Dystrophin Kobe," J. Clin. Invest., Feb. 1995, pp. 515-520, vol. 95.

Takeshima Y, et al., "Expression of Dystrophin Protein in Cultured Duchenne Muscular Dystrophy Cells by Exon Skipping Induced by Antisense Oligonucleotide" (Abstract); Abstract of the Japan Society of Human Genetics General Meeting Program, 8 pages, Nov. 17-19, 1999.

Takeshima et al., "Oligonucleotides Against a Splicing Enhancer Sequence Led to Dystrophin Production in Muscle Cells From a Duchenne Muscular Dystrophy Patient Brain Dev," 23:788-90, Dec. 2001.

(56) References Cited

OTHER PUBLICATIONS

Takeshima, et al., "Basic research for treatment of Duchene muscular dystrophy using induction of exon skipping by means of antisense oligo DNA: effect of in vivoadministration in mice," *Park IP Tranlations*, vol. 15, No. 2, 6 pages, 2004.
Takeshima, et al., "Intravenous Infusion of an Antisense Oligonucleotide Results in Exon Skipping in Muscle Dystrophin mRNA of Duchenne Muscular Dystrophy," Pediatric Research, May 2006, 59, 5, pp. 690-694.
Tanaka et al., "Polypurine Sequences within a Downstream Exon Function as a Splicing Enhanced, Molecular and Cellular Biology", Feb. 1994, pp. 1347-1354, vol. 14, No. 2.
Thanh et al., "Characterization of revertant muscle fibers in Duchenne muscular dystrophy, using exon-specific monoclonal antibodies against dystrophin " *Am. J. Hum. Genet*. 1995, vol. 56, pp. 725-731.
Tennyson et al., "The human dystrophin gene requires 16 hours to be transcribed and is contranscriptionally spliced," *Nature Genetics*, vol. 9, pp. 184-190, Feb. 1995.
Tian et al., "Selection of novel exon recognition elements from a pool of random sequences." *Mol Cell Biot* 15(11):6291-6298, 1995.
TREAT-NMD, TREAT-NMD, Neuromuscular Network, Jan. 11, 2008.
Tsuchida, "Peptides, Proteins & Antisense: the role of myostatin and bone morphogenetic proteins in muscular disorders," Expert Opinion of Biologica Therapy 6(2):147-153 (2006).
Tsuchida, "The role of myostatin and bone morphogenetic proteins in muscular disorders," Expert Opinion of Biologica Therapy 6(2): 147-154 (2006).
van Deutekom et al., "Antisense-induced exon skipping restores dystrophin expression in DMD patient derived muscle cells," *Hum Mol Genet*. Jul. 15, 2001:10(15:1547-54).
van Deutekom et al., "Advances in Duchenne Muscular Dystrophy gene therapy", *Nature Reviews Genetics*, vol. 4, Oct. 2003, 774-783.
van Deutekom et al., "Local Dystrophin Restoration with Antisense Oligonucleotide PRO051," *N. England J. Med.*, Dec. 27, 2007, pp. 2677-2686.
van Deutekom, Declaration of Dr. JCT van Deutekom, EP1619249, 2 pages, Aug. 23, 2013.
van Deutekom, Declaration of Dr. JCT Van Deutekom, EP1619249, 6 pages, Jan. 7, 2014.
Van Ommen, The Therapeutic Potential of Antisense-Mediated Exon-Skipping Curr Opin Mol. Ther. vol. 10(2) pp. 140-149, 2008.
Van Vliet et al., "Assessment of the feasibility of exon 45-55 multiexon skipping for Duchenne Muscular Dystrophy," *BMC Medical Genetics*, Dec. 2008, vol. 9:105, 7 pages.
Varani et al., "The G.U. wobble base pair: A fundamental building block of RNA structure crucial to RNA function in diverse biological systems," *EMBO Rep.*, vol. 1, pp. 18-23 (Jul. 2000).
Verhaart et al., Prednisolone treatment does not interfere with 2'-0-methyl phosphorothioate antisense-mediated exon skipping in Duchenne Muscular Dystrophy, *Hum Gene Ther*. Mar. 2012; 23(3):262-73. Epub Jan. 26, 2012.
Verreault et al., "GENE silencing in the development of personalized cancer treatment: the targets, the agents and the delivery systems." *Curr. Gene Therapy*, 2006, vol. 6, pp. 505-553.
Vickers et al., "Efficient reduction of target RNAs by small interfering RNA and RNase H-dependent antisense agents. A comparative analysis." *J. Biol. Chem*. 278(9):7108-7118 (2003).
Vossius & Partners, "Statement of Grounds of Appeal" filed in the opposition proceeding of EP1619249; dated Aug. 23, 2013, 41 pages.
Vossius & Partners, Reply of the Opponent to the Grounds of Appeal, 31 pages, Jan. 8, 2014.
Wang et al., "Adeno-associated virus vector carrying human minidystrphin genes effectively ameliorates muscular dystrophy in mdx mouse model," Dec. 5, 2000, P.N.A.S. 97(25):13714-13719.

Wang et al., "Sustained AAV-mediated Dystrophin Expression in a canine Model of Duchenne Muscular Dystrophy with a Brief Course of Immunosuppression," www.moleclartherapy.org, vol. 15, No. 6, pp. 1160-1166, Jun. 2007.
Watakabe et al., "The role of exon sequences in splice site selection," Genes & Development, pp. 407-418, vol. 7, 1993.
Watkins and Santalucia, "Nearest-neighbor thermodynamics of deoxyinosine pairs in DNA duplexes," Nucleic Acids Research, vol. 33, No. 19, 2005.
Weiler et al., "Identical mutation in patients with limb girdle muscular dystrophy type 2B or Miyoshi myopathy suggests a role for modifier gene(s)," *Human Molecular Genetics*, vol. 8, No. 5, pp. 871-877 (1999).
Weisbart et al., Cell type specific targeted intracellular delivery into muscle of a monoclonal antibody that binds myosin IIb, *Mol. Immun.*, vol. 39, No. 13, pp. 783-789 (Mar. 2003) Abstract.
Wells et al., "Enhanced in Vivo Delivery of Antisense Oligonucleotide to Restore Dystrophin Expression in Adult MDX Mouse Muscle," *FEBS Letters* 2003 552: 145-149.
Wenk et al., "Quantitation of MR 46000 and Mr 300000 mannose 6-phosphate receptors in human cells and tissues," *Biochem Int.*, vol. 23, No. 4, pp. 723-731 (Mar. 1991) (Abstract).
Wheway et al., "The Dystrophin Lymphocyte promoter revisited: 4.5-megabase intron, or artefact?" Neuromuscular Disorders 13(2003) 17-20.
Wilton et al., "Specific removal of the nonsense mutation from the mdx dystrophin protein mRNA using antisense oligonucleotides." Neuromuscular Disorders, 1999, vol. 9, pp. 330-338.
Wilton et al., "Antisense oligonucleotides, exon skipping and the dystrophin gene transcript," Acta Myologica XXIV:222-229 (2005).
Wilton et al., "Antisense Oligonucleotide-induced Exon Skipping Across the Human Dystrophin Gene Transcript", Molecular Therapy: The Journal of the American Society of Gene Therapy, vol. 15, No. 7, 1288-1296, Jul. 2007.
Wu et al., "Targeted Skipping of Human Dystrophin Exons in Transgenic Mouse Model Systemically for Antisense Drug Development," PLoS ONE 6(5): e19906, dob10.1371/journal. pone0019906, 2011.
Xu et al., "Potential for Pharmacology of Ryanodine Receptor/ Calcium Release Channels," Annals of the New York Academy of Sciences, 853: pp. 130-148, 1998.
Yen et al., "Sequence-specific cleavage of Huntingtin MRNA by catalytic DNA," *Animals of Neurology*, pp. 366-373, vol. 46, No. 3, 1999.
Yilmaz-Elis AS, et al., "Inhibition of IL-1 Signaling by Antisense Oligonucleotide-mediated Exon Skipping of IL-1 Receptor Accessory Protein (IL-1 RAcP)" *Molecular Therapy-Nucleic Acids* (2013) 2, e66, 8 pages.
Yin et al., "Effective Exon Skipping and Restoration of Dystrophin Expression by Peptide Nucleic Acid Antisense Oligonucleotides in mdx Mice," *Mol. Ther.*, vol. 16, No. 1, pp. 38-45 (Jan. 2008).
Yokota, et al., Efficacy of Systemic Morpholino Exon-Skipping in Duchenne Dystrophy Dogs, *Ann Neurol.*, 2009, pp. 667-76, vol. 65.
Yokota et al., "Antisense Oligo-Mediated Multiple Exon Skipping in a Dog Model of Duchenne Muscular Dystrophy," Muscle Gene Therapy: Methods and Protocols, Methods in Molecular Biology vol. 709, pp. 299-312.
Authorized Officer: Lee W. Young, International Search Report, International Application No. PCT/US10/48532, dated Jan. 26, 2011, 4 pages.
Yu M, et al., "A hairpin ribozyme inhibits expression of diverse strains of human immunodeficiency virus type 1" *Proc. Natl. Acad. Sci*. Jul. 1993; vol. 90, pp. 6340-6344.
Yu et al., "Development of an Ultrasensitive Noncompetitive Hybridization-Ligation Enzyme-Linked Immunosorbent Assay for the Determination of Phosphorothioate Oligodeoxynucleotide in Plasma," Analytical Biochemistry 304, pp. 19-25, 2002.
Zhang et al., "Efficient expression of naked DNA delivered intraarterially to limb muscles of nonhuman primates," *Hum. Gene. Ther.*, vol. 12, No. 4, pp. 427-438 (Mar. 2001) (Abstract).
Zhou et al., "Current understanding of dystrophin-related muscular dystrophy and therapeutic challenges ahead," *Chinese Medical J.*, Aug. 2006, vol. 119(16): 1381-1391.

(56) References Cited

OTHER PUBLICATIONS

Leiden University Medical Center and Prosensa BV announce New England Journal of Medicine Publication of First Successful Clinical Study with RNA-based Therapeutic PRO051 in Duchenne Muscular Dystrophy, Dec. 27, 2007.
Bionity.Com NEWS-Center, Leiden University Medical Center and Presensa B.V. Announce First Successful Clinical Study with RNA-based Therapeutic PRO051, dated Jan. 3, 2008, http://www.bionity.com/news/e76185.
Biopharmaceutiques, Merging Pharma & Biotech, Edition 48, Jan. 10, 2008. http://www.biopharmaceutiques.com/en/num, visited Jan. 11, 2008.
International Preliminary Report on Patentability and Written Opinion for PCT/EP2007/054842, mailed on Nov. 21, 2008, 8 pages.
International Search Report for PCT/EP2007/054842, mailed on Aug. 21, 2007, 3 pages.
International Search Report for PCT/NL2009/050006 dated Jul. 31, 2009.
Declaration of Dr. Adrian Krainer (submitted in Third-Party's Statement for JP Appl. No. 2002-529499, dated Oct. 29, 2010).
International Preliminary Examination Report, International Application No. PCT/NL01/00697, dated Aug. 1, 2002.
Notice of Opposition filed against EP 1 619 249 B, dated Jun. 23, 2009.
Office Action for U.S. Appl. No. 10/395,031 dated Apr. 2, 2009.
Office Action for U.S. Appl. No. 10/395,031 dated Aug. 23, 2007.
Office Action for U.S. Appl. No. 10/395,031 dated Feb. 6, 2006.
Office Action for U.S. Appl. No. 10/395,031 dated Jul. 8, 2005.
Office Action for U.S. Appl. No. 10/395,031 dated May 30, 2008.
Office Action for U.S. Appl. No. 10/395,031 dated Nov. 30, 2006.
Office Action for U.S. Appl. No. 10/395,031 dated Oct. 16, 2009.
Office Action for U.S. Appl. No. 11/233,495 dated Dec. 1, 2008.
Office Action for U.S. Appl. No. 11/233,495 dated Jun. 25, 2009.
Office Action for U.S. Appl. No. 11/233,507 dated Jun. 15, 2007.
Office Action for U.S. Appl. No. 11/233,495 dated Mar. 19, 2008.
Office Action for U.S. Appl. No. 11/233,495 dated May 29, 2009.
Office Action for U.S. Appl. No. 11/233,507 dated Nov. 12, 2008.
Office Action for U.S. Appl. No. 11/982,285 dated May 4, 2009.
Office Action for U.S. Appl. No. 11/982,285 dated Sep. 18, 2009.
Request for Opinion under Section 74(a) in relation to Patent No. EP (IK) 1 619 249B in the name of Academisch Ziekenhuis Leiden, opinion issued on Jun. 4, 2009.
Request for UK IPO Opinion (Section 74A & Rule 93) —EP(UK) 1619249 dated Mar. 9, 2009.
Third Party's Statement for Japan Appl. No. 2002-529499, dated Oct. 29, 2010.
Patent Trial and Appeal Board, *University of Western Australia* (U.S. Pat. No. 8,455,636) v. *Academisch Ziekenhuis Leiden* (U.S. Appl. No. 11/233,495); *University of Western Australia* (U.S. Pat. Nos. 7,960,541 and 7,807,816) v. *Academisch Ziekenhuis Leiden* (U.S. Appl. No. 13/550,210), Order—Oral Argument—37 C.F.R. § 41.124, 2 pages, entered Mar. 29, 2016 [Patent Interference Nos. 106,007 (RES) and 106,008 (RES)].
Patent Trial and Appeal Board, *University of Western Australia* (U.S. Pat. No. 8,455,636) v. *Academisch Ziekenhuis Leiden* (U.S. Appl. No. 11/233,495), Decision—Motions—37 C.F.R. § 41.125(a), 53 pages, entered Apr. 29, 2016 [Patent Interference No. 106,007 (RES)].
Patent Trial and Appeal Board, *University of Western Australia* (U.S. Pat. No. 8,455,636) v. *Academisch Ziekenhuis Leiden* (U.S. Appl. No. 11/233,495), Redeclaration—37 C.F.R. § 41.203(c), 2 pages, entered Apr. 29, 2016 [Patent Interference No. 106,007 (RES)].
Patent Trial and Appeal Board, *University of Western Australia* (U.S. Pat. No. 8,455,636) v. *Academisch Ziekenhuis Leiden* (U.S. Appl. No. 11/233,495), Judgment—Motions—37 C.F.R. § 41.127, 3 pages, entered Apr. 29, 2016 [Patent Interference No. 106,007 (RES)].
University of Western Australia, *University of Western Australia* v. *Academisch Ziekenhuis Leiden*, Motion of Appellant University of Western Australia to Stay Appeal Pending Appeals in Two Related Interferences, Document 4-1, 7 pages, entered May 6, 2016 [Patent Interference No. 106,013] [Civil Action No. 2016-1937].
Patent Trial and Appeal Board, *University of Western Australia* (U.S. Pat. No. 8,455,636) v. *Academisch Ziekenhuis Leiden* (U.S. Appl. No. 11/233,495), Withdrawal and Reissue of Decision on Motions, 2 pages, entered May 12, 2016 [Patent Interference No. 106,007 (RES)].
Patent Trial and Appeal Board, *University of Western Australia* (U.S. Pat. No. 8,455,636) v. *Academisch Ziekenhuis Leiden* (U.S. Appl. No. 11/233,495), Decision—Motions—37 C.F.R. § 41.125(a) (Substitute), 53 pages, entered May 12, 2016 [Patent Interference No. 106,007 (RES)].
Anonymous, "Dystrophin gene (DMD) expression inhibitor PRO-051," Prous Integrity, Mar. 8, 2012, XP002677703, Retrieved from the Internet: URL:http://integrity,thomson-pharma.com/integrity/xmlxsl/p1_prod_list.productSumaryDetails?p_entryNumber=467686 [retrieved on Jun. 12, 2012] the whole document.
Lewin, "Genes VII," Oxford University Press, Chapters 1, 5, 22: pp. 29, 126, 129, 686, 2000.
Cartegni et al., "Correction of disease-associated exon skipping by synthetic exon-specific activators," Nature Structural Biology, vol. 10, No. 2, pp. 120-125, Feb. 2003.
Chamberlain, "Dystrophin Levels Required for Genetic Correction of Duchenne Muscular Dystrophy," Basic and Applied Myology, 7(3-4): 251-255, 1997.
Grady, "Early Drug Test Shows Promise in Treating Muscular Dystrophy," International Health Tribune, Jan. 3, 2008, Health & Science, p. 9.
Beggs et al., "*Homo Sapiens* Dystrophin (DMD) Gene, Exon 55 and Partial CDS," Database GenBank [Online], GenBank Accession No. AF213440.1, Database Accession No. AF213440, Jan. 27, 2002.
Academisch Ziekenhuis Leiden, Sequences of Exon 53, Putative Ses Fragments and Oligonucleotides, Academisch Ziekenhuis Leiden, p. 1, Dec. 5, 2001.

\* cited by examiner

SEQUENCE LISTING

<160> NUMBER OF SEQ ID NOS: 535

<210> SEQ ID NO 1
<211> LENGTH: 3685
<212> TYPE: PRT
<213> ORGANISM: homo sapiens

<400> SEQUENCE: 1

Met Leu Trp Trp Glu Glu Val Glu Asp Cys Tyr Glu Arg Glu Asp Val
1               5                   10                  15

```
Gln Lys Lys Thr Phe Thr Lys Trp Val Asn Ala Gln Phe Ser Lys Phe
             20                  25                  30

Gly Lys Gln His Ile Glu Asn Leu Phe Ser Asp Leu Gln Asp Gly Arg
         35                  40                  45

Arg Leu Leu Asp Leu Leu Glu Gly Leu Thr Gly Gln Lys Leu Pro Lys
     50                  55                  60

Glu Lys Gly Ser Thr Arg Val His Ala Leu Asn Asn Val Asn Lys Ala
 65                  70                  75                  80

Leu Arg Val Leu Gln Asn Asn Asn Val Asp Leu Val Asn Ile Gly Ser
                 85                  90                  95

Thr Asp Ile Val Asp Gly Asn His Lys Leu Thr Leu Gly Leu Ile Trp
                100                 105                 110

Asn Ile Ile Leu His Trp Gln Val Lys Asn Val Met Lys Asn Ile Met
            115                 120                 125

Ala Gly Leu Gln Gln Thr Asn Ser Glu Lys Ile Leu Leu Ser Trp Val
        130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
                180                 185                 190

Thr Gln Arg Leu Glu His Ala Phe Asn Ile Ala Arg Tyr Gln Leu Gly
            195                 200                 205

Ile Glu Lys Leu Leu Asp Pro Glu Asp Val Asp Thr Thr Tyr Pro Asp
210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
```

```
            435                 440                 445
Leu Met Asp Leu Gln Asn Gln Lys Leu Lys Glu Leu Asn Asp Trp Leu
    450                 455                 460

Thr Lys Thr Glu Glu Arg Thr Arg Lys Met Glu Glu Pro Leu Gly
465                 470                 475                 480

Pro Asp Leu Glu Asp Leu Lys Arg Gln Val Gln Gln His Lys Val Leu
                485                 490                 495

Gln Glu Asp Leu Glu Gln Glu Val Arg Val Asn Ser Leu Thr His
            500                 505                 510

Met Val Val Val Asp Glu Ser Ser Gly Asp His Ala Thr Ala Ala
        515                 520                 525

Leu Glu Glu Gln Leu Lys Val Leu Gly Asp Arg Trp Ala Asn Ile Cys
    530                 535                 540

Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
                565                 570                 575

Glu Lys Glu Asp Ala Val Asn Lys Ile His Thr Thr Gly Phe Lys Asp
            580                 585                 590

Gln Asn Glu Met Leu Ser Ser Leu Gln Lys Leu Ala Val Leu Lys Ala
        595                 600                 605

Asp Leu Glu Lys Lys Lys Gln Ser Met Gly Lys Leu Tyr Ser Leu Lys
    610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
                645                 650                 655

Lys Leu Glu Lys Ser Thr Ala Gln Ile Ser Gln Ala Val Thr Thr Thr
            660                 665                 670

Gln Pro Ser Leu Thr Gln Thr Thr Val Met Glu Thr Val Thr Thr Val
        675                 680                 685

Thr Thr Arg Glu Gln Ile Leu Val Lys His Ala Gln Glu Glu Leu Pro
    690                 695                 700

Pro Pro Pro Gln Lys Lys Arg Gln Ile Thr Val Asp Ser Glu Ile
705                 710                 715                 720

Arg Lys Arg Leu Asp Val Asp Ile Thr Glu Leu His Ser Trp Ile Thr
                725                 730                 735

Arg Ser Glu Ala Val Leu Gln Ser Pro Glu Phe Ala Ile Phe Arg Lys
            740                 745                 750

Glu Gly Asn Phe Ser Asp Leu Lys Glu Lys Val Asn Ala Ile Glu Arg
        755                 760                 765

Glu Lys Ala Glu Lys Phe Arg Lys Leu Gln Asp Ala Ser Arg Ser Ala
    770                 775                 780

Gln Ala Leu Val Glu Gln Met Val Asn Glu Gly Val Asn Ala Asp Ser
785                 790                 795                 800

Ile Lys Gln Ala Ser Glu Gln Leu Asn Ser Arg Trp Ile Glu Phe Cys
                805                 810                 815

Gln Leu Leu Ser Glu Arg Leu Asn Trp Leu Glu Tyr Gln Asn Asn Ile
            820                 825                 830

Ile Ala Phe Tyr Asn Gln Leu Gln Gln Leu Glu Gln Met Thr Thr Thr
        835                 840                 845

Ala Glu Asn Trp Leu Lys Ile Gln Pro Thr Thr Pro Ser Glu Pro Thr
    850                 855                 860
```

```
Ala Ile Lys Ser Gln Leu Lys Ile Cys Lys Asp Glu Val Asn Arg Leu
865                 870                 875                 880

Ser Gly Leu Gln Pro Gln Ile Glu Arg Leu Lys Ile Gln Ser Ile Ala
                885                 890                 895

Leu Lys Glu Lys Gly Gln Gly Pro Met Phe Leu Asp Ala Asp Phe Val
            900                 905                 910

Ala Phe Thr Asn His Phe Lys Gln Val Phe Ser Asp Val Gln Ala Arg
        915                 920                 925

Glu Lys Glu Leu Gln Thr Ile Phe Asp Thr Leu Pro Pro Met Arg Tyr
    930                 935                 940

Gln Glu Thr Met Ser Ala Ile Arg Thr Trp Val Gln Asn Ser Glu Thr
945                 950                 955                 960

Lys Leu Ser Ile Pro Gln Leu Ser Val Thr Asp Tyr Glu Ile Met Glu
                965                 970                 975

Gln Arg Leu Gly Glu Leu Gln Ala Leu Gln Ser Ser Leu Gln Glu Gln
            980                 985                 990

Gln Ser Gly Leu Tyr Tyr Leu Ser Thr Thr Val Lys Glu Met Ser Lys
        995                 1000                1005

Lys Ala Pro Ser Glu Ile Ser Arg Lys Tyr Gln Ser Glu Phe Glu
    1010                1015                1020

Glu Ile Glu Gly Arg Trp Lys Lys Leu Ser Ser Gln Leu Val Glu
    1025                1030                1035

His Cys Gln Lys Leu Glu Glu Gln Met Asn Lys Leu Arg Lys Ile
    1040                1045                1050

Gln Asn His Ile Gln Thr Leu Lys Lys Trp Met Ala Glu Val Asp
    1055                1060                1065

Val Phe Leu Lys Glu Glu Trp Pro Ala Leu Gly Asp Ser Glu Ile
    1070                1075                1080

Leu Lys Lys Gln Leu Lys Gln Cys Arg Leu Leu Val Ser Asp Ile
    1085                1090                1095

Gln Thr Ile Gln Pro Ser Leu Asn Ser Val Asn Glu Gly Gly Gln
    1100                1105                1110

Lys Ile Lys Asn Glu Ala Glu Pro Glu Phe Ala Ser Arg Leu Glu
    1115                1120                1125

Thr Glu Leu Lys Glu Leu Asn Thr Gln Trp Asp His Met Cys Gln
    1130                1135                1140

Gln Val Tyr Ala Arg Lys Glu Ala Leu Lys Gly Gly Leu Glu Lys
    1145                1150                1155

Thr Val Ser Leu Gln Lys Asp Leu Ser Glu Met His Glu Trp Met
    1160                1165                1170

Thr Gln Ala Glu Glu Glu Tyr Leu Glu Arg Asp Phe Glu Tyr Lys
    1175                1180                1185

Thr Pro Asp Glu Leu Gln Lys Ala Val Glu Glu Met Lys Arg Ala
    1190                1195                1200

Lys Glu Glu Ala Gln Gln Lys Glu Ala Lys Val Lys Leu Leu Thr
    1205                1210                1215

Glu Ser Val Asn Ser Val Ile Ala Gln Ala Pro Pro Val Ala Gln
    1220                1225                1230

Glu Ala Leu Lys Lys Glu Leu Glu Thr Leu Thr Thr Asn Tyr Gln
    1235                1240                1245

Trp Leu Cys Thr Arg Leu Asn Gly Lys Cys Lys Thr Leu Glu Glu
    1250                1255                1260
```

```
Val Trp Ala Cys Trp His Glu Leu Leu Ser Tyr Leu Glu Lys Ala
1265                1270                1275

Asn Lys Trp Leu Asn Glu Val Glu Phe Lys Leu Lys Thr Thr Glu
1280                1285                1290

Asn Ile Pro Gly Gly Ala Glu Glu Ile Ser Glu Val Leu Asp Ser
1295                1300                1305

Leu Glu Asn Leu Met Arg His Ser Glu Asp Asn Pro Asn Gln Ile
1310                1315                1320

Arg Ile Leu Ala Gln Thr Leu Thr Asp Gly Gly Val Met Asp Glu
1325                1330                1335

Leu Ile Asn Glu Glu Leu Glu Thr Phe Asn Ser Arg Trp Arg Glu
1340                1345                1350

Leu His Glu Glu Ala Val Arg Arg Gln Lys Leu Leu Glu Gln Ser
1355                1360                1365

Ile Gln Ser Ala Gln Glu Thr Glu Lys Ser Leu His Leu Ile Gln
1370                1375                1380

Glu Ser Leu Thr Phe Ile Asp Lys Gln Leu Ala Ala Tyr Ile Ala
1385                1390                1395

Asp Lys Val Asp Ala Ala Gln Met Pro Gln Glu Ala Gln Lys Ile
1400                1405                1410

Gln Ser Asp Leu Thr Ser His Glu Ile Ser Leu Glu Glu Met Lys
1415                1420                1425

Lys His Asn Gln Gly Lys Glu Ala Ala Gln Arg Val Leu Ser Gln
1430                1435                1440

Ile Asp Val Ala Gln Lys Lys Leu Gln Asp Val Ser Met Lys Phe
1445                1450                1455

Arg Leu Phe Gln Lys Pro Ala Asn Phe Glu Gln Arg Leu Gln Glu
1460                1465                1470

Ser Lys Met Ile Leu Asp Glu Val Lys Met His Leu Pro Ala Leu
1475                1480                1485

Glu Thr Lys Ser Val Glu Gln Glu Val Val Gln Ser Gln Leu Asn
1490                1495                1500

His Cys Val Asn Leu Tyr Lys Ser Leu Ser Glu Val Lys Ser Glu
1505                1510                1515

Val Glu Met Val Ile Lys Thr Gly Arg Gln Ile Val Gln Lys Lys
1520                1525                1530

Gln Thr Glu Asn Pro Lys Glu Leu Asp Glu Arg Val Thr Ala Leu
1535                1540                1545

Lys Leu His Tyr Asn Glu Leu Gly Ala Lys Val Thr Glu Arg Lys
1550                1555                1560

Gln Gln Leu Glu Lys Cys Leu Lys Leu Ser Arg Lys Met Arg Lys
1565                1570                1575

Glu Met Asn Val Leu Thr Glu Trp Leu Ala Ala Thr Asp Met Glu
1580                1585                1590

Leu Thr Lys Arg Ser Ala Val Glu Gly Met Pro Ser Asn Leu Asp
1595                1600                1605

Ser Glu Val Ala Trp Gly Lys Ala Thr Gln Lys Glu Ile Glu Lys
1610                1615                1620

Gln Lys Val His Leu Lys Ser Ile Thr Glu Val Gly Glu Ala Leu
1625                1630                1635

Lys Thr Val Leu Gly Lys Lys Glu Thr Leu Val Glu Asp Lys Leu
1640                1645                1650

Ser Leu Leu Asn Ser Asn Trp Ile Ala Val Thr Ser Arg Ala Glu
```

```
                    1655                    1660                    1665

Glu  Trp  Leu  Asn  Leu  Leu  Leu  Glu  Tyr  Gln  Lys  His  Met  Glu  Thr
     1670                    1675                    1680

Phe  Asp  Gln  Asn  Val  Asp  His  Ile  Thr  Lys  Trp  Ile  Ile  Gln  Ala
     1685                    1690                    1695

Asp  Thr  Leu  Leu  Asp  Glu  Ser  Glu  Lys  Lys  Pro  Gln  Gln  Lys
     1700                    1705                    1710

Glu  Asp  Val  Leu  Lys  Arg  Leu  Lys  Ala  Glu  Leu  Asn  Asp  Ile  Arg
     1715                    1720                    1725

Pro  Lys  Val  Asp  Ser  Thr  Arg  Asp  Gln  Ala  Ala  Asn  Leu  Met  Ala
     1730                    1735                    1740

Asn  Arg  Gly  Asp  His  Cys  Arg  Lys  Leu  Val  Glu  Pro  Gln  Ile  Ser
     1745                    1750                    1755

Glu  Leu  Asn  His  Arg  Phe  Ala  Ala  Ile  Ser  His  Arg  Ile  Lys  Thr
     1760                    1765                    1770

Gly  Lys  Ala  Ser  Ile  Pro  Leu  Lys  Glu  Leu  Glu  Gln  Phe  Asn  Ser
     1775                    1780                    1785

Asp  Ile  Gln  Lys  Leu  Leu  Glu  Pro  Leu  Glu  Ala  Glu  Ile  Gln  Gln
     1790                    1795                    1800

Gly  Val  Asn  Leu  Lys  Glu  Glu  Asp  Phe  Asn  Lys  Asp  Met  Asn  Glu
     1805                    1810                    1815

Asp  Asn  Glu  Gly  Thr  Val  Lys  Glu  Leu  Leu  Gln  Arg  Gly  Asp  Asn
     1820                    1825                    1830

Leu  Gln  Gln  Arg  Ile  Thr  Asp  Glu  Arg  Lys  Arg  Glu  Glu  Ile  Lys
     1835                    1840                    1845

Ile  Lys  Gln  Gln  Leu  Leu  Gln  Thr  Lys  His  Asn  Ala  Leu  Lys  Asp
     1850                    1855                    1860

Leu  Arg  Ser  Gln  Arg  Arg  Lys  Lys  Ala  Leu  Glu  Ile  Ser  His  Gln
     1865                    1870                    1875

Trp  Tyr  Gln  Tyr  Lys  Arg  Gln  Ala  Asp  Asp  Leu  Leu  Lys  Cys  Leu
     1880                    1885                    1890

Asp  Asp  Ile  Glu  Lys  Lys  Leu  Ala  Ser  Leu  Pro  Glu  Pro  Arg  Asp
     1895                    1900                    1905

Glu  Arg  Lys  Ile  Lys  Glu  Ile  Asp  Arg  Glu  Leu  Gln  Lys  Lys  Lys
     1910                    1915                    1920

Glu  Glu  Leu  Asn  Ala  Val  Arg  Arg  Gln  Ala  Glu  Gly  Leu  Ser  Glu
     1925                    1930                    1935

Asp  Gly  Ala  Ala  Met  Ala  Val  Glu  Pro  Thr  Gln  Ile  Gln  Leu  Ser
     1940                    1945                    1950

Lys  Arg  Trp  Arg  Glu  Ile  Glu  Ser  Lys  Phe  Ala  Gln  Phe  Arg  Arg
     1955                    1960                    1965

Leu  Asn  Phe  Ala  Gln  Ile  His  Thr  Val  Arg  Glu  Glu  Thr  Met  Met
     1970                    1975                    1980

Val  Met  Thr  Glu  Asp  Met  Pro  Leu  Glu  Ile  Ser  Tyr  Val  Pro  Ser
     1985                    1990                    1995

Thr  Tyr  Leu  Thr  Glu  Ile  Thr  His  Val  Ser  Gln  Ala  Leu  Leu  Glu
     2000                    2005                    2010

Val  Glu  Gln  Leu  Leu  Asn  Ala  Pro  Asp  Leu  Cys  Ala  Lys  Asp  Phe
     2015                    2020                    2025

Glu  Asp  Leu  Phe  Lys  Gln  Glu  Glu  Ser  Leu  Lys  Asn  Ile  Lys  Asp
     2030                    2035                    2040

Ser  Leu  Gln  Gln  Ser  Ser  Gly  Arg  Ile  Asp  Ile  Ile  His  Ser  Lys
     2045                    2050                    2055
```

-continued

Lys Thr Ala Ala Leu Gln Ser Ala Thr Pro Val Glu Arg Val Lys
2060                2065                2070

Leu Gln Glu Ala Leu Ser Gln Leu Asp Phe Gln Trp Glu Lys Val
2075                2080                2085

Asn Lys Met Tyr Lys Asp Arg Gln Gly Arg Phe Asp Arg Ser Val
2090                2095                2100

Glu Lys Trp Arg Arg Phe His Tyr Asp Ile Lys Ile Phe Asn Gln
2105                2110                2115

Trp Leu Thr Glu Ala Glu Gln Phe Leu Arg Lys Thr Gln Ile Pro
2120                2125                2130

Glu Asn Trp Glu His Ala Lys Tyr Lys Trp Tyr Leu Lys Glu Leu
2135                2140                2145

Gln Asp Gly Ile Gly Gln Arg Gln Thr Val Val Arg Thr Leu Asn
2150                2155                2160

Ala Thr Gly Glu Glu Ile Ile Gln Gln Ser Ser Lys Thr Asp Ala
2165                2170                2175

Ser Ile Leu Gln Glu Lys Leu Gly Ser Leu Asn Leu Arg Trp Gln
2180                2185                2190

Glu Val Cys Lys Gln Leu Ser Asp Arg Lys Lys Arg Leu Glu Glu
2195                2200                2205

Gln Lys Asn Ile Leu Ser Glu Phe Gln Arg Asp Leu Asn Glu Phe
2210                2215                2220

Val Leu Trp Leu Glu Glu Ala Asp Asn Ile Ala Ser Ile Pro Leu
2225                2230                2235

Glu Pro Gly Lys Glu Gln Gln Leu Lys Glu Lys Leu Glu Gln Val
2240                2245                2250

Lys Leu Leu Val Glu Glu Leu Pro Leu Arg Gln Gly Ile Leu Lys
2255                2260                2265

Gln Leu Asn Glu Thr Gly Gly Pro Val Leu Val Ser Ala Pro Ile
2270                2275                2280

Ser Pro Glu Glu Gln Asp Lys Leu Glu Asn Lys Leu Lys Gln Thr
2285                2290                2295

Asn Leu Gln Trp Ile Lys Val Ser Arg Ala Leu Pro Glu Lys Gln
2300                2305                2310

Gly Glu Ile Glu Ala Gln Ile Lys Asp Leu Gly Gln Leu Glu Lys
2315                2320                2325

Lys Leu Glu Asp Leu Glu Glu Gln Leu Asn His Leu Leu Leu Trp
2330                2335                2340

Leu Ser Pro Ile Arg Asn Gln Leu Glu Ile Tyr Asn Gln Pro Asn
2345                2350                2355

Gln Glu Gly Pro Phe Asp Val Gln Glu Thr Glu Ile Ala Val Gln
2360                2365                2370

Ala Lys Gln Pro Asp Val Glu Glu Ile Leu Ser Lys Gly Gln His
2375                2380                2385

Leu Tyr Lys Glu Lys Pro Ala Thr Gln Pro Val Lys Arg Lys Leu
2390                2395                2400

Glu Asp Leu Ser Ser Glu Trp Lys Ala Val Asn Arg Leu Leu Gln
2405                2410                2415

Glu Leu Arg Ala Lys Gln Pro Asp Leu Ala Pro Gly Leu Thr Thr
2420                2425                2430

Ile Gly Ala Ser Pro Thr Gln Thr Val Thr Leu Val Thr Gln Pro
2435                2440                2445

-continued

Val Val Thr Lys Glu Thr Ala Ile Ser Lys Leu Glu Met Pro Ser
    2450            2455            2460

Ser Leu Met Leu Glu Val Pro Ala Leu Ala Asp Phe Asn Arg Ala
2465            2470            2475

Trp Thr Glu Leu Thr Asp Trp Leu Ser Leu Leu Asp Gln Val Ile
    2480            2485            2490

Lys Ser Gln Arg Val Met Val Gly Asp Leu Glu Asp Ile Asn Glu
2495            2500            2505

Met Ile Ile Lys Gln Lys Ala Thr Met Gln Asp Leu Glu Gln Arg
    2510            2515            2520

Arg Pro Gln Leu Glu Glu Leu Ile Thr Ala Ala Gln Asn Leu Lys
2525            2530            2535

Asn Lys Thr Ser Asn Gln Glu Ala Arg Thr Ile Ile Thr Asp Arg
    2540            2545            2550

Ile Glu Arg Ile Gln Asn Gln Trp Asp Glu Val Gln Glu His Leu
2555            2560            2565

Gln Asn Arg Arg Gln Gln Leu Asn Glu Met Leu Lys Asp Ser Thr
    2570            2575            2580

Gln Trp Leu Glu Ala Lys Glu Glu Ala Glu Gln Val Leu Gly Gln
2585            2590            2595

Ala Arg Ala Lys Leu Glu Ser Trp Lys Glu Gly Pro Tyr Thr Val
    2600            2605            2610

Asp Ala Ile Gln Lys Lys Ile Thr Glu Thr Lys Gln Leu Ala Lys
2615            2620            2625

Asp Leu Arg Gln Trp Gln Thr Asn Val Asp Val Ala Asn Asp Leu
    2630            2635            2640

Ala Leu Lys Leu Leu Arg Asp Tyr Ser Ala Asp Asp Thr Arg Lys
2645            2650            2655

Val His Met Ile Thr Glu Asn Ile Asn Ala Ser Trp Arg Ser Ile
    2660            2665            2670

His Lys Arg Val Ser Glu Arg Glu Ala Ala Leu Glu Glu Thr His
2675            2680            2685

Arg Leu Leu Gln Gln Phe Pro Leu Asp Leu Glu Lys Phe Leu Ala
    2690            2695            2700

Trp Leu Thr Glu Ala Glu Thr Thr Ala Asn Val Leu Gln Asp Ala
2705            2710            2715

Thr Arg Lys Glu Arg Leu Leu Glu Asp Ser Lys Gly Val Lys Glu
    2720            2725            2730

Leu Met Lys Gln Trp Gln Asp Leu Gln Gly Glu Ile Glu Ala His
2735            2740            2745

Thr Asp Val Tyr His Asn Leu Asp Glu Asn Ser Gln Lys Ile Leu
    2750            2755            2760

Arg Ser Leu Glu Gly Ser Asp Asp Ala Val Leu Leu Gln Arg Arg
2765            2770            2775

Leu Asp Asn Met Asn Phe Lys Trp Ser Glu Leu Arg Lys Lys Ser
    2780            2785            2790

Leu Asn Ile Arg Ser His Leu Glu Ala Ser Ser Asp Gln Trp Lys
2795            2800            2805

Arg Leu His Leu Ser Leu Gln Glu Leu Leu Val Trp Leu Gln Leu
    2810            2815            2820

Lys Asp Asp Glu Leu Ser Arg Gln Ala Pro Ile Gly Gly Asp Phe
2825            2830            2835

Pro Ala Val Gln Lys Gln Asn Asp Val His Arg Ala Phe Lys Arg

-continued

```
            2840                2845               2850

Glu Leu Lys Thr Lys Glu Pro Val Ile Met Ser Thr Leu Glu Thr
            2855                2860               2865

Val Arg Ile Phe Leu Thr Glu Gln Pro Leu Glu Gly Leu Glu Lys
            2870                2875               2880

Leu Tyr Gln Glu Pro Arg Glu Leu Pro Pro Glu Glu Arg Ala Gln
            2885                2890               2895

Asn Val Thr Arg Leu Leu Arg Lys Gln Ala Glu Glu Val Asn Thr
            2900                2905               2910

Glu Trp Glu Lys Leu Asn Leu His Ser Ala Asp Trp Gln Arg Lys
            2915                2920               2925

Ile Asp Glu Thr Leu Glu Arg Leu Gln Glu Leu Gln Glu Ala Thr
            2930                2935               2940

Asp Glu Leu Asp Leu Lys Leu Arg Gln Ala Glu Val Ile Lys Gly
            2945                2950               2955

Ser Trp Gln Pro Val Gly Asp Leu Leu Ile Asp Ser Leu Gln Asp
            2960                2965               2970

His Leu Glu Lys Val Lys Ala Leu Arg Gly Glu Ile Ala Pro Leu
            2975                2980               2985

Lys Glu Asn Val Ser His Val Asn Asp Leu Ala Arg Gln Leu Thr
            2990                2995               3000

Thr Leu Gly Ile Gln Leu Ser Pro Tyr Asn Leu Ser Thr Leu Glu
            3005                3010               3015

Asp Leu Asn Thr Arg Trp Lys Leu Leu Gln Val Ala Val Glu Asp
            3020                3025               3030

Arg Val Arg Gln Leu His Glu Ala His Arg Asp Phe Gly Pro Ala
            3035                3040               3045

Ser Gln His Phe Leu Ser Thr Ser Val Gln Gly Pro Trp Glu Arg
            3050                3055               3060

Ala Ile Ser Pro Asn Lys Val Pro Tyr Tyr Ile Asn His Glu Thr
            3065                3070               3075

Gln Thr Thr Cys Trp Asp His Pro Lys Met Thr Glu Leu Tyr Gln
            3080                3085               3090

Ser Leu Ala Asp Leu Asn Asn Val Arg Phe Ser Ala Tyr Arg Thr
            3095                3100               3105

Ala Met Lys Leu Arg Arg Leu Gln Lys Ala Leu Cys Leu Asp Leu
            3110                3115               3120

Leu Ser Leu Ser Ala Ala Cys Asp Ala Leu Asp Gln His Asn Leu
            3125                3130               3135

Lys Gln Asn Asp Gln Pro Met Asp Ile Leu Gln Ile Ile Asn Cys
            3140                3145               3150

Leu Thr Thr Ile Tyr Asp Arg Leu Glu Gln Glu His Asn Asn Leu
            3155                3160               3165

Val Asn Val Pro Leu Cys Val Asp Met Cys Leu Asn Trp Leu Leu
            3170                3175               3180

Asn Val Tyr Asp Thr Gly Arg Thr Gly Arg Ile Arg Val Leu Ser
            3185                3190               3195

Phe Lys Thr Gly Ile Ile Ser Leu Cys Lys Ala His Leu Glu Asp
            3200                3205               3210

Lys Tyr Arg Tyr Leu Phe Lys Gln Val Ala Ser Ser Thr Gly Phe
            3215                3220               3225

Cys Asp Gln Arg Arg Leu Gly Leu Leu Leu His Asp Ser Ile Gln
            3230                3235               3240
```

```
Ile Pro Arg Gln Leu Gly Glu Val Ala Ser Phe Gly Gly Ser Asn
3245                3250                3255

Ile Glu Pro Ser Val Arg Ser Cys Phe Gln Phe Ala Asn Asn Lys
3260                3265                3270

Pro Glu Ile Glu Ala Ala Leu Phe Leu Asp Trp Met Arg Leu Glu
3275                3280                3285

Pro Gln Ser Met Val Trp Leu Pro Val Leu His Arg Val Ala Ala
3290                3295                3300

Ala Glu Thr Ala Lys His Gln Ala Lys Cys Asn Ile Cys Lys Glu
3305                3310                3315

Cys Pro Ile Ile Gly Phe Arg Tyr Arg Ser Leu Lys His Phe Asn
3320                3325                3330

Tyr Asp Ile Cys Gln Ser Cys Phe Phe Ser Gly Arg Val Ala Lys
3335                3340                3345

Gly His Lys Met His Tyr Pro Met Val Glu Tyr Cys Thr Pro Thr
3350                3355                3360

Thr Ser Gly Glu Asp Val Arg Asp Phe Ala Lys Val Leu Lys Asn
3365                3370                3375

Lys Phe Arg Thr Lys Arg Tyr Phe Ala Lys His Pro Arg Met Gly
3380                3385                3390

Tyr Leu Pro Val Gln Thr Val Leu Glu Gly Asp Asn Met Glu Thr
3395                3400                3405

Pro Val Thr Leu Ile Asn Phe Trp Pro Val Asp Ser Ala Pro Ala
3410                3415                3420

Ser Ser Pro Gln Leu Ser His Asp Asp Thr His Ser Arg Ile Glu
3425                3430                3435

His Tyr Ala Ser Arg Leu Ala Glu Met Glu Asn Ser Asn Gly Ser
3440                3445                3450

Tyr Leu Asn Asp Ser Ile Ser Pro Asn Glu Ser Ile Asp Asp Glu
3455                3460                3465

His Leu Leu Ile Gln His Tyr Cys Gln Ser Leu Asn Gln Asp Ser
3470                3475                3480

Pro Leu Ser Gln Pro Arg Ser Pro Ala Gln Ile Leu Ile Ser Leu
3485                3490                3495

Glu Ser Glu Glu Arg Gly Glu Leu Glu Arg Ile Leu Ala Asp Leu
3500                3505                3510

Glu Glu Glu Asn Arg Asn Leu Gln Ala Glu Tyr Asp Arg Leu Lys
3515                3520                3525

Gln Gln His Glu His Lys Gly Leu Ser Pro Leu Pro Ser Pro Pro
3530                3535                3540

Glu Met Met Pro Thr Ser Pro Gln Ser Pro Arg Asp Ala Glu Leu
3545                3550                3555

Ile Ala Glu Ala Lys Leu Leu Arg Gln His Lys Gly Arg Leu Glu
3560                3565                3570

Ala Arg Met Gln Ile Leu Glu Asp His Asn Lys Gln Leu Glu Ser
3575                3580                3585

Gln Leu His Arg Leu Arg Gln Leu Leu Glu Gln Pro Gln Ala Glu
3590                3595                3600

Ala Lys Val Asn Gly Thr Thr Val Ser Ser Pro Ser Thr Ser Leu
3605                3610                3615

Gln Arg Ser Asp Ser Ser Gln Pro Met Leu Leu Arg Val Val Gly
3620                3625                3630
```

```
Ser Gln Thr Ser Asp Ser Met Gly Glu Glu Asp Leu Leu Ser Pro
    3635                3640                3645

Pro Gln Asp Thr Ser Thr Gly Leu Glu Glu Val Met Glu Gln Leu
    3650                3655                3660

Asn Asn Ser Phe Pro Ser Ser Arg Gly Arg Asn Thr Pro Gly Lys
    3665                3670                3675

Pro Met Arg Glu Asp Thr Met
    3680                3685

<210> SEQ ID NO 2
<211> LENGTH: 83
<212> TYPE: RNA
<213> ORGANISM: artificial
<220> FEATURE:
<223> OTHER INFORMATION: oligonucleotide

<400> SEQUENCE: 2
agauagucua caacaaagcu caggucggau ugacauuauu cauagcaaga agacagcagc      60
auugcaaagu gcaacgccug ugg                                             83

<210> SEQ ID NO 3
<211> LENGTH: 76
<212> TYPE: RNA
<213> ORGANISM: artificial
<220> FEATURE:
<223> OTHER INFORMATION: oligonucleotide

<400> SEQUENCE: 3
uuaugguugg aggaagcaga uaacauugcu aguaucccac uugaaccugg aaaagagcag      60
caacuaaaag aaaagc                                                     76

<210> SEQ ID NO 4
<211> LENGTH: 72
<212> TYPE: RNA
<213> ORGANISM: artificial
<220> FEATURE:
<223> OTHER INFORMATION: oligonucleotide

<400> SEQUENCE: 4
ggcgguaaac cguuuacuuc aagagcugag ggcaaagcag ccugaccuag cuccuggacu      60
gaccacuauu gg                                                         72

<210> SEQ ID NO 5
<211> LENGTH: 99
<212> TYPE: RNA
<213> ORGANISM: artificial
<220> FEATURE:
<223> OTHER INFORMATION: oligonucleotide

<400> SEQUENCE: 5
cuccuacuca gacuguuacu cuggugacac aaccuguggu uacuaaggaa acugccaucu      60
ccaaacuaga aaugccaucu uccuugaugu uggagguac                            99

<210> SEQ ID NO 6
<211> LENGTH: 90
<212> TYPE: RNA
<213> ORGANISM: artificial
<220> FEATURE:
<223> OTHER INFORMATION: oligonucleotide

<400> SEQUENCE: 6
augcaggauu uggaacagag gcgucoccag uuggaagaac ucauuaccgc ugcccaaaau      60
```
uugaaaaaca agaccagcaa ucaagaggcu                                          90

<210> SEQ ID NO 7
<211> LENGTH: 72
<212> TYPE: RNA
<213> ORGANISM: artificial
<220> FEATURE:
<223> OTHER INFORMATION: oligonucleotide

<400> SEQUENCE: 7
aaauguuaaa ggauucaaca caauggcugg aagcuaagga agaagcugag caggucuuag        60
gacaggccag ag                                                             72

<210> SEQ ID NO 8
<211> LENGTH: 25
<212> TYPE: RNA
<213> ORGANISM: artificial
<220> FEATURE:
<223> OTHER INFORMATION: oligonucleotide

<400> SEQUENCE: 8
ccacaggcgu ugcacuuugc aaugc                                               25

<210> SEQ ID NO 9
<211> LENGTH: 25
<212> TYPE: RNA
<213> ORGANISM: artificial
<220> FEATURE:
<223> OTHER INFORMATION: oligonucleotide

<400> SEQUENCE: 9
cacaggcguu gcacuuugca augcu                                               25

<210> SEQ ID NO 10
<211> LENGTH: 25
<212> TYPE: RNA
<213> ORGANISM: artificial
<220> FEATURE:
<223> OTHER INFORMATION: oligonucleotide

<400> SEQUENCE: 10
acaggcguug cacuuugcaa ugcug                                               25

<210> SEQ ID NO 11
<211> LENGTH: 25
<212> TYPE: RNA
<213> ORGANISM: artificial
<220> FEATURE:
<223> OTHER INFORMATION: oligonucleotide

<400> SEQUENCE: 11
caggcguugc acuuugcaau gcugc                                               25

<210> SEQ ID NO 12
<211> LENGTH: 25
<212> TYPE: RNA
<213> ORGANISM: artificial
<220> FEATURE:
<223> OTHER INFORMATION: oligonucleotide

<400> SEQUENCE: 12
aggcguugca cuuugcaaug cugcu                                               25

<210> SEQ ID NO 13

```
<211> LENGTH: 25
<212> TYPE: RNA
<213> ORGANISM: artificial
<220> FEATURE:
<223> OTHER INFORMATION: oligonucleotide

<400> SEQUENCE: 13
ggcguugcac uuugcaaugc ugcug                                 25

<210> SEQ ID NO 14
<211> LENGTH: 25
<212> TYPE: RNA
<213> ORGANISM: artificial
<220> FEATURE:
<223> OTHER INFORMATION: oligonucleotide

<400> SEQUENCE: 14
gcguugcacu uugcaaugcu gcugu                                 25

<210> SEQ ID NO 15
<211> LENGTH: 25
<212> TYPE: RNA
<213> ORGANISM: Artificial
<220> FEATURE:
<223> OTHER INFORMATION: oligonucleotide

<400> SEQUENCE: 15
cguugcacuu ugcaaugcug cuguc                                 25

<210> SEQ ID NO 16
<211> LENGTH: 23
<212> TYPE: RNA
<213> ORGANISM: artificial
<220> FEATURE:
<223> OTHER INFORMATION: oligonucleotide

<400> SEQUENCE: 16
cguugcacuu ugcaaugcug cug                                   23

<210> SEQ ID NO 17
<211> LENGTH: 25
<212> TYPE: RNA
<213> ORGANISM: artificial
<220> FEATURE:
<223> OTHER INFORMATION: oligonucleotide

<400> SEQUENCE: 17
guugcacuuu gcaaugcugc ugucu                                 25

<210> SEQ ID NO 18
<211> LENGTH: 25
<212> TYPE: RNA
<213> ORGANISM: artificial
<220> FEATURE:
<223> OTHER INFORMATION: oligonucleotide

<400> SEQUENCE: 18
uugcacuuug caaugcugcu gucuu                                 25

<210> SEQ ID NO 19
<211> LENGTH: 25
<212> TYPE: RNA
<213> ORGANISM: artificial
<220> FEATURE:
<223> OTHER INFORMATION: oligonucleotide

<400> SEQUENCE: 19
```

-continued ugcacuuugc aaugcugcug ucuuc                     25

<210> SEQ ID NO 20
<211> LENGTH: 25
<212> TYPE: RNA
<213> ORGANISM: artificial
<220> FEATURE:
<223> OTHER INFORMATION: oligonucleotide

<400> SEQUENCE: 20
gcacuuugca augcugcugu cuucu                     25

<210> SEQ ID NO 21
<211> LENGTH: 25
<212> TYPE: RNA
<213> ORGANISM: artificial
<220> FEATURE:
<223> OTHER INFORMATION: oligonucleotide

<400> SEQUENCE: 21
cacuuugcaa ugcugcuguc uucuu                     25

<210> SEQ ID NO 22
<211> LENGTH: 25
<212> TYPE: RNA
<213> ORGANISM: artificial
<220> FEATURE:
<223> OTHER INFORMATION: oligonucleotide

<400> SEQUENCE: 22
acuuugcaau gcugcugucu cuug                      25

<210> SEQ ID NO 23
<211> LENGTH: 25
<212> TYPE: RNA
<213> ORGANISM: artificial
<220> FEATURE:
<223> OTHER INFORMATION: oligonucleotide

<400> SEQUENCE: 23
cuuugcaaug cugcugucuu cuugc                     25

<210> SEQ ID NO 24
<211> LENGTH: 25
<212> TYPE: RNA
<213> ORGANISM: artificial
<220> FEATURE:
<223> OTHER INFORMATION: oligonucleotide

<400> SEQUENCE: 24
uuugcaaugc ugcugucuuc uugcu                     25

<210> SEQ ID NO 25
<211> LENGTH: 25
<212> TYPE: RNA
<213> ORGANISM: artificial
<220> FEATURE:
<223> OTHER INFORMATION: oligonucleotide

<400> SEQUENCE: 25
uugcaaugcu gcugucuucu ugcua                     25

<210> SEQ ID NO 26
<211> LENGTH: 25
<212> TYPE: RNA

```
<213> ORGANISM: artificial
<220> FEATURE:
<223> OTHER INFORMATION: oligonucleotide

<400> SEQUENCE: 26
ugcaaugcug cugucuucuu gcuau                                         25

<210> SEQ ID NO 27
<211> LENGTH: 25
<212> TYPE: RNA
<213> ORGANISM: artificial
<220> FEATURE:
<223> OTHER INFORMATION: oligonucleotide

<400> SEQUENCE: 27
gcaaugcugc ugucuucuug cuaug                                         25

<210> SEQ ID NO 28
<211> LENGTH: 25
<212> TYPE: RNA
<213> ORGANISM: artificial
<220> FEATURE:
<223> OTHER INFORMATION: oligonucleotide

<400> SEQUENCE: 28
caaugcugcu gucuucuugc uauga                                         25

<210> SEQ ID NO 29
<211> LENGTH: 25
<212> TYPE: RNA
<213> ORGANISM: artificial
<220> FEATURE:
<223> OTHER INFORMATION: olignucleotide

<400> SEQUENCE: 29
aaugcugcug ucuucuugcu augaa                                         25

<210> SEQ ID NO 30
<211> LENGTH: 25
<212> TYPE: RNA
<213> ORGANISM: artificial
<220> FEATURE:
<223> OTHER INFORMATION: oligonucleotide

<400> SEQUENCE: 30
augcugcugu cuucuugcua ugaau                                         25

<210> SEQ ID NO 31
<211> LENGTH: 25
<212> TYPE: RNA
<213> ORGANISM: artificial
<220> FEATURE:
<223> OTHER INFORMATION: oligonucleotide

<400> SEQUENCE: 31
ugcugcuguc uucuugcuau gaaua                                         25

<210> SEQ ID NO 32
<211> LENGTH: 25
<212> TYPE: RNA
<213> ORGANISM: artificial
<220> FEATURE:
<223> OTHER INFORMATION: oligonucleotide

<400> SEQUENCE: 32
gcugcugucu ucuugcuaug aauaa                                         25
```

<210> SEQ ID NO 33
<211> LENGTH: 25
<212> TYPE: RNA
<213> ORGANISM: artificial
<220> FEATURE:
<223> OTHER INFORMATION: oligonucleotide

<400> SEQUENCE: 33
cugcugucuu cuugcauga auaau                                          25

<210> SEQ ID NO 34
<211> LENGTH: 25
<212> TYPE: RNA
<213> ORGANISM: artificial
<220> FEATURE:
<223> OTHER INFORMATION: oligonucleotide

<400> SEQUENCE: 34
ugcugucuuc uugcaugaa uaaug                                          25

<210> SEQ ID NO 35
<211> LENGTH: 25
<212> TYPE: RNA
<213> ORGANISM: artificial
<220> FEATURE:
<223> OTHER INFORMATION: oligonucleotide

<400> SEQUENCE: 35
gcugucuucu ugcaugaau aaugu                                          25

<210> SEQ ID NO 36
<211> LENGTH: 25
<212> TYPE: RNA
<213> ORGANISM: artificial
<220> FEATURE:
<223> OTHER INFORMATION: oligonucleotide

<400> SEQUENCE: 36
cugucuucuu gcaugaaua auguc                                          25

<210> SEQ ID NO 37
<211> LENGTH: 25
<212> TYPE: RNA
<213> ORGANISM: artificial
<220> FEATURE:
<223> OTHER INFORMATION: oligonucleotide

<400> SEQUENCE: 37
ugucuucuug caugaauaa uguca                                          25

<210> SEQ ID NO 38
<211> LENGTH: 25
<212> TYPE: RNA
<213> ORGANISM: artificial
<220> FEATURE:
<223> OTHER INFORMATION: oligonucleotide

<400> SEQUENCE: 38
gucuucuugc augaauaau gucaa                                          25

<210> SEQ ID NO 39
<211> LENGTH: 25
<212> TYPE: RNA
<213> ORGANISM: artificial
<220> FEATURE:

<223> OTHER INFORMATION: oligonucleotide

<400> SEQUENCE: 39
ucuucuugcu augaauaaug ucaau                                              25

<210> SEQ ID NO 40
<211> LENGTH: 25
<212> TYPE: RNA
<213> ORGANISM: artificial
<220> FEATURE:
<223> OTHER INFORMATION: oligonucleotide

<400> SEQUENCE: 40
cuucuugcua ugaauaaugu caauc                                              25

<210> SEQ ID NO 41
<211> LENGTH: 25
<212> TYPE: RNA
<213> ORGANISM: artificial
<220> FEATURE:
<223> OTHER INFORMATION: oligonucleotide

<400> SEQUENCE: 41
uucuugcuau gaauaauguc aaucc                                              25

<210> SEQ ID NO 42
<211> LENGTH: 25
<212> TYPE: RNA
<213> ORGANISM: artificial
<220> FEATURE:
<223> OTHER INFORMATION: oligonucleotide

<400> SEQUENCE: 42
ucuugcuaug aauaauguca auccg                                              25

<210> SEQ ID NO 43
<211> LENGTH: 25
<212> TYPE: RNA
<213> ORGANISM: artificial
<220> FEATURE:
<223> OTHER INFORMATION: oligonucleotide

<400> SEQUENCE: 43
cuugcuauga auaaugucaa uccga                                              25

<210> SEQ ID NO 44
<211> LENGTH: 25
<212> TYPE: RNA
<213> ORGANISM: artificial
<220> FEATURE:
<223> OTHER INFORMATION: oligonucleotide

<400> SEQUENCE: 44
uugcuaugaa uaaugucaau ccgac                                              25

<210> SEQ ID NO 45
<211> LENGTH: 25
<212> TYPE: RNA
<213> ORGANISM: artificial
<220> FEATURE:
<223> OTHER INFORMATION: oligonucleotide

<400> SEQUENCE: 45
ugcuaugaau aaugucaauc cgacc                                              25

```
<210> SEQ ID NO 46
<211> LENGTH: 25
<212> TYPE: RNA
<213> ORGANISM: artificial
<220> FEATURE:
<223> OTHER INFORMATION: oligonucleotide

<400> SEQUENCE: 46
gcuaugaaua augucaaucc gaccu                                              25

<210> SEQ ID NO 47
<211> LENGTH: 25
<212> TYPE: RNA
<213> ORGANISM: artificial
<220> FEATURE:
<223> OTHER INFORMATION: oligonucleotide

<400> SEQUENCE: 47
cuaugaauaa ugucaauccg accug                                              25

<210> SEQ ID NO 48
<211> LENGTH: 25
<212> TYPE: RNA
<213> ORGANISM: artificial
<220> FEATURE:
<223> OTHER INFORMATION: oligonucleotide

<400> SEQUENCE: 48
uaugaauaau gucaauccga ccuga                                              25

<210> SEQ ID NO 49
<211> LENGTH: 25
<212> TYPE: RNA
<213> ORGANISM: artificial
<220> FEATURE:
<223> OTHER INFORMATION: oligonucleotide

<400> SEQUENCE: 49
augaauaaug ucaauccgac cugag                                              25

<210> SEQ ID NO 50
<211> LENGTH: 25
<212> TYPE: RNA
<213> ORGANISM: artificial
<220> FEATURE:
<223> OTHER INFORMATION: oligonucleotide

<400> SEQUENCE: 50
ugaauaaugu caauccgacc ugagc                                              25

<210> SEQ ID NO 51
<211> LENGTH: 25
<212> TYPE: RNA
<213> ORGANISM: artificial
<220> FEATURE:
<223> OTHER INFORMATION: oligonucleotide

<400> SEQUENCE: 51
gaauaauguc aauccgaccu gagcu                                              25

<210> SEQ ID NO 52
<211> LENGTH: 25
<212> TYPE: RNA
<213> ORGANISM: artificial
<220> FEATURE:
<223> OTHER INFORMATION: oligonucleotide
```

<400> SEQUENCE: 52
aauaauguca auccgaccug agcuu                                    25

<210> SEQ ID NO 53
<211> LENGTH: 25
<212> TYPE: RNA
<213> ORGANISM: artificial
<220> FEATURE:
<223> OTHER INFORMATION: oligonucleotide

<400> SEQUENCE: 53
auaaugucaa uccgaccuga gcuuu                                    25

<210> SEQ ID NO 54
<211> LENGTH: 25
<212> TYPE: RNA
<213> ORGANISM: artificial
<220> FEATURE:
<223> OTHER INFORMATION: oligonucleotide

<400> SEQUENCE: 54
uaaugucaau ccgaccugag cuuug                                    25

<210> SEQ ID NO 55
<211> LENGTH: 25
<212> TYPE: RNA
<213> ORGANISM: artificial
<220> FEATURE:
<223> OTHER INFORMATION: oligonucleotide

<400> SEQUENCE: 55
aaugucaauc cgaccugagc uuugu                                    25

<210> SEQ ID NO 56
<211> LENGTH: 25
<212> TYPE: RNA
<213> ORGANISM: artificial
<220> FEATURE:
<223> OTHER INFORMATION: oligonucleotide

<400> SEQUENCE: 56
augucaaucc gaccugagcu uuguu                                    25

<210> SEQ ID NO 57
<211> LENGTH: 25
<212> TYPE: RNA
<213> ORGANISM: artificial
<220> FEATURE:
<223> OTHER INFORMATION: oligonucleotide

<400> SEQUENCE: 57
ugucaauccg accugagcuu uguug                                    25

<210> SEQ ID NO 58
<211> LENGTH: 25
<212> TYPE: RNA
<213> ORGANISM: artificial
<220> FEATURE:
<223> OTHER INFORMATION: oligonucleotide

<400> SEQUENCE: 58
gucaauccga ccugagcuuu guugu                                    25

<210> SEQ ID NO 59
<211> LENGTH: 25

```
<212> TYPE: RNA
<213> ORGANISM: artificial
<220> FEATURE:
<223> OTHER INFORMATION: oligonucleotide

<400> SEQUENCE: 59
ucaauccgac cugagcuuug uugua                                              25

<210> SEQ ID NO 60
<211> LENGTH: 25
<212> TYPE: RNA
<213> ORGANISM: artificial
<220> FEATURE:
<223> OTHER INFORMATION: oligonucleotide

<400> SEQUENCE: 60
caauccgacc ugagcuuugu uguag                                              25

<210> SEQ ID NO 61
<211> LENGTH: 25
<212> TYPE: RNA
<213> ORGANISM: artificial
<220> FEATURE:
<223> OTHER INFORMATION: oligonucleotide

<400> SEQUENCE: 61
aauccgaccu gagcuuuguu guaga                                              25

<210> SEQ ID NO 62
<211> LENGTH: 25
<212> TYPE: RNA
<213> ORGANISM: artificial
<220> FEATURE:
<223> OTHER INFORMATION: olignucleotide

<400> SEQUENCE: 62
auccgaccug agcuuuguug uagac                                              25

<210> SEQ ID NO 63
<211> LENGTH: 25
<212> TYPE: RNA
<213> ORGANISM: artificial
<220> FEATURE:
<223> OTHER INFORMATION: oligonucleotide

<400> SEQUENCE: 63
uccgaccuga gcuuuguugu agacu                                              25

<210> SEQ ID NO 64
<211> LENGTH: 25
<212> TYPE: RNA
<213> ORGANISM: artificial
<220> FEATURE:
<223> OTHER INFORMATION: oligonucleotide

<400> SEQUENCE: 64
ccgaccugag cuuuguugua gacua                                              25

<210> SEQ ID NO 65
<211> LENGTH: 20
<212> TYPE: RNA
<213> ORGANISM: artificial
<220> FEATURE:
<223> OTHER INFORMATION: oligonucleotide

<400> SEQUENCE: 65
```
cgaccugagc uuuguuguag                                              20

<210> SEQ ID NO 66
<211> LENGTH: 25
<212> TYPE: RNA
<213> ORGANISM: artificial
<220> FEATURE:
<223> OTHER INFORMATION: oligonucleotide

<400> SEQUENCE: 66
cgaccugagc uuuguuguag acuau                                        25

<210> SEQ ID NO 67
<211> LENGTH: 25
<212> TYPE: RNA
<213> ORGANISM: artificial
<220> FEATURE:
<223> OTHER INFORMATION: oligonucleotide

<400> SEQUENCE: 67
gaccugagcu uuguuguaga cuauc                                        25

<210> SEQ ID NO 68
<211> LENGTH: 25
<212> TYPE: RNA
<213> ORGANISM: artificial
<220> FEATURE:
<223> OTHER INFORMATION: oligonucleotide

<400> SEQUENCE: 68
accugagcuu uguuguagac uauca                                        25

<210> SEQ ID NO 69
<211> LENGTH: 23
<212> TYPE: RNA
<213> ORGANISM: artificial
<220> FEATURE:
<223> OTHER INFORMATION: oligonucleotide

<400> SEQUENCE: 69
ccugagcuuu guuguagacu auc                                          23

<210> SEQ ID NO 70
<211> LENGTH: 25
<212> TYPE: RNA
<213> ORGANISM: artificial
<220> FEATURE:
<223> OTHER INFORMATION: oligonucleotide

<400> SEQUENCE: 70
gcuuuucuuu uaguugcugc ucuuu                                        25

<210> SEQ ID NO 71
<211> LENGTH: 25
<212> TYPE: RNA
<213> ORGANISM: artificial
<220> FEATURE:
<223> OTHER INFORMATION: oligonucleotide

<400> SEQUENCE: 71
cuuuucuuuu aguugcugcu cuuuu                                        25

<210> SEQ ID NO 72
<211> LENGTH: 25
<212> TYPE: RNA
<213> ORGANISM: artificial

```
<220> FEATURE:
<223> OTHER INFORMATION: oligonucleotide

<400> SEQUENCE: 72
uuuucuuuua guugcugcuc uuuuc                                             25

<210> SEQ ID NO 73
<211> LENGTH: 25
<212> TYPE: RNA
<213> ORGANISM: artificial
<220> FEATURE:
<223> OTHER INFORMATION: oligonucleotide

<400> SEQUENCE: 73
uuucuuuuag uugcugcucu uuucc                                             25

<210> SEQ ID NO 74
<211> LENGTH: 25
<212> TYPE: RNA
<213> ORGANISM: artificial
<220> FEATURE:
<223> OTHER INFORMATION: oligonucleotide

<400> SEQUENCE: 74
uucuuuuagu ugcugcucuu uucca                                             25

<210> SEQ ID NO 75
<211> LENGTH: 25
<212> TYPE: RNA
<213> ORGANISM: artificial
<220> FEATURE:
<223> OTHER INFORMATION: oligonucleotide

<400> SEQUENCE: 75
ucuuuuaguu gcugcucuuu uccag                                             25

<210> SEQ ID NO 76
<211> LENGTH: 25
<212> TYPE: RNA
<213> ORGANISM: artificial
<220> FEATURE:
<223> OTHER INFORMATION: oligonucleotide

<400> SEQUENCE: 76
cuuuuaguug cugcucuuuu ccagg                                             25

<210> SEQ ID NO 77
<211> LENGTH: 25
<212> TYPE: RNA
<213> ORGANISM: artificial
<220> FEATURE:
<223> OTHER INFORMATION: oligonucleotide

<400> SEQUENCE: 77
uuuuaguugc ugcucuuuuc caggu                                             25

<210> SEQ ID NO 78
<211> LENGTH: 25
<212> TYPE: RNA
<213> ORGANISM: artificial
<220> FEATURE:
<223> OTHER INFORMATION: oligonucleotide

<400> SEQUENCE: 78
uuuaguugcu gcucuuuucc agguu                                             25
```

```
<210> SEQ ID NO 79
<211> LENGTH: 25
<212> TYPE: RNA
<213> ORGANISM: artificial
<220> FEATURE:
<223> OTHER INFORMATION: oligonucleotide

<400> SEQUENCE: 79
uuaguugcug cucuuuucca gguuc                                       25

<210> SEQ ID NO 80
<211> LENGTH: 25
<212> TYPE: RNA
<213> ORGANISM: artificial
<220> FEATURE:
<223> OTHER INFORMATION: oligonucleotide

<400> SEQUENCE: 80
uaguugcugc ucuuuuccag guuca                                       25

<210> SEQ ID NO 81
<211> LENGTH: 25
<212> TYPE: RNA
<213> ORGANISM: artificial
<220> FEATURE:
<223> OTHER INFORMATION: oligonucleotide

<400> SEQUENCE: 81
aguugcugcu cuuuuccagg uucaa                                       25

<210> SEQ ID NO 82
<211> LENGTH: 25
<212> TYPE: RNA
<213> ORGANISM: artificial
<220> FEATURE:
<223> OTHER INFORMATION: oligonucleotide

<400> SEQUENCE: 82
guugcugcuc uuuuccaggu ucaag                                       25

<210> SEQ ID NO 83
<211> LENGTH: 25
<212> TYPE: RNA
<213> ORGANISM: artificial
<220> FEATURE:
<223> OTHER INFORMATION: oligonucleotide

<400> SEQUENCE: 83
uugcugcucu uuuccagguu caagu                                       25

<210> SEQ ID NO 84
<211> LENGTH: 25
<212> TYPE: RNA
<213> ORGANISM: artificial
<220> FEATURE:
<223> OTHER INFORMATION: oligonucleotide

<400> SEQUENCE: 84
ugcugcucuu uuccagguuc aagug                                       25

<210> SEQ ID NO 85
<211> LENGTH: 25
<212> TYPE: RNA
<213> ORGANISM: artificial
<220> FEATURE:
<223> OTHER INFORMATION: oligonucleotide
```

```
<400> SEQUENCE: 85
gcugcucuuu uccagguuca agugg                                        25

<210> SEQ ID NO 86
<211> LENGTH: 25
<212> TYPE: RNA
<213> ORGANISM: artificial
<220> FEATURE:
<223> OTHER INFORMATION: oligonucleotide

<400> SEQUENCE: 86
cugcucuuuu ccagguucaa guggg                                        25

<210> SEQ ID NO 87
<211> LENGTH: 25
<212> TYPE: RNA
<213> ORGANISM: artificial
<220> FEATURE:
<223> OTHER INFORMATION: oligonucleotide

<400> SEQUENCE: 87
ugcucuuuuc cagguucaag uggga                                        25

<210> SEQ ID NO 88
<211> LENGTH: 25
<212> TYPE: RNA
<213> ORGANISM: artificial
<220> FEATURE:
<223> OTHER INFORMATION: oligonucleotide

<400> SEQUENCE: 88
gcucuuuucc agguucaagu gggac                                        25

<210> SEQ ID NO 89
<211> LENGTH: 25
<212> TYPE: RNA
<213> ORGANISM: artificial
<220> FEATURE:
<223> OTHER INFORMATION: oligonucleotide

<400> SEQUENCE: 89
cucuuuucca gguucaagug ggaua                                        25

<210> SEQ ID NO 90
<211> LENGTH: 25
<212> TYPE: RNA
<213> ORGANISM: artificial
<220> FEATURE:
<223> OTHER INFORMATION: oligonucleotide

<400> SEQUENCE: 90
ucuuuuccag guucaagugg gauac                                        25

<210> SEQ ID NO 91
<211> LENGTH: 20
<212> TYPE: RNA
<213> ORGANISM: artificial
<220> FEATURE:
<223> OTHER INFORMATION: oligonucleotide

<400> SEQUENCE: 91
ucuuuuccag guucaagugg                                              20

<210> SEQ ID NO 92
```

```
<211> LENGTH: 25
<212> TYPE: RNA
<213> ORGANISM: artificial
<220> FEATURE:
<223> OTHER INFORMATION: oligonucleotide

<400> SEQUENCE: 92
cuuuuccagg uucaagugggg auacu                                            25

<210> SEQ ID NO 93
<211> LENGTH: 25
<212> TYPE: RNA
<213> ORGANISM: artificial
<220> FEATURE:
<223> OTHER INFORMATION: oligonucleotide

<400> SEQUENCE: 93
uuuuccaggu ucaaguggga uacua                                             25

<210> SEQ ID NO 94
<211> LENGTH: 25
<212> TYPE: RNA
<213> ORGANISM: artificial
<220> FEATURE:
<223> OTHER INFORMATION: oligonucleotide

<400> SEQUENCE: 94
uuuccagguu caagugggau acuag                                             25

<210> SEQ ID NO 95
<211> LENGTH: 25
<212> TYPE: RNA
<213> ORGANISM: artificial
<220> FEATURE:
<223> OTHER INFORMATION: oligonucleotide

<400> SEQUENCE: 95
uuccagguuc aagugggaua cuagc                                             25

<210> SEQ ID NO 96
<211> LENGTH: 25
<212> TYPE: RNA
<213> ORGANISM: artificial
<220> FEATURE:
<223> OTHER INFORMATION: oligonucleotide

<400> SEQUENCE: 96
uccagguuca agugggauac uagca                                             25

<210> SEQ ID NO 97
<211> LENGTH: 25
<212> TYPE: RNA
<213> ORGANISM: artificial
<220> FEATURE:
<223> OTHER INFORMATION: oligonucleotide

<400> SEQUENCE: 97
ccagguucaa gugggauacu agcaa                                             25

<210> SEQ ID NO 98
<211> LENGTH: 25
<212> TYPE: RNA
<213> ORGANISM: artificial
<220> FEATURE:
<223> OTHER INFORMATION: oligonucleotide

<400> SEQUENCE: 98
```
cagguucaag ugggauacua gcaau                        25

<210> SEQ ID NO 99
<211> LENGTH: 25
<212> TYPE: RNA
<213> ORGANISM: artificial
<220> FEATURE:
<223> OTHER INFORMATION: oligonucleotide

<400> SEQUENCE: 99
agguucaagu gggauacuag caaug                        25

<210> SEQ ID NO 100
<211> LENGTH: 25
<212> TYPE: RNA
<213> ORGANISM: artificial
<220> FEATURE:
<223> OTHER INFORMATION: oligonucleotide

<400> SEQUENCE: 100
gguucaagug ggauacuagc aaugu                        25

<210> SEQ ID NO 101
<211> LENGTH: 25
<212> TYPE: RNA
<213> ORGANISM: artificial
<220> FEATURE:
<223> OTHER INFORMATION: oligonucleotide

<400> SEQUENCE: 101
guucaagugg gauacuagca auguu                        25

<210> SEQ ID NO 102
<211> LENGTH: 25
<212> TYPE: RNA
<213> ORGANISM: artificial
<220> FEATURE:
<223> OTHER INFORMATION: oligonucleotide

<400> SEQUENCE: 102 uucaagugggg auacuagcaa uguua                       25

<210> SEQ ID NO 103
<211> LENGTH: 25
<212> TYPE: RNA
<213> ORGANISM: artificial
<220> FEATURE:
<223> OTHER INFORMATION: oligonucleotide

<400> SEQUENCE: 103
ucaaguggga uacuagcaau guuau                        25

<210> SEQ ID NO 104
<211> LENGTH: 25
<212> TYPE: RNA
<213> ORGANISM: artificial
<220> FEATURE:
<223> OTHER INFORMATION: oligonucleotide

<400> SEQUENCE: 104
caagugggau acuagcaaug uuauc                        25

<210> SEQ ID NO 105
<211> LENGTH: 25
<212> TYPE: RNA

<213> ORGANISM: artificial
<220> FEATURE:
<223> OTHER INFORMATION: oligonucleotide

<400> SEQUENCE: 105
aagugggaua cuagcaaugu uaucu                                    25

<210> SEQ ID NO 106
<211> LENGTH: 25
<212> TYPE: RNA
<213> ORGANISM: artificial
<220> FEATURE:
<223> OTHER INFORMATION: oligonucleotide

<400> SEQUENCE: 106
agugggauac uagcaauguu aucug                                    25

<210> SEQ ID NO 107
<211> LENGTH: 25
<212> TYPE: RNA
<213> ORGANISM: artificial
<220> FEATURE:
<223> OTHER INFORMATION: oligonucleotide

<400> SEQUENCE: 107
gugggauacu agcaauguua ucugc                                    25

<210> SEQ ID NO 108
<211> LENGTH: 25
<212> TYPE: RNA
<213> ORGANISM: artificial
<220> FEATURE:
<223> OTHER INFORMATION: oligonucleotide

<400> SEQUENCE: 108
ugggauacua gcaauguuau cugcu                                    25

<210> SEQ ID NO 109
<211> LENGTH: 25
<212> TYPE: RNA
<213> ORGANISM: artificial
<220> FEATURE:
<223> OTHER INFORMATION: oligonucleotide

<400> SEQUENCE: 109
gggauacuag caauguuauc ugcuu                                    25

<210> SEQ ID NO 110
<211> LENGTH: 25
<212> TYPE: RNA
<213> ORGANISM: artificial
<220> FEATURE:
<223> OTHER INFORMATION: oligonucleotide

<400> SEQUENCE: 110
ggauacuagc aauguuaucu gcuuc                                    25

<210> SEQ ID NO 111
<211> LENGTH: 25
<212> TYPE: RNA
<213> ORGANISM: artificial
<220> FEATURE:
<223> OTHER INFORMATION: oligonucleotide

<400> SEQUENCE: 111
gauacuagca auguuaucug cuucc                                    25

```
<210> SEQ ID NO 112
<211> LENGTH: 25
<212> TYPE: RNA
<213> ORGANISM: artificial
<220> FEATURE:
<223> OTHER INFORMATION: oligonucleotide

<400> SEQUENCE: 112
auacuagcaa uguuaucugc uuccu                                              25

<210> SEQ ID NO 113
<211> LENGTH: 25
<212> TYPE: RNA
<213> ORGANISM: artificial
<220> FEATURE:
<223> OTHER INFORMATION: oligonucleotide

<400> SEQUENCE: 113
uacuagcaau guuaucugcu uccuc                                              25

<210> SEQ ID NO 114
<211> LENGTH: 25
<212> TYPE: RNA
<213> ORGANISM: artificial
<220> FEATURE:
<223> OTHER INFORMATION: oligonucleotide

<400> SEQUENCE: 114
acuagcaaug uuaucugcuu ccucc                                              25

<210> SEQ ID NO 115
<211> LENGTH: 25
<212> TYPE: RNA
<213> ORGANISM: artificial
<220> FEATURE:
<223> OTHER INFORMATION: oligonucleotide

<400> SEQUENCE: 115
cuagcaaugu uaucugcuuc cucca                                              25

<210> SEQ ID NO 116
<211> LENGTH: 25
<212> TYPE: RNA
<213> ORGANISM: artificial
<220> FEATURE:
<223> OTHER INFORMATION: oligonucleotide

<400> SEQUENCE: 116
uagcaauguu aucugcuucc uccaa                                              25

<210> SEQ ID NO 117
<211> LENGTH: 25
<212> TYPE: RNA
<213> ORGANISM: artificial
<220> FEATURE:
<223> OTHER INFORMATION: oligonucleotide

<400> SEQUENCE: 117
agcaauguua ucugcuuccu ccaac                                              25

<210> SEQ ID NO 118
<211> LENGTH: 25
<212> TYPE: RNA
<213> ORGANISM: artificial
<220> FEATURE:
```

<223> OTHER INFORMATION: oligonucleotide

<400> SEQUENCE: 118
gcaauguuau cugcuuccuc caacc                                      25

<210> SEQ ID NO 119
<211> LENGTH: 25
<212> TYPE: RNA
<213> ORGANISM: artificial
<220> FEATURE:
<223> OTHER INFORMATION: oligonucleotide

<400> SEQUENCE: 119
caauguuauc ugcuuccucc aacca                                      25

<210> SEQ ID NO 120
<211> LENGTH: 25
<212> TYPE: RNA
<213> ORGANISM: artificial
<220> FEATURE:
<223> OTHER INFORMATION: oligonucleotide

<400> SEQUENCE: 120
aauguuaucu gcuuccucca accau                                      25

<210> SEQ ID NO 121
<211> LENGTH: 25
<212> TYPE: RNA
<213> ORGANISM: artificial
<220> FEATURE:
<223> OTHER INFORMATION: oligonucleotide

<400> SEQUENCE: 121
auguuaucug cuuccuccaa ccaua                                      25

<210> SEQ ID NO 122
<211> LENGTH: 25
<212> TYPE: RNA
<213> ORGANISM: artificial
<220> FEATURE:
<223> OTHER INFORMATION: oligonucleotide

<400> SEQUENCE: 122
uguuaucugc uuccuccaac cauaa                                      25

<210> SEQ ID NO 123
<211> LENGTH: 25
<212> TYPE: RNA
<213> ORGANISM: artificial
<220> FEATURE:
<223> OTHER INFORMATION: oligonucleotide

<400> SEQUENCE: 123
ccaauagugg ucaguccagg agcua                                      25

<210> SEQ ID NO 124
<211> LENGTH: 25
<212> TYPE: RNA
<213> ORGANISM: artificial
<220> FEATURE:
<223> OTHER INFORMATION: oligonucleotide

<400> SEQUENCE: 124 caauagugguu caguccagga gcuag                                     25

```
<210> SEQ ID NO 125
<211> LENGTH: 25
<212> TYPE: RNA
<213> ORGANISM: artificial
<220> FEATURE:
<223> OTHER INFORMATION: oligonucleotide

<400> SEQUENCE: 125
aauagugguc aguccaggag cuagg                                          25

<210> SEQ ID NO 126
<211> LENGTH: 25
<212> TYPE: RNA
<213> ORGANISM: artificial
<220> FEATURE:
<223> OTHER INFORMATION: oligonucleotide

<400> SEQUENCE: 126
auagugguca guccaggagc uaggu                                          25

<210> SEQ ID NO 127
<211> LENGTH: 21
<212> TYPE: RNA
<213> ORGANISM: artificial
<220> FEATURE:
<223> OTHER INFORMATION: oligonucleotide

<400> SEQUENCE: 127
auagugguca guccaggagc u                                              21

<210> SEQ ID NO 128
<211> LENGTH: 25
<212> TYPE: RNA
<213> ORGANISM: artificial
<220> FEATURE:
<223> OTHER INFORMATION: oligonucleotide

<400> SEQUENCE: 128
uaguggucag uccaggagcu agguc                                          25

<210> SEQ ID NO 129
<211> LENGTH: 25
<212> TYPE: RNA
<213> ORGANISM: artificial
<220> FEATURE:
<223> OTHER INFORMATION: oligonucleotide

<400> SEQUENCE: 129
aguggucagu ccaggagcua gguca                                          25

<210> SEQ ID NO 130
<211> LENGTH: 25
<212> TYPE: RNA
<213> ORGANISM: artificial
<220> FEATURE:
<223> OTHER INFORMATION: oligonucleotide

<400> SEQUENCE: 130
guggucaguc caggagcuag gucag                                          25

<210> SEQ ID NO 131
<211> LENGTH: 25
<212> TYPE: RNA
<213> ORGANISM: artificial
<220> FEATURE:
<223> OTHER INFORMATION: oligonucleotide
```

<400> SEQUENCE: 131
uggucagucc aggagcuagg ucagg                                              25

<210> SEQ ID NO 132
<211> LENGTH: 25
<212> TYPE: RNA
<213> ORGANISM: artificial
<220> FEATURE:
<223> OTHER INFORMATION: oligonucleotide

<400> SEQUENCE: 132
ggucagucca ggagcuaggu caggc                                              25

<210> SEQ ID NO 133
<211> LENGTH: 25
<212> TYPE: RNA
<213> ORGANISM: artificial
<220> FEATURE:
<223> OTHER INFORMATION: oligonucleotide

<400> SEQUENCE: 133
gucaguccag gagcuagguc aggcu                                              25

<210> SEQ ID NO 134
<211> LENGTH: 25
<212> TYPE: RNA
<213> ORGANISM: artificial
<220> FEATURE:
<223> OTHER INFORMATION: oligonucleotide

<400> SEQUENCE: 134
ucaguccagg agcuagguca ggcug                                              25

<210> SEQ ID NO 135
<211> LENGTH: 25
<212> TYPE: RNA
<213> ORGANISM: artificial
<220> FEATURE:
<223> OTHER INFORMATION: oligonucleotide

<400> SEQUENCE: 135
caguccagga gcuaggucag gcugc                                              25

<210> SEQ ID NO 136
<211> LENGTH: 25
<212> TYPE: RNA
<213> ORGANISM: artificial
<220> FEATURE:
<223> OTHER INFORMATION: oligonucleotide

<400> SEQUENCE: 136
aguccaggag cuaggucagg cugcu                                              25

<210> SEQ ID NO 137
<211> LENGTH: 25
<212> TYPE: RNA
<213> ORGANISM: artificial
<220> FEATURE:
<223> OTHER INFORMATION: oligonucleotide

<400> SEQUENCE: 137
guccaggagc uaggucaggc ugcuu                                              25

<210> SEQ ID NO 138
<211> LENGTH: 25

```
<212> TYPE: RNA
<213> ORGANISM: artificial
<220> FEATURE:
<223> OTHER INFORMATION: oligonucleotide

<400> SEQUENCE: 138
uccaggagcu aggucaggcu gcuuu                                              25

<210> SEQ ID NO 139
<211> LENGTH: 25
<212> TYPE: RNA
<213> ORGANISM: artificial
<220> FEATURE:
<223> OTHER INFORMATION: oligonucleotide

<400> SEQUENCE: 139
ccaggagcua ggucaggcug cuuug                                              25

<210> SEQ ID NO 140
<211> LENGTH: 25
<212> TYPE: RNA
<213> ORGANISM: artificial
<220> FEATURE:
<223> OTHER INFORMATION: oligonucleotide

<400> SEQUENCE: 140
caggagcuag gucaggcugc uuugc                                              25

<210> SEQ ID NO 141
<211> LENGTH: 25
<212> TYPE: RNA
<213> ORGANISM: artificial
<220> FEATURE:
<223> OTHER INFORMATION: oligonucleotide

<400> SEQUENCE: 141
aggagcuagg ucaggcugcu uugcc                                              25

<210> SEQ ID NO 142
<211> LENGTH: 25
<212> TYPE: RNA
<213> ORGANISM: artificial
<220> FEATURE:
<223> OTHER INFORMATION: oligonucleotide

<400> SEQUENCE: 142
ggagcuaggu caggcugcuu ugccc                                              25

<210> SEQ ID NO 143
<211> LENGTH: 25
<212> TYPE: RNA
<213> ORGANISM: artificial
<220> FEATURE:
<223> OTHER INFORMATION: oligonucleotide

<400> SEQUENCE: 143
gagcuagguc aggcugcuuu gcccu                                              25

<210> SEQ ID NO 144
<211> LENGTH: 25
<212> TYPE: RNA
<213> ORGANISM: artificial
<220> FEATURE:
<223> OTHER INFORMATION: oligonucleotide

<400> SEQUENCE: 144
```
agcuagguca ggcugcuuug cccuc                                          25

<210> SEQ ID NO 145
<211> LENGTH: 25
<212> TYPE: RNA
<213> ORGANISM: artificial
<220> FEATURE:
<223> OTHER INFORMATION: oligonucleotide

<400> SEQUENCE: 145
gcuaggucag gcugcuuugc ccuca                                          25

<210> SEQ ID NO 146
<211> LENGTH: 25
<212> TYPE: RNA
<213> ORGANISM: artificial
<220> FEATURE:
<223> OTHER INFORMATION: oligonucleotide

<400> SEQUENCE: 146
cuaggucagg cugcuuugcc cucag                                          25

<210> SEQ ID NO 147
<211> LENGTH: 25
<212> TYPE: RNA
<213> ORGANISM: artificial
<220> FEATURE:
<223> OTHER INFORMATION: oligonucleotide

<400> SEQUENCE: 147
uaggucaggc ugcuuugccc ucagc                                          25

<210> SEQ ID NO 148
<211> LENGTH: 25
<212> TYPE: RNA
<213> ORGANISM: artificial
<220> FEATURE:
<223> OTHER INFORMATION: oligonucleotide

<400> SEQUENCE: 148
aggucaggcu gcuuugcccu cagcu                                          25

<210> SEQ ID NO 149
<211> LENGTH: 25
<212> TYPE: RNA
<213> ORGANISM: artificial
<220> FEATURE:
<223> OTHER INFORMATION: oligonucleotide

<400> SEQUENCE: 149
ggucaggcug cuuugcccuc agcuc                                          25

<210> SEQ ID NO 150
<211> LENGTH: 25
<212> TYPE: RNA
<213> ORGANISM: artificial
<220> FEATURE:
<223> OTHER INFORMATION: oligonucleotide

<400> SEQUENCE: 150
gucaggcugc uuugcccuca gcucu                                          25

<210> SEQ ID NO 151
<211> LENGTH: 25
<212> TYPE: RNA
<213> ORGANISM: artificial

-continued

```
<220> FEATURE:
<223> OTHER INFORMATION: oligonucleotide

<400> SEQUENCE: 151
ucaggcugcu uugcccucag cucuu                                              25

<210> SEQ ID NO 152
<211> LENGTH: 25
<212> TYPE: RNA
<213> ORGANISM: artificial
<220> FEATURE:
<223> OTHER INFORMATION: oligonucleotide

<400> SEQUENCE: 152
caggcugcuu ugcccucagc ucuug                                              25

<210> SEQ ID NO 153
<211> LENGTH: 25
<212> TYPE: RNA
<213> ORGANISM: artificial
<220> FEATURE:
<223> OTHER INFORMATION: oligonucleotide

<400> SEQUENCE: 153
aggcugcuuu gcccucagcu cuuga                                              25

<210> SEQ ID NO 154
<211> LENGTH: 25
<212> TYPE: RNA
<213> ORGANISM: artificial
<220> FEATURE:
<223> OTHER INFORMATION: oligonucleotide

<400> SEQUENCE: 154
ggcugcuuug cccucagcuc uugaa                                              25

<210> SEQ ID NO 155
<211> LENGTH: 25
<212> TYPE: RNA
<213> ORGANISM: artificial
<220> FEATURE:
<223> OTHER INFORMATION: oligonucleotide

<400> SEQUENCE: 155
gcugcuuugc ccucagcucu ugaag                                              25

<210> SEQ ID NO 156
<211> LENGTH: 25
<212> TYPE: RNA
<213> ORGANISM: artificial
<220> FEATURE:
<223> OTHER INFORMATION: oligonucleotide

<400> SEQUENCE: 156
cugcuuugcc cucagcucuu gaagu                                              25

<210> SEQ ID NO 157
<211> LENGTH: 25
<212> TYPE: RNA
<213> ORGANISM: artificial
<220> FEATURE:
<223> OTHER INFORMATION: oligonucleotide

<400> SEQUENCE: 157
ugcuuugccc ucagcucuug aagua                                              25
```

<210> SEQ ID NO 158
<211> LENGTH: 25
<212> TYPE: RNA
<213> ORGANISM: artificial
<220> FEATURE:
<223> OTHER INFORMATION: oligonucleotide

<400> SEQUENCE: 158
gcuuugcccu cagcucuuga aguaa                                    25

<210> SEQ ID NO 159
<211> LENGTH: 25
<212> TYPE: RNA
<213> ORGANISM: artificial
<220> FEATURE:
<223> OTHER INFORMATION: oligonucleotide

<400> SEQUENCE: 159
cuuugcccuc agcucuugaa guaaa                                    25

<210> SEQ ID NO 160
<211> LENGTH: 25
<212> TYPE: RNA
<213> ORGANISM: artificial
<220> FEATURE:
<223> OTHER INFORMATION: oligonucleotide

<400> SEQUENCE: 160
uuugcccuca gcucuugaag uaaac                                    25

<210> SEQ ID NO 161
<211> LENGTH: 25
<212> TYPE: RNA
<213> ORGANISM: artificial
<220> FEATURE:
<223> OTHER INFORMATION: oligonucleotide

<400> SEQUENCE: 161
uugcccucag cucuugaagu aaacg                                    25

<210> SEQ ID NO 162
<211> LENGTH: 25
<212> TYPE: RNA
<213> ORGANISM: artificial
<220> FEATURE:
<223> OTHER INFORMATION: oligonucleotide

<400> SEQUENCE: 162
ugcccucagc ucuugaagua aacgg                                    25

<210> SEQ ID NO 163
<211> LENGTH: 25
<212> TYPE: RNA
<213> ORGANISM: artificial
<220> FEATURE:
<223> OTHER INFORMATION: oligonucleotide

<400> SEQUENCE: 163
gcccucagcu cuugaaguaa acggu                                    25

<210> SEQ ID NO 164
<211> LENGTH: 25
<212> TYPE: RNA
<213> ORGANISM: artificial
<220> FEATURE:
<223> OTHER INFORMATION: oligonucleotide

<400> SEQUENCE: 164
cccucagcuc uugaaguaaa cgguu                                    25

<210> SEQ ID NO 165
<211> LENGTH: 20
<212> TYPE: RNA
<213> ORGANISM: artificial
<220> FEATURE:
<223> OTHER INFORMATION: oligonucleotide

<400> SEQUENCE: 165
ccucagcucu ugaaguaaac                                          20

<210> SEQ ID NO 166
<211> LENGTH: 21
<212> TYPE: RNA
<213> ORGANISM: artificial
<220> FEATURE:
<223> OTHER INFORMATION: oligonucleotide

<400> SEQUENCE: 166
ccucagcucu ugaaguaaac g                                        21

<210> SEQ ID NO 167
<211> LENGTH: 20
<212> TYPE: RNA
<213> ORGANISM: artificial
<220> FEATURE:
<223> OTHER INFORMATION: oligonucleotide

<400> SEQUENCE: 167
cucagcucuu gaaguaaacg                                          20

<210> SEQ ID NO 168
<211> LENGTH: 25
<212> TYPE: RNA
<213> ORGANISM: artificial
<220> FEATURE:
<223> OTHER INFORMATION: oligonucleotide

<400> SEQUENCE: 168
guaccuccaa caucaaggaa gaugg                                    25

<210> SEQ ID NO 169
<211> LENGTH: 25
<212> TYPE: RNA
<213> ORGANISM: artificial
<220> FEATURE:
<223> OTHER INFORMATION: oligonucleotide

<400> SEQUENCE: 169
uaccuccaac aucaaggaag auggc                                    25

<210> SEQ ID NO 170
<211> LENGTH: 25
<212> TYPE: RNA
<213> ORGANISM: artificial
<220> FEATURE:
<223> OTHER INFORMATION: oligonucleotide

<400> SEQUENCE: 170
accuccaaca ucaaggaaga uggca                                    25

<210> SEQ ID NO 171

```
<211> LENGTH: 25
<212> TYPE: RNA
<213> ORGANISM: artificial
<220> FEATURE:
<223> OTHER INFORMATION: oligonucleotide

<400> SEQUENCE: 171
ccuccaacau caaggaagau ggcau                                          25

<210> SEQ ID NO 172
<211> LENGTH: 25
<212> TYPE: RNA
<213> ORGANISM: artificial
<220> FEATURE:
<223> OTHER INFORMATION: oligonucleotide

<400> SEQUENCE: 172
cuccaacauc aaggaagaug gcauu                                          25

<210> SEQ ID NO 173
<211> LENGTH: 25
<212> TYPE: RNA
<213> ORGANISM: artificial
<220> FEATURE:
<223> OTHER INFORMATION: oligonucleotide

<400> SEQUENCE: 173
uccaacauca aggaagaugg cauuu                                          25

<210> SEQ ID NO 174
<211> LENGTH: 25
<212> TYPE: RNA
<213> ORGANISM: artificial
<220> FEATURE:
<223> OTHER INFORMATION: oligonuclelotide

<400> SEQUENCE: 174
ccaacaucaa ggaagauggc auuuc                                          25

<210> SEQ ID NO 175
<211> LENGTH: 25
<212> TYPE: RNA
<213> ORGANISM: artificial
<220> FEATURE:
<223> OTHER INFORMATION: oligonucleotide

<400> SEQUENCE: 175
caacaucaag gaagauggca uuucu                                          25

<210> SEQ ID NO 176
<211> LENGTH: 25
<212> TYPE: RNA
<213> ORGANISM: artificial
<220> FEATURE:
<223> OTHER INFORMATION: oligonucleotide

<400> SEQUENCE: 176
aacaucaagg aagauggcau uucua                                          25

<210> SEQ ID NO 177
<211> LENGTH: 25
<212> TYPE: RNA
<213> ORGANISM: artificial
<220> FEATURE:
<223> OTHER INFORMATION: oligonucleotide

<400> SEQUENCE: 177
```
acaucaagga agauggcauu ucuag    25

<210> SEQ ID NO 178
<211> LENGTH: 25
<212> TYPE: RNA
<213> ORGANISM: artificial
<220> FEATURE:
<223> OTHER INFORMATION: oligonucleotide

<400> SEQUENCE: 178
caucaaggaa gauggcauuu cuagu    25

<210> SEQ ID NO 179
<211> LENGTH: 25
<212> TYPE: RNA
<213> ORGANISM: artificial
<220> FEATURE:
<223> OTHER INFORMATION: oligonucleotide

<400> SEQUENCE: 179
aucaaggaag auggcauuuc uaguu    25

<210> SEQ ID NO 180
<211> LENGTH: 25
<212> TYPE: RNA
<213> ORGANISM: artificial
<220> FEATURE:
<223> OTHER INFORMATION: oligonucleotide

<400> SEQUENCE: 180
ucaaggaaga uggcauuucu aguuu    25

<210> SEQ ID NO 181
<211> LENGTH: 25
<212> TYPE: RNA
<213> ORGANISM: artificial
<220> FEATURE:
<223> OTHER INFORMATION: oligonucleotide

<400> SEQUENCE: 181
caaggaagau ggcauuucua guuug    25

<210> SEQ ID NO 182
<211> LENGTH: 25
<212> TYPE: RNA
<213> ORGANISM: artificial
<220> FEATURE:
<223> OTHER INFORMATION: oligonucleotide

<400> SEQUENCE: 182
aaggaagaug gcauuucuag uuugg    25

<210> SEQ ID NO 183
<211> LENGTH: 25
<212> TYPE: RNA
<213> ORGANISM: artificial
<220> FEATURE:
<223> OTHER INFORMATION: oligonucleotide

<400> SEQUENCE: 183
aggaagaugg cauuucuagu uugga    25

<210> SEQ ID NO 184
<211> LENGTH: 25
<212> TYPE: RNA

```
<213> ORGANISM: artificial
<220> FEATURE:
<223> OTHER INFORMATION: oligonucleotide

<400> SEQUENCE: 184
ggaagauggc auuucuaguu uggag                                       25

<210> SEQ ID NO 185
<211> LENGTH: 25
<212> TYPE: RNA
<213> ORGANISM: artificial
<220> FEATURE:
<223> OTHER INFORMATION: oligonucleotide

<400> SEQUENCE: 185
gaagauggca uuucuaguuu ggaga                                       25

<210> SEQ ID NO 186
<211> LENGTH: 25
<212> TYPE: RNA
<213> ORGANISM: artificial
<220> FEATURE:
<223> OTHER INFORMATION: oligonucleotide

<400> SEQUENCE: 186
aagauggcau uucuaguuug gagau                                       25

<210> SEQ ID NO 187
<211> LENGTH: 25
<212> TYPE: RNA
<213> ORGANISM: artificial
<220> FEATURE:
<223> OTHER INFORMATION: oligonucleotide

<400> SEQUENCE: 187
agauggcauu ucuaguuugg agaug                                       25

<210> SEQ ID NO 188
<211> LENGTH: 25
<212> TYPE: RNA
<213> ORGANISM: artificial
<220> FEATURE:
<223> OTHER INFORMATION: oligonucleotide

<400> SEQUENCE: 188
gauggcauuu cuaguuugga gaugg                                       25

<210> SEQ ID NO 189
<211> LENGTH: 25
<212> TYPE: RNA
<213> ORGANISM: artificial
<220> FEATURE:
<223> OTHER INFORMATION: oligonucleotide

<400> SEQUENCE: 189
auggcauuuc uaguuuggag auggc                                       25

<210> SEQ ID NO 190
<211> LENGTH: 25
<212> TYPE: RNA
<213> ORGANISM: artificial
<220> FEATURE:
<223> OTHER INFORMATION: oligonucleotide

<400> SEQUENCE: 190
uggcauuucu aguuuggaga uggca                                       25
```

<210> SEQ ID NO 191
<211> LENGTH: 25
<212> TYPE: RNA
<213> ORGANISM: artificial
<220> FEATURE:
<223> OTHER INFORMATION: oligonucleotide

<400> SEQUENCE: 191
ggcauuucua guuggagau ggcag                                           25

<210> SEQ ID NO 192
<211> LENGTH: 25
<212> TYPE: RNA
<213> ORGANISM: artificial
<220> FEATURE:
<223> OTHER INFORMATION: oligonucleotide

<400> SEQUENCE: 192
gcauuucuag uuggagaug gcagu                                           25

<210> SEQ ID NO 193
<211> LENGTH: 25
<212> TYPE: RNA
<213> ORGANISM: artificial
<220> FEATURE:
<223> OTHER INFORMATION: oligonucleotide

<400> SEQUENCE: 193
cauuucuagu uggagaugg caguu                                           25

<210> SEQ ID NO 194
<211> LENGTH: 25
<212> TYPE: RNA
<213> ORGANISM: artificial
<220> FEATURE:
<223> OTHER INFORMATION: oligonucleotide

<400> SEQUENCE: 194
auuucuaguu uggagauggc aguuu                                          25

<210> SEQ ID NO 195
<211> LENGTH: 25
<212> TYPE: RNA
<213> ORGANISM: artificial
<220> FEATURE:
<223> OTHER INFORMATION: oligonucleotide

<400> SEQUENCE: 195
uuucuaguuu ggagauggca guuuc                                          25

<210> SEQ ID NO 196
<211> LENGTH: 25
<212> TYPE: RNA
<213> ORGANISM: artificial
<220> FEATURE:
<223> OTHER INFORMATION: oligonucleotide

<400> SEQUENCE: 196
uucuaguuug gagauggcag uuucc                                          25

<210> SEQ ID NO 197
<211> LENGTH: 25
<212> TYPE: RNA
<213> ORGANISM: artificial
<220> FEATURE:

<223> OTHER INFORMATION: oligonucleotide

<400> SEQUENCE: 197
ucuaguuugg agauggcagu uuccu                                              25

<210> SEQ ID NO 198
<211> LENGTH: 25
<212> TYPE: RNA
<213> ORGANISM: artificial
<220> FEATURE:
<223> OTHER INFORMATION: oligonucleotide

<400> SEQUENCE: 198
cuaguuugga gauggcaguu uccuu                                              25

<210> SEQ ID NO 199
<211> LENGTH: 25
<212> TYPE: RNA
<213> ORGANISM: artificial
<220> FEATURE:
<223> OTHER INFORMATION: oligonucleotide

<400> SEQUENCE: 199
uaguuuggag auggcaguuu ccuua                                              25

<210> SEQ ID NO 200
<211> LENGTH: 25
<212> TYPE: RNA
<213> ORGANISM: artificial
<220> FEATURE:
<223> OTHER INFORMATION: oligonucleotide

<400> SEQUENCE: 200
aguuuggaga uggcaguuuc cuuag                                              25

<210> SEQ ID NO 201
<211> LENGTH: 25
<212> TYPE: RNA
<213> ORGANISM: artificial
<220> FEATURE:
<223> OTHER INFORMATION: oligonucleotide

<400> SEQUENCE: 201
guuuggagau ggcaguuucc uuagu                                              25

<210> SEQ ID NO 202
<211> LENGTH: 25
<212> TYPE: RNA
<213> ORGANISM: artificial
<220> FEATURE:
<223> OTHER INFORMATION: oligonucleotide

<400> SEQUENCE: 202
uuuggagaug gcaguuuccu uagua                                              25

<210> SEQ ID NO 203
<211> LENGTH: 25
<212> TYPE: RNA
<213> ORGANISM: artificial
<220> FEATURE:
<223> OTHER INFORMATION: oligonucleotide

<400> SEQUENCE: 203
uuggagaugg caguuuccuu aguaa                                              25

```
<210> SEQ ID NO 204
<211> LENGTH: 25
<212> TYPE: RNA
<213> ORGANISM: artificial
<220> FEATURE:
<223> OTHER INFORMATION: oligonucleotide

<400> SEQUENCE: 204
uggagauggc aguuccuua guaac                                          25

<210> SEQ ID NO 205
<211> LENGTH: 25
<212> TYPE: RNA
<213> ORGANISM: artificial
<220> FEATURE:
<223> OTHER INFORMATION: oligonucleotide

<400> SEQUENCE: 205
gagauggcag uuccuuagu aacca                                          25

<210> SEQ ID NO 206
<211> LENGTH: 25
<212> TYPE: RNA
<213> ORGANISM: artificial
<220> FEATURE:
<223> OTHER INFORMATION: oligonucleotide

<400> SEQUENCE: 206
agauggcagu uccuuagua accac                                          25

<210> SEQ ID NO 207
<211> LENGTH: 25
<212> TYPE: RNA
<213> ORGANISM: artificial
<220> FEATURE:
<223> OTHER INFORMATION: oligonucleotide

<400> SEQUENCE: 207
gauggcaguu uccuuaguaa ccaca                                         25

<210> SEQ ID NO 208
<211> LENGTH: 25
<212> TYPE: RNA
<213> ORGANISM: artificial
<220> FEATURE:
<223> OTHER INFORMATION: oligonucleotide

<400> SEQUENCE: 208
auggcaguuu ccuuaguaac cacag                                         25

<210> SEQ ID NO 209
<211> LENGTH: 25
<212> TYPE: RNA
<213> ORGANISM: artificial
<220> FEATURE:
<223> OTHER INFORMATION: oligonucleotide

<400> SEQUENCE: 209
uggcaguuuc cuuaguaacc acagg                                         25

<210> SEQ ID NO 210
<211> LENGTH: 25
<212> TYPE: RNA
<213> ORGANISM: artificial
<220> FEATURE:
<223> OTHER INFORMATION: oligonucleotide
```

```
<400> SEQUENCE: 210
ggcaguuucc uuaguaacca caggu                                    25

<210> SEQ ID NO 211
<211> LENGTH: 25
<212> TYPE: RNA
<213> ORGANISM: artificial
<220> FEATURE:
<223> OTHER INFORMATION: oligonucleotide

<400> SEQUENCE: 211
gcaguuuccu uaguaaccac agguu                                    25

<210> SEQ ID NO 212
<211> LENGTH: 25
<212> TYPE: RNA
<213> ORGANISM: artificial
<220> FEATURE:
<223> OTHER INFORMATION: oligonucleotide

<400> SEQUENCE: 212
caguuuccuu aguaaccaca gguug                                    25

<210> SEQ ID NO 213
<211> LENGTH: 25
<212> TYPE: RNA
<213> ORGANISM: artificial
<220> FEATURE:
<223> OTHER INFORMATION: oligonucleotide

<400> SEQUENCE: 213
aguuuccuua guaaccacag guugu                                    25

<210> SEQ ID NO 214
<211> LENGTH: 25
<212> TYPE: RNA
<213> ORGANISM: artificial
<220> FEATURE:
<223> OTHER INFORMATION: oligonucleotide

<400> SEQUENCE: 214
guuuccuuag uaaccacagg uugug                                    25

<210> SEQ ID NO 215
<211> LENGTH: 25
<212> TYPE: RNA
<213> ORGANISM: artificial
<220> FEATURE:
<223> OTHER INFORMATION: oligonucleotide

<400> SEQUENCE: 215
uuuccuuagu aaccacaggu ugugu                                    25

<210> SEQ ID NO 216
<211> LENGTH: 25
<212> TYPE: RNA
<213> ORGANISM: artificial
<220> FEATURE:
<223> OTHER INFORMATION: oligonucleotide

<400> SEQUENCE: 216
uuccuuagua accacagguu guguc                                    25

<210> SEQ ID NO 217
<211> LENGTH: 25
```

```
<212> TYPE: RNA
<213> ORGANISM: artificial
<220> FEATURE:
<223> OTHER INFORMATION: oligonucleotide

<400> SEQUENCE: 217
uccuuaguaa ccacagguug uguca                                   25

<210> SEQ ID NO 218
<211> LENGTH: 25
<212> TYPE: RNA
<213> ORGANISM: artificial
<220> FEATURE:
<223> OTHER INFORMATION: oligonucleotide

<400> SEQUENCE: 218
ccuuaguaac cacagguugu gucac                                   25

<210> SEQ ID NO 219
<211> LENGTH: 25
<212> TYPE: RNA
<213> ORGANISM: artificial
<220> FEATURE:
<223> OTHER INFORMATION: oligonucleotide

<400> SEQUENCE: 219
cuuaguaacc acagguugug ucacc                                   25

<210> SEQ ID NO 220
<211> LENGTH: 25
<212> TYPE: RNA
<213> ORGANISM: artificial
<220> FEATURE:
<223> OTHER INFORMATION: oligonucleotide

<400> SEQUENCE: 220
uuaguaacca cagguugugu cacca                                   25

<210> SEQ ID NO 221
<211> LENGTH: 25
<212> TYPE: RNA
<213> ORGANISM: artificial
<220> FEATURE:
<223> OTHER INFORMATION: oligonucleotide

<400> SEQUENCE: 221
uaguaaccac agguuguguc accag                                   25

<210> SEQ ID NO 222
<211> LENGTH: 25
<212> TYPE: RNA
<213> ORGANISM: artificial
<220> FEATURE:
<223> OTHER INFORMATION: oligonucleotide

<400> SEQUENCE: 222
aguaaccaca gguuguguca ccaga                                   25

<210> SEQ ID NO 223
<211> LENGTH: 25
<212> TYPE: RNA
<213> ORGANISM: artificial
<220> FEATURE:
<223> OTHER INFORMATION: oligonucleotide

<400> SEQUENCE: 223
```
guaaccacag guugugucac cagag                                          25

<210> SEQ ID NO 224
<211> LENGTH: 25
<212> TYPE: RNA
<213> ORGANISM: artificial
<220> FEATURE:
<223> OTHER INFORMATION: oligonucleotide

<400> SEQUENCE: 224
uaaccacagg uugugucacc agagu                                          25

<210> SEQ ID NO 225
<211> LENGTH: 25
<212> TYPE: RNA
<213> ORGANISM: artificial
<220> FEATURE:
<223> OTHER INFORMATION: oligonucleotide

<400> SEQUENCE: 225
aaccacaggu ugugucacca gagua                                          25

<210> SEQ ID NO 226
<211> LENGTH: 25
<212> TYPE: RNA
<213> ORGANISM: artificial
<220> FEATURE:
<223> OTHER INFORMATION: oligonucleotide

<400> SEQUENCE: 226
accacagguu gugucaccag aguaa                                          25

<210> SEQ ID NO 227
<211> LENGTH: 25
<212> TYPE: RNA
<213> ORGANISM: artificial
<220> FEATURE:
<223> OTHER INFORMATION: oligonucleotide

<400> SEQUENCE: 227
ccacagguug ugucaccaga guaac                                          25

<210> SEQ ID NO 228
<211> LENGTH: 25
<212> TYPE: RNA
<213> ORGANISM: artificial
<220> FEATURE:
<223> OTHER INFORMATION: oligonucleotide

<400> SEQUENCE: 228
cacagguugu gucaccagag uaaca                                          25

<210> SEQ ID NO 229
<211> LENGTH: 25
<212> TYPE: RNA
<213> ORGANISM: artificial
<220> FEATURE:
<223> OTHER INFORMATION: oligonucleotide

<400> SEQUENCE: 229
acagguugug ucaccagagu aacag                                          25

<210> SEQ ID NO 230
<211> LENGTH: 25
<212> TYPE: RNA
<213> ORGANISM: artificial

```
<220> FEATURE:
<223> OTHER INFORMATION: oligonucleotide

<400> SEQUENCE: 230
cagguugugu caccagagua acagu                                              25

<210> SEQ ID NO 231
<211> LENGTH: 25
<212> TYPE: RNA
<213> ORGANISM: artificial
<220> FEATURE:
<223> OTHER INFORMATION: oligonucleotide

<400> SEQUENCE: 231
agguuguguc accagaguaa caguc                                              25

<210> SEQ ID NO 232
<211> LENGTH: 25
<212> TYPE: RNA
<213> ORGANISM: artificial
<220> FEATURE:
<223> OTHER INFORMATION: oligonucleotide

<400> SEQUENCE: 232
gguuguguca ccagaguaac agucu                                              25

<210> SEQ ID NO 233
<211> LENGTH: 25
<212> TYPE: RNA
<213> ORGANISM: artificial
<220> FEATURE:
<223> OTHER INFORMATION: oligonucleotide

<400> SEQUENCE: 233
guugugucac cagaguaaca gucug                                              25

<210> SEQ ID NO 234
<211> LENGTH: 25
<212> TYPE: RNA
<213> ORGANISM: artificial
<220> FEATURE:
<223> OTHER INFORMATION: oligonucleotide

<400> SEQUENCE: 234
uugugucacc agaguaacag ucuga                                              25

<210> SEQ ID NO 235
<211> LENGTH: 25
<212> TYPE: RNA
<213> ORGANISM: artificial
<220> FEATURE:
<223> OTHER INFORMATION: oligonucleotide

<400> SEQUENCE: 235
ugugucacca gaguaacagu cugag                                              25

<210> SEQ ID NO 236
<211> LENGTH: 25
<212> TYPE: RNA
<213> ORGANISM: artificial
<220> FEATURE:
<223> OTHER INFORMATION: oligonucleotide

<400> SEQUENCE: 236
gugucaccag aguaacaguc ugagu                                              25
```

```
<210> SEQ ID NO 237
<211> LENGTH: 25
<212> TYPE: RNA
<213> ORGANISM: artificial
<220> FEATURE:
<223> OTHER INFORMATION: oligonucleotide

<400> SEQUENCE: 237
ugucaccaga guaacagucu gagua                                              25

<210> SEQ ID NO 238
<211> LENGTH: 25
<212> TYPE: RNA
<213> ORGANISM: artificial
<220> FEATURE:
<223> OTHER INFORMATION: oligonucleotide

<400> SEQUENCE: 238
gucaccagag uaacagucug aguag                                              25

<210> SEQ ID NO 239
<211> LENGTH: 25
<212> TYPE: RNA
<213> ORGANISM: artificial
<220> FEATURE:
<223> OTHER INFORMATION: oligonucleotide

<400> SEQUENCE: 239
ucaccagagu aacagucuga guagg                                              25

<210> SEQ ID NO 240
<211> LENGTH: 25
<212> TYPE: RNA
<213> ORGANISM: artificial
<220> FEATURE:
<223> OTHER INFORMATION: oligonucleotide

<400> SEQUENCE: 240
caccagagua acagucugag uagga                                              25

<210> SEQ ID NO 241
<211> LENGTH: 25
<212> TYPE: RNA
<213> ORGANISM: artificial
<220> FEATURE:
<223> OTHER INFORMATION: oligonucleotide

<400> SEQUENCE: 241
accagaguaa cagucugagu aggag                                              25

<210> SEQ ID NO 242
<211> LENGTH: 25
<212> TYPE: RNA
<213> ORGANISM: artificial
<220> FEATURE:
<223> OTHER INFORMATION: oligonucleotide

<400> SEQUENCE: 242
agccucuuga uugcuggucu uguuu                                              25

<210> SEQ ID NO 243
<211> LENGTH: 25
<212> TYPE: RNA
<213> ORGANISM: artificial
<220> FEATURE:
<223> OTHER INFORMATION: oligonucleotide
```

```
<400> SEQUENCE: 243
gccucuugau ugcuggucuu guuuu                                          25

<210> SEQ ID NO 244
<211> LENGTH: 25
<212> TYPE: RNA
<213> ORGANISM: artificial
<220> FEATURE:
<223> OTHER INFORMATION: oligonucleotide

<400> SEQUENCE: 244
ccucuugauu gcuggucuug uuuuu                                          25

<210> SEQ ID NO 245
<211> LENGTH: 20
<212> TYPE: RNA
<213> ORGANISM: artificial
<220> FEATURE:
<223> OTHER INFORMATION: oligonucleotide

<400> SEQUENCE: 245
ccucuugauu gcuggucuug                                                20

<210> SEQ ID NO 246
<211> LENGTH: 25
<212> TYPE: RNA
<213> ORGANISM: artificial
<220> FEATURE:
<223> OTHER INFORMATION: oligonucleotide

<400> SEQUENCE: 246
cucuugauug cuggucuugu uuuuc                                          25

<210> SEQ ID NO 247
<211> LENGTH: 25
<212> TYPE: RNA
<213> ORGANISM: artificial
<220> FEATURE:
<223> OTHER INFORMATION: oligonucleotide

<400> SEQUENCE: 247
ucuugauugc uggucuuguu uuuca                                          25

<210> SEQ ID NO 248
<211> LENGTH: 25
<212> TYPE: RNA
<213> ORGANISM: artificial
<220> FEATURE:
<223> OTHER INFORMATION: oligonucleotide

<400> SEQUENCE: 248
cuugauugcu ggucuuguuu uucaa                                          25

<210> SEQ ID NO 249
<211> LENGTH: 25
<212> TYPE: RNA
<213> ORGANISM: artificial
<220> FEATURE:
<223> OTHER INFORMATION: oligonucleotide

<400> SEQUENCE: 249
uugauugcug gucuuguuuu ucaaa                                          25

<210> SEQ ID NO 250
```

```
<211> LENGTH: 25
<212> TYPE: RNA
<213> ORGANISM: artificial
<220> FEATURE:
<223> OTHER INFORMATION: oligonucleotide

<400> SEQUENCE: 250
ugauugcugg ucuuguuuuu caaau                                          25

<210> SEQ ID NO 251
<211> LENGTH: 25
<212> TYPE: RNA
<213> ORGANISM: artificial
<220> FEATURE:
<223> OTHER INFORMATION: oligonucleotide

<400> SEQUENCE: 251
gauugcuggu cuuguuuuc aaauu                                           25

<210> SEQ ID NO 252
<211> LENGTH: 20
<212> TYPE: RNA
<213> ORGANISM: artificial
<220> FEATURE:
<223> OTHER INFORMATION: oligonucleotide

<400> SEQUENCE: 252
gauugcuggu cuuguuuuc                                                 20

<210> SEQ ID NO 253
<211> LENGTH: 25
<212> TYPE: RNA
<213> ORGANISM: artificial
<220> FEATURE:
<223> OTHER INFORMATION: oligonucleotide

<400> SEQUENCE: 253
auugcugguc uuguuuuca aauuu                                           25

<210> SEQ ID NO 254
<211> LENGTH: 25
<212> TYPE: RNA
<213> ORGANISM: artificial
<220> FEATURE:
<223> OTHER INFORMATION: oligonucleotide

<400> SEQUENCE: 254
uugcuggucu uguuuucaa auuuu                                           25

<210> SEQ ID NO 255
<211> LENGTH: 25
<212> TYPE: RNA
<213> ORGANISM: artificial
<220> FEATURE:
<223> OTHER INFORMATION: oligonucleotide

<400> SEQUENCE: 255
ugcuggucuu guuuucaaa uuuug                                           25

<210> SEQ ID NO 256
<211> LENGTH: 25
<212> TYPE: RNA
<213> ORGANISM: artificial
<220> FEATURE:
<223> OTHER INFORMATION: oligonucleotide

<400> SEQUENCE: 256
```
gcuggucuug uuuuucaaau uuugg                                              25

<210> SEQ ID NO 257
<211> LENGTH: 25
<212> TYPE: RNA
<213> ORGANISM: artificial
<220> FEATURE:
<223> OTHER INFORMATION: oligonucleotide

<400> SEQUENCE: 257
cuggucuugu uuucaaauu uuggg                                               25

<210> SEQ ID NO 258
<211> LENGTH: 25
<212> TYPE: RNA
<213> ORGANISM: artificial
<220> FEATURE:
<223> OTHER INFORMATION: oligonucleotide

<400> SEQUENCE: 258
uggucuuguu uuucaaauuu ugggc                                              25

<210> SEQ ID NO 259
<211> LENGTH: 25
<212> TYPE: RNA
<213> ORGANISM: artificial
<220> FEATURE:
<223> OTHER INFORMATION: oligonucleotide

<400> SEQUENCE: 259
ggucuuguuu uucaaauuuu gggca                                              25

<210> SEQ ID NO 260
<211> LENGTH: 25
<212> TYPE: RNA
<213> ORGANISM: artificial
<220> FEATURE:
<223> OTHER INFORMATION: oligonucleotide

<400> SEQUENCE: 260
gucuuguuuu ucaaauuuug ggcag                                              25

<210> SEQ ID NO 261
<211> LENGTH: 25
<212> TYPE: RNA
<213> ORGANISM: artificial
<220> FEATURE:
<223> OTHER INFORMATION: oligonucleotide

<400> SEQUENCE: 261
ucuuguuuuu caaauuuugg gcagc                                              25

<210> SEQ ID NO 262
<211> LENGTH: 25
<212> TYPE: RNA
<213> ORGANISM: artificial
<220> FEATURE:
<223> OTHER INFORMATION: oligonucleotide

<400> SEQUENCE: 262
cuuguuuuuc aaauuuuggg cagcg                                              25

<210> SEQ ID NO 263
<211> LENGTH: 25
<212> TYPE: RNA

<210> SEQ ID NO 263
<211> LENGTH: 25
<212> TYPE: RNA
<213> ORGANISM: artificial
<220> FEATURE:
<223> OTHER INFORMATION: oligonucleotide

<400> SEQUENCE: 263
uuguuuuuca aauuuugggc agcgg                                   25

<210> SEQ ID NO 264
<211> LENGTH: 25
<212> TYPE: RNA
<213> ORGANISM: artificial
<220> FEATURE:
<223> OTHER INFORMATION: oligonucleotide

<400> SEQUENCE: 264
uguuuuucaa auuuugggca gcggu                                   25

<210> SEQ ID NO 265
<211> LENGTH: 25
<212> TYPE: RNA
<213> ORGANISM: artificial
<220> FEATURE:
<223> OTHER INFORMATION: oligonucleotide

<400> SEQUENCE: 265
guuuuucaaa uuuugggcag cggua                                   25

<210> SEQ ID NO 266
<211> LENGTH: 25
<212> TYPE: RNA
<213> ORGANISM: artificial
<220> FEATURE:
<223> OTHER INFORMATION: oligonucleotide

<400> SEQUENCE: 266
uuuuucaaau uuugggcagc gguaa                                   25

<210> SEQ ID NO 267
<211> LENGTH: 25
<212> TYPE: RNA
<213> ORGANISM: artificial
<220> FEATURE:
<223> OTHER INFORMATION: oligonucleotide

<400> SEQUENCE: 267
uuuucaaauu uugggcagcg guaau                                   25

<210> SEQ ID NO 268
<211> LENGTH: 25
<212> TYPE: RNA
<213> ORGANISM: artificial
<220> FEATURE:
<223> OTHER INFORMATION: oligonucleotide

<400> SEQUENCE: 268
uuucaaauuu ugggcagcgg uaaug                                   25

<210> SEQ ID NO 269
<211> LENGTH: 25
<212> TYPE: RNA
<213> ORGANISM: artificial
<220> FEATURE:
<223> OTHER INFORMATION: oligonucleotide

<400> SEQUENCE: 269
uucaaauuuu gggcagcggu aauga                                   25

<210> SEQ ID NO 270
<211> LENGTH: 25
<212> TYPE: RNA
<213> ORGANISM: artificial
<220> FEATURE:
<223> OTHER INFORMATION: oligonucleotide

<400> SEQUENCE: 270
ucaaauuuug ggcagcggua augag                              25

<210> SEQ ID NO 271
<211> LENGTH: 25
<212> TYPE: RNA
<213> ORGANISM: artificial
<220> FEATURE:
<223> OTHER INFORMATION: oligonucleotide

<400> SEQUENCE: 271
caaauuuugg gcagcgguaa ugagu                              25

<210> SEQ ID NO 272
<211> LENGTH: 25
<212> TYPE: RNA
<213> ORGANISM: artificial
<220> FEATURE:
<223> OTHER INFORMATION: oligonucleotide

<400> SEQUENCE: 272
aaauuugggg cagcgguaau gaguu                              25

<210> SEQ ID NO 273
<211> LENGTH: 25
<212> TYPE: RNA
<213> ORGANISM: artificial
<220> FEATURE:
<223> OTHER INFORMATION: oligonucleotide

<400> SEQUENCE: 273 aauuugggc agcgguaaug aguuc                               25

<210> SEQ ID NO 274
<211> LENGTH: 25
<212> TYPE: RNA
<213> ORGANISM: artificial
<220> FEATURE:
<223> OTHER INFORMATION: oligonucleotide

<400> SEQUENCE: 274 auuugggca gcgguaauga guucu                               25

<210> SEQ ID NO 275
<211> LENGTH: 25
<212> TYPE: RNA
<213> ORGANISM: artificial
<220> FEATURE:
<223> OTHER INFORMATION: oligonucleotide

<400> SEQUENCE: 275 uuugggcag cgguaaugag uucuu                               25

<210> SEQ ID NO 276
<211> LENGTH: 25
<212> TYPE: RNA
<213> ORGANISM: artificial
<220> FEATURE:

```
<223> OTHER INFORMATION: oligonucleotide

<400> SEQUENCE: 276
uuugggcagc gguaaugagu ucuuc                                    25

<210> SEQ ID NO 277
<211> LENGTH: 25
<212> TYPE: RNA
<213> ORGANISM: artificial
<220> FEATURE:
<223> OTHER INFORMATION: oligonucleotide

<400> SEQUENCE: 277
uugggcagcg guaaugaguu cuucc                                    25

<210> SEQ ID NO 278
<211> LENGTH: 25
<212> TYPE: RNA
<213> ORGANISM: artificial
<220> FEATURE:
<223> OTHER INFORMATION: oligonucleotide

<400> SEQUENCE: 278
ugggcagcgg uaaugaguuc uucca                                    25

<210> SEQ ID NO 279
<211> LENGTH: 25
<212> TYPE: RNA
<213> ORGANISM: artificial
<220> FEATURE:
<223> OTHER INFORMATION: oligonucleotide

<400> SEQUENCE: 279
gggcagcggu aaugaguucu uccaa                                    25

<210> SEQ ID NO 280
<211> LENGTH: 25
<212> TYPE: RNA
<213> ORGANISM: artificial
<220> FEATURE:
<223> OTHER INFORMATION: oligonucleotide

<400> SEQUENCE: 280
ggcagcggua augaguucuu ccaac                                    25

<210> SEQ ID NO 281
<211> LENGTH: 25
<212> TYPE: RNA
<213> ORGANISM: artificial
<220> FEATURE:
<223> OTHER INFORMATION: oligonucleotide

<400> SEQUENCE: 281
gcagcgguaa ugaguucuuc caacu                                    25

<210> SEQ ID NO 282
<211> LENGTH: 25
<212> TYPE: RNA
<213> ORGANISM: artificial
<220> FEATURE:
<223> OTHER INFORMATION: oligonucleotide

<400> SEQUENCE: 282
cagcgguaau gaguucuucc aacug                                    25
```

```
<210> SEQ ID NO 283
<211> LENGTH: 25
<212> TYPE: RNA
<213> ORGANISM: artificial
<220> FEATURE:
<223> OTHER INFORMATION: oligonucleotide

<400> SEQUENCE: 283
agcgguaaug aguucuucca acugg                                               25

<210> SEQ ID NO 284
<211> LENGTH: 25
<212> TYPE: RNA
<213> ORGANISM: artificial
<220> FEATURE:
<223> OTHER INFORMATION: oligonucleotide

<400> SEQUENCE: 284
gcgguaauga guucuuccaa cuggg                                               25

<210> SEQ ID NO 285
<211> LENGTH: 25
<212> TYPE: RNA
<213> ORGANISM: artificial
<220> FEATURE:
<223> OTHER INFORMATION: oligonucleotide

<400> SEQUENCE: 285
cgguaaugag uucuuccaac ugggg                                               25

<210> SEQ ID NO 286
<211> LENGTH: 25
<212> TYPE: RNA
<213> ORGANISM: artificial
<220> FEATURE:
<223> OTHER INFORMATION: oligonucleotide

<400> SEQUENCE: 286
gguaaugagu ucuuccaacu gggga                                               25

<210> SEQ ID NO 287
<211> LENGTH: 22
<212> TYPE: RNA
<213> ORGANISM: artificial
<220> FEATURE:
<223> OTHER INFORMATION: oligonucleotide

<400> SEQUENCE: 287
gguaaugagu ucuuccaacu gg                                                  22

<210> SEQ ID NO 288
<211> LENGTH: 25
<212> TYPE: RNA
<213> ORGANISM: artificial
<220> FEATURE:
<223> OTHER INFORMATION: oligonucleotide

<400> SEQUENCE: 288
guaaugaguu cuuccaacug ggac                                                25

<210> SEQ ID NO 289
<211> LENGTH: 25
<212> TYPE: RNA
<213> ORGANISM: artificial
<220> FEATURE:
<223> OTHER INFORMATION: oligonucleotide
```

```
<400> SEQUENCE: 289
uaaugaguuc uuccaacugg ggacg                                      25

<210> SEQ ID NO 290
<211> LENGTH: 25
<212> TYPE: RNA
<213> ORGANISM: artificial
<220> FEATURE:
<223> OTHER INFORMATION: oligonucleotide

<400> SEQUENCE: 290
aaugaguucu uccaacuggg gacgc                                      25

<210> SEQ ID NO 291
<211> LENGTH: 25
<212> TYPE: RNA
<213> ORGANISM: artificial
<220> FEATURE:
<223> OTHER INFORMATION: oligonucleotide

<400> SEQUENCE: 291
augaguucuu ccaacugggg acgcc                                      25

<210> SEQ ID NO 292
<211> LENGTH: 25
<212> TYPE: RNA
<213> ORGANISM: artificial
<220> FEATURE:
<223> OTHER INFORMATION: oligonucleotide

<400> SEQUENCE: 292
ugaguucuuc caacugggga cgccu                                      25

<210> SEQ ID NO 293
<211> LENGTH: 25
<212> TYPE: RNA
<213> ORGANISM: artificial
<220> FEATURE:
<223> OTHER INFORMATION: oligonucleotide

<400> SEQUENCE: 293
gaguucuucc aacugggac gccuc                                       25

<210> SEQ ID NO 294
<211> LENGTH: 25
<212> TYPE: RNA
<213> ORGANISM: artificial
<220> FEATURE:
<223> OTHER INFORMATION: oligonucleotide

<400> SEQUENCE: 294
aguucuucca acugggacg ccucu                                       25

<210> SEQ ID NO 295
<211> LENGTH: 25
<212> TYPE: RNA
<213> ORGANISM: artificial
<220> FEATURE:
<223> OTHER INFORMATION: oligonucleotide

<400> SEQUENCE: 295
guucuuccaa cugggacgc cucug                                       25

<210> SEQ ID NO 296
<211> LENGTH: 25
```

```
<212> TYPE: RNA
<213> ORGANISM: artificial
<220> FEATURE:
<223> OTHER INFORMATION: oligonucleotide

<400> SEQUENCE: 296
uucuuccaac ugggggacgcc ucugu                                25

<210> SEQ ID NO 297
<211> LENGTH: 25
<212> TYPE: RNA
<213> ORGANISM: artificial
<220> FEATURE:
<223> OTHER INFORMATION: oligonucleotide

<400> SEQUENCE: 297
ucuuccaacu ggggacgccu cuguu                                25

<210> SEQ ID NO 298
<211> LENGTH: 25
<212> TYPE: RNA
<213> ORGANISM: artificial
<220> FEATURE:
<223> OTHER INFORMATION: oligonucleotide

<400> SEQUENCE: 298
cuuccaacug gggacgccuc uguuc                                25

<210> SEQ ID NO 299
<211> LENGTH: 25
<212> TYPE: RNA
<213> ORGANISM: artificial
<220> FEATURE:
<223> OTHER INFORMATION: oligonucleotide

<400> SEQUENCE: 299
uuccaacugg ggacgccucu guucc                                25

<210> SEQ ID NO 300
<211> LENGTH: 25
<212> TYPE: RNA
<213> ORGANISM: artificial
<220> FEATURE:
<223> OTHER INFORMATION: oligonucleotide

<400> SEQUENCE: 300
uccaacuggg gacgccucug uucca                                25

<210> SEQ ID NO 301
<211> LENGTH: 25
<212> TYPE: RNA
<213> ORGANISM: artificial
<220> FEATURE:
<223> OTHER INFORMATION: oligonucleotide

<400> SEQUENCE: 301
ccaacugggg acgccucugu uccaa                                25

<210> SEQ ID NO 302
<211> LENGTH: 25
<212> TYPE: RNA
<213> ORGANISM: artificial
<220> FEATURE:
<223> OTHER INFORMATION: oligonucleotide

<400> SEQUENCE: 302
```

-continued caacugggga cgccucuguu ccaaa       25

<210> SEQ ID NO 303
<211> LENGTH: 25
<212> TYPE: RNA
<213> ORGANISM: artificial
<220> FEATURE:
<223> OTHER INFORMATION: oligonucleotide

<400> SEQUENCE: 303 aacugggac gccucuguuc caaau        25

<210> SEQ ID NO 304
<211> LENGTH: 25
<212> TYPE: RNA
<213> ORGANISM: artificial
<220> FEATURE:
<223> OTHER INFORMATION: oligonucleotide

<400> SEQUENCE: 304 acugggacg ccucuguucc aaauc        25

<210> SEQ ID NO 305
<211> LENGTH: 25
<212> TYPE: RNA
<213> ORGANISM: artificial
<220> FEATURE:
<223> OTHER INFORMATION: oligonucleotide

<400> SEQUENCE: 305
cuggggacgc cucuguucca aaucc       25

<210> SEQ ID NO 306
<211> LENGTH: 25
<212> TYPE: RNA
<213> ORGANISM: artificial
<220> FEATURE:
<223> OTHER INFORMATION: oligonucleotide

<400> SEQUENCE: 306
uggggacgcc ucuguuccaa auccu       25

<210> SEQ ID NO 307
<211> LENGTH: 25
<212> TYPE: RNA
<213> ORGANISM: artificial
<220> FEATURE:
<223> OTHER INFORMATION: oligonucleotide

<400> SEQUENCE: 307
ggggacgccu cuguuccaaa uccug       25

<210> SEQ ID NO 308
<211> LENGTH: 25
<212> TYPE: RNA
<213> ORGANISM: artificial
<220> FEATURE:
<223> OTHER INFORMATION: oligonucleotide

<400> SEQUENCE: 308
gggacgccuc uguuccaaau ccugc       25

<210> SEQ ID NO 309
<211> LENGTH: 25
<212> TYPE: RNA
<213> ORGANISM: artificial

```
<220> FEATURE:
<223> OTHER INFORMATION: oligonucleotide

<400> SEQUENCE: 309
ggacgccucu guuccaaauc cugca                                              25

<210> SEQ ID NO 310
<211> LENGTH: 25
<212> TYPE: RNA
<213> ORGANISM: artificial
<220> FEATURE:
<223> OTHER INFORMATION: oligonucleotide

<400> SEQUENCE: 310
gacgccucug uuccaaaucc ugcau                                              25

<210> SEQ ID NO 311
<211> LENGTH: 25
<212> TYPE: RNA
<213> ORGANISM: artificial
<220> FEATURE:
<223> OTHER INFORMATION: oligonucleotide

<400> SEQUENCE: 311
cucuggccug uccuaagacc ugcuc                                              25

<210> SEQ ID NO 312
<211> LENGTH: 25
<212> TYPE: RNA
<213> ORGANISM: artificial
<220> FEATURE:
<223> OTHER INFORMATION: oligonucleotide

<400> SEQUENCE: 312
ucuggccugu ccuaagaccu gcuca                                              25

<210> SEQ ID NO 313

<400> SEQUENCE: 313

000

<210> SEQ ID NO 314
<211> LENGTH: 25
<212> TYPE: RNA
<213> ORGANISM: artificial
<220> FEATURE:
<223> OTHER INFORMATION: oligonucleotide

<400> SEQUENCE: 314
uggccugucc uaagaccugc ucagc                                              25

<210> SEQ ID NO 315
<211> LENGTH: 25
<212> TYPE: RNA
<213> ORGANISM: artificial
<220> FEATURE:
<223> OTHER INFORMATION: oligonucleotide

<400> SEQUENCE: 315
ggccuguccu aagaccugcu cagcu                                              25

<210> SEQ ID NO 316
<211> LENGTH: 25
<212> TYPE: RNA
<213> ORGANISM: artificial
```

```
<220> FEATURE:
<223> OTHER INFORMATION: oligonucleotide

<400> SEQUENCE: 316
gccuguccua agaccugcuc agcuu                                              25

<210> SEQ ID NO 317
<211> LENGTH: 25
<212> TYPE: RNA
<213> ORGANISM: artificial
<220> FEATURE:
<223> OTHER INFORMATION: oligonucleotide

<400> SEQUENCE: 317
ccuguccuaa gaccugcuca gcuuc                                              25

<210> SEQ ID NO 318
<211> LENGTH: 25
<212> TYPE: RNA
<213> ORGANISM: artificial
<220> FEATURE:
<223> OTHER INFORMATION: oligonucleotide

<400> SEQUENCE: 318
cuguccuaag accugcucag cuucu                                              25

<210> SEQ ID NO 319
<211> LENGTH: 25
<212> TYPE: RNA
<213> ORGANISM: artificial
<220> FEATURE:
<223> OTHER INFORMATION: oligonucleotide

<400> SEQUENCE: 319
uguccuaaga ccugcucagc uucuu                                              25

<210> SEQ ID NO 320
<211> LENGTH: 25
<212> TYPE: RNA
<213> ORGANISM: artificial
<220> FEATURE:
<223> OTHER INFORMATION: oligonucleotide

<400> SEQUENCE: 320
guccuaagac cugcucagcu ucuuc                                              25

<210> SEQ ID NO 321
<211> LENGTH: 25
<212> TYPE: RNA
<213> ORGANISM: artificial
<220> FEATURE:
<223> OTHER INFORMATION: oligonucleotide

<400> SEQUENCE: 321
uccuaagacc ugcucagcuu cuucc                                              25

<210> SEQ ID NO 322
<211> LENGTH: 25
<212> TYPE: RNA
<213> ORGANISM: artificial
<220> FEATURE:
<223> OTHER INFORMATION: oligonucleotide

<400> SEQUENCE: 322
ccuaagaccu gcucagcuuc uuccu                                              25
```

<210> SEQ ID NO 323
<211> LENGTH: 25
<212> TYPE: RNA
<213> ORGANISM: artificial
<220> FEATURE:
<223> OTHER INFORMATION: oligonucleotide

<400> SEQUENCE: 323
cuaagaccug cucagcuucu uccuu                                    25

<210> SEQ ID NO 324
<211> LENGTH: 25
<212> TYPE: RNA
<213> ORGANISM: artificial
<220> FEATURE:
<223> OTHER INFORMATION: oligonucleotide

<400> SEQUENCE: 324
uaagaccugc ucagcuucuu ccuua                                    25

<210> SEQ ID NO 325
<211> LENGTH: 25
<212> TYPE: RNA
<213> ORGANISM: artificial
<220> FEATURE:
<223> OTHER INFORMATION: oligonucleotide

<400> SEQUENCE: 325
aagaccugcu cagcuucuuc cuuag                                    25

<210> SEQ ID NO 326
<211> LENGTH: 25
<212> TYPE: RNA
<213> ORGANISM: artificial
<220> FEATURE:
<223> OTHER INFORMATION: oligonucleotide

<400> SEQUENCE: 326
agaccugcuc agcuucuucc uuagc                                    25

<210> SEQ ID NO 327
<211> LENGTH: 25
<212> TYPE: RNA
<213> ORGANISM: artificial
<220> FEATURE:
<223> OTHER INFORMATION: oligonucleotide

<400> SEQUENCE: 327
gaccugcuca gcuucuuccu uagcu                                    25

<210> SEQ ID NO 328
<211> LENGTH: 25
<212> TYPE: RNA
<213> ORGANISM: artificial
<220> FEATURE:
<223> OTHER INFORMATION: oligonucleotide

<400> SEQUENCE: 328
accugcucag cuucuuccuu agcuu                                    25

<210> SEQ ID NO 329
<211> LENGTH: 25
<212> TYPE: RNA
<213> ORGANISM: artificial
<220> FEATURE:
<223> OTHER INFORMATION: oligonucleotide

```
<400> SEQUENCE: 329
ccugcucagc uucuuccuua gcuuc                                              25

<210> SEQ ID NO 330
<211> LENGTH: 25
<212> TYPE: RNA
<213> ORGANISM: artificial
<220> FEATURE:
<223> OTHER INFORMATION: oligonucleotide

<400> SEQUENCE: 330
cugcucagcu ucuuccuuag cuucc                                              25

<210> SEQ ID NO 331
<211> LENGTH: 25
<212> TYPE: RNA
<213> ORGANISM: artificial
<220> FEATURE:
<223> OTHER INFORMATION: oligonucleotide

<400> SEQUENCE: 331
ugcucagcuu cuuccuuagc uucca                                              25

<210> SEQ ID NO 332
<211> LENGTH: 25
<212> TYPE: RNA
<213> ORGANISM: artificial
<220> FEATURE:
<223> OTHER INFORMATION: oligonucleotide

<400> SEQUENCE: 332
gcucagcuuc uuccuuagcu uccag                                              25

<210> SEQ ID NO 333
<211> LENGTH: 25
<212> TYPE: RNA
<213> ORGANISM: artificial
<220> FEATURE:
<223> OTHER INFORMATION: oligonucleotide

<400> SEQUENCE: 333
cucagcuucu uccuuagcuu ccagc                                              25

<210> SEQ ID NO 334
<211> LENGTH: 25
<212> TYPE: RNA
<213> ORGANISM: artificial
<220> FEATURE:
<223> OTHER INFORMATION: oligonucleotide

<400> SEQUENCE: 334
ucagcuucuu ccuuagcuuc cagcc                                              25

<210> SEQ ID NO 335
<211> LENGTH: 25
<212> TYPE: RNA
<213> ORGANISM: artificial
<220> FEATURE:
<223> OTHER INFORMATION: oligonucleotide

<400> SEQUENCE: 335
cagcuucuuc cuuagcuucc agcca                                              25

<210> SEQ ID NO 336
```

<211> LENGTH: 25
<212> TYPE: RNA
<213> ORGANISM: artificial
<220> FEATURE:
<223> OTHER INFORMATION: oligonucleotide

<400> SEQUENCE: 336
agcuucuucc uuagcuucca gccau                                  25

<210> SEQ ID NO 337
<211> LENGTH: 25
<212> TYPE: RNA
<213> ORGANISM: artificial
<220> FEATURE:
<223> OTHER INFORMATION: oligonucleotide

<400> SEQUENCE: 337
gcuucuuccu uagcuuccag ccauu                                  25

<210> SEQ ID NO 338
<211> LENGTH: 25
<212> TYPE: RNA
<213> ORGANISM: artificial
<220> FEATURE:
<223> OTHER INFORMATION: oligonucleotide

<400> SEQUENCE: 338
cuucuuccuu agcuuccagc cauug                                  25

<210> SEQ ID NO 339
<211> LENGTH: 25
<212> TYPE: RNA
<213> ORGANISM: artificial
<220> FEATURE:
<223> OTHER INFORMATION: oligonucleotide

<400> SEQUENCE: 339
uucuuccuua gcuuccagcc auugu                                  25

<210> SEQ ID NO 340
<211> LENGTH: 25
<212> TYPE: RNA
<213> ORGANISM: artificial
<220> FEATURE:
<223> OTHER INFORMATION: oligonucleotide

<400> SEQUENCE: 340
ucuuccuuag cuuccagcca uugug                                  25

<210> SEQ ID NO 341
<211> LENGTH: 25
<212> TYPE: RNA
<213> ORGANISM: artificial
<220> FEATURE:
<223> OTHER INFORMATION: oligonucleotide

<400> SEQUENCE: 341
cuuccuuagc uuccagccau ugugu                                  25

<210> SEQ ID NO 342
<211> LENGTH: 25
<212> TYPE: RNA
<213> ORGANISM: artificial
<220> FEATURE:
<223> OTHER INFORMATION: oligonucleotide

<400> SEQUENCE: 342

```
uuccuuagcu uccagccauu guguu                                              25

<210> SEQ ID NO 343
<211> LENGTH: 25
<212> TYPE: RNA
<213> ORGANISM: artificial
<220> FEATURE:
<223> OTHER INFORMATION: oligonucleotide

<400> SEQUENCE: 343
uccuuagcuu ccagccauug uguug                                              25

<210> SEQ ID NO 344
<211> LENGTH: 25
<212> TYPE: RNA
<213> ORGANISM: artificial
<220> FEATURE:
<223> OTHER INFORMATION: oligonucleotide

<400> SEQUENCE: 344
ccuuagcuuc cagccauugu guuga                                              25

<210> SEQ ID NO 345
<211> LENGTH: 25
<212> TYPE: RNA
<213> ORGANISM: artificial
<220> FEATURE:
<223> OTHER INFORMATION: oligonucleotide

<400> SEQUENCE: 345
cuuagcuucc agccauugug uugaa                                              25

<210> SEQ ID NO 346
<211> LENGTH: 25
<212> TYPE: RNA
<213> ORGANISM: artificial
<220> FEATURE:
<223> OTHER INFORMATION: oligonucleotide

<400> SEQUENCE: 346
uuagcuucca gccauugugu ugaau                                              25

<210> SEQ ID NO 347
<211> LENGTH: 25
<212> TYPE: RNA
<213> ORGANISM: artificial
<220> FEATURE:
<223> OTHER INFORMATION: oligonucleotide

<400> SEQUENCE: 347
uagcuuccag ccauuguguu gaauc                                              25

<210> SEQ ID NO 348
<211> LENGTH: 25
<212> TYPE: RNA
<213> ORGANISM: artificial
<220> FEATURE:
<223> OTHER INFORMATION: oligonucleotide

<400> SEQUENCE: 348
agcuuccagc cauuguguug aaucc                                              25

<210> SEQ ID NO 349
<211> LENGTH: 25
<212> TYPE: RNA
```

```
<213> ORGANISM: artificial
<220> FEATURE:
<223> OTHER INFORMATION: oligonucleotide

<400> SEQUENCE: 349
gcuuccagcc auuguguuga auccu                                              25

<210> SEQ ID NO 350
<211> LENGTH: 25
<212> TYPE: RNA
<213> ORGANISM: artificial
<220> FEATURE:
<223> OTHER INFORMATION: oligonucleotide

<400> SEQUENCE: 350
cuuccagcca uuguguugaa uccuu                                              25

<210> SEQ ID NO 351
<211> LENGTH: 25
<212> TYPE: RNA
<213> ORGANISM: artificial
<220> FEATURE:
<223> OTHER INFORMATION: oligonucleotide

<400> SEQUENCE: 351
uuccagccau uguguugaau ccuuu                                              25

<210> SEQ ID NO 352
<211> LENGTH: 25
<212> TYPE: RNA
<213> ORGANISM: artificial
<220> FEATURE:
<223> OTHER INFORMATION: oligonucleotide

<400> SEQUENCE: 352
uccagccauu guguugaauc cuuua                                              25

<210> SEQ ID NO 353
<211> LENGTH: 25
<212> TYPE: RNA
<213> ORGANISM: artificial
<220> FEATURE:
<223> OTHER INFORMATION: oligonucleotide

<400> SEQUENCE: 353
ccagccauug uguugaaucc uuuaa                                              25

<210> SEQ ID NO 354
<211> LENGTH: 25
<212> TYPE: RNA
<213> ORGANISM: artificial
<220> FEATURE:
<223> OTHER INFORMATION: oligonucleotide

<400> SEQUENCE: 354
cagccauugu guugaauccu uuaac                                              25

<210> SEQ ID NO 355
<211> LENGTH: 25
<212> TYPE: RNA
<213> ORGANISM: artificial
<220> FEATURE:
<223> OTHER INFORMATION: oligonucleotide

<400> SEQUENCE: 355
agccauugug uugaauccuu uaaca                                              25
```

```
<210> SEQ ID NO 356
<211> LENGTH: 25
<212> TYPE: RNA
<213> ORGANISM: artificial
<220> FEATURE:
<223> OTHER INFORMATION: oligonucleotide

<400> SEQUENCE: 356
gccauugugu ugaauccuuu aacau                                          25

<210> SEQ ID NO 357
<211> LENGTH: 25
<212> TYPE: RNA
<213> ORGANISM: artificial
<220> FEATURE:
<223> OTHER INFORMATION: oligonucleotide

<400> SEQUENCE: 357
ccauuguguu gaauccuuua acauu                                          25

<210> SEQ ID NO 358
<211> LENGTH: 25
<212> TYPE: RNA
<213> ORGANISM: artificial
<220> FEATURE:
<223> OTHER INFORMATION: oligonucleotide

<400> SEQUENCE: 358
cauuguguug aauccuuuaa cauuu                                          25

<210> SEQ ID NO 359
<211> LENGTH: 20
<212> TYPE: RNA
<213> ORGANISM: artificial
<220> FEATURE:
<223> OTHER INFORMATION: oligonucleotide

<400> SEQUENCE: 359 cauuuugac cuacaugugg                                                 20

<210> SEQ ID NO 360
<211> LENGTH: 20
<212> TYPE: RNA
<213> ORGANISM: artificial
<220> FEATURE:
<223> OTHER INFORMATION: oligonucleotide

<400> SEQUENCE: 360
uuugaccuac auguggaaag                                                20

<210> SEQ ID NO 361
<211> LENGTH: 26
<212> TYPE: RNA
<213> ORGANISM: artificial
<220> FEATURE:
<223> OTHER INFORMATION: oligonucleotide

<400> SEQUENCE: 361
uacauuuuug accuacaugu ggaaag                                         26

<210> SEQ ID NO 362
<211> LENGTH: 17
<212> TYPE: RNA
<213> ORGANISM: artificial
<220> FEATURE:
```

<223> OTHER INFORMATION: oligonucleotide

<400> SEQUENCE: 362
ggucuccuua ccauga                                                    17

<210> SEQ ID NO 363
<211> LENGTH: 24
<212> TYPE: RNA
<213> ORGANISM: artificial
<220> FEATURE:
<223> OTHER INFORMATION: oligonucleotide

<400> SEQUENCE: 363
ucuuaccuau gacuauggau gaga                                           24

<210> SEQ ID NO 364
<211> LENGTH: 22
<212> TYPE: RNA
<213> ORGANISM: artificial
<220> FEATURE:
<223> OTHER INFORMATION: oligonucleotide

<400> SEQUENCE: 364
auuuuugacc uacaugggaa ag                                             22

<210> SEQ ID NO 365
<211> LENGTH: 23
<212> TYPE: RNA
<213> ORGANISM: artificial
<220> FEATURE:
<223> OTHER INFORMATION: oligonucleotide

<400> SEQUENCE: 365
uacgaguuga uugucggacc cag                                            23

<210> SEQ ID NO 366
<211> LENGTH: 25
<212> TYPE: RNA
<213> ORGANISM: artificial
<220> FEATURE:
<223> OTHER INFORMATION: oligonucleotide

<400> SEQUENCE: 366
guggucuccu uaccaugac ugugg                                           25

<210> SEQ ID NO 367
<211> LENGTH: 24
<212> TYPE: RNA
<213> ORGANISM: artificial
<220> FEATURE:
<223> OTHER INFORMATION: oligonucleotide

<400> SEQUENCE: 367
ugucucagua aucuucuuac cuau                                           24

<210> SEQ ID NO 368
<211> LENGTH: 23
<212> TYPE: RNA
<213> ORGANISM: artificial
<220> FEATURE:
<223> OTHER INFORMATION: oligonucleotide

<400> SEQUENCE: 368
ugcauguucc agucguugug ugg                                            23

```
<210> SEQ ID NO 369
<211> LENGTH: 25
<212> TYPE: RNA
<213> ORGANISM: artificial
<220> FEATURE:
<223> OTHER INFORMATION: oligonucleotide

<400> SEQUENCE: 369
cacuauucca gucaaauagg ucugg                                            25

<210> SEQ ID NO 370
<211> LENGTH: 25
<212> TYPE: RNA
<213> ORGANISM: artificial
<220> FEATURE:
<223> OTHER INFORMATION: oligonucleotide

<400> SEQUENCE: 370
auuuaccaac cuucaggauc gagua                                            25

<210> SEQ ID NO 371
<211> LENGTH: 21
<212> TYPE: RNA
<213> ORGANISM: artificial
<220> FEATURE:
<223> OTHER INFORMATION: oligonucleotide

<400> SEQUENCE: 371
ggccuaaaac acauacacau a                                                21

<210> SEQ ID NO 372
<211> LENGTH: 24
<212> TYPE: RNA
<213> ORGANISM: artificial
<220> FEATURE:
<223> OTHER INFORMATION: oligonucleotide

<400> SEQUENCE: 372
cccugaggca uucccaucuu gaau                                             24

<210> SEQ ID NO 373
<211> LENGTH: 20
<212> TYPE: RNA
<213> ORGANISM: artificial
<220> FEATURE:
<223> OTHER INFORMATION: oligonucleotide

<400> SEQUENCE: 373
aggacuuacu ugcuuuguuu                                                  20

<210> SEQ ID NO 374
<211> LENGTH: 23
<212> TYPE: RNA
<213> ORGANISM: artificial
<220> FEATURE:
<223> OTHER INFORMATION: oligonucleotide

<400> SEQUENCE: 374
cuugaauuua ggagauucau cug                                              23

<210> SEQ ID NO 375
<211> LENGTH: 23
<212> TYPE: RNA
<213> ORGANISM: artificial
<220> FEATURE:
<223> OTHER INFORMATION: oligonucleotide
```

```
<400> SEQUENCE: 375
caucuucuga uaauuuccu guu                                           23

<210> SEQ ID NO 376
<211> LENGTH: 20
<212> TYPE: RNA
<213> ORGANISM: artificial
<220> FEATURE:
<223> OTHER INFORMATION: oligonucleotide

<400> SEQUENCE: 376
ccauuacagu ugucuguguu                                              20

<210> SEQ ID NO 377
<211> LENGTH: 23
<212> TYPE: RNA
<213> ORGANISM: artificial
<220> FEATURE:
<223> OTHER INFORMATION: oligonucleotide

<400> SEQUENCE: 377
ugacagccug ugaaaucugu gag                                          23

<210> SEQ ID NO 378
<211> LENGTH: 20
<212> TYPE: RNA
<213> ORGANISM: artificial
<220> FEATURE:
<223> OTHER INFORMATION: oligonucleotide

<400> SEQUENCE: 378
uaaucugccu cuucuuuugg                                              20

<210> SEQ ID NO 379
<211> LENGTH: 20
<212> TYPE: RNA
<213> ORGANISM: artificial
<220> FEATURE:
<223> OTHER INFORMATION: oligonucleotide

<400> SEQUENCE: 379
cagcaguagu ugucaucugc                                              20

<210> SEQ ID NO 380
<211> LENGTH: 27
<212> TYPE: RNA
<213> ORGANISM: artificial
<220> FEATURE:
<223> OTHER INFORMATION: oligonucleotide

<400> SEQUENCE: 380
gccugagcug aucugcuggc aucuugc                                      27

<210> SEQ ID NO 381
<211> LENGTH: 31
<212> TYPE: RNA
<213> ORGANISM: artificial
<220> FEATURE:
<223> OTHER INFORMATION: oligonucleotide

<400> SEQUENCE: 381
gccugagcug aucugcuggc aucuugcagu u                                 31

<210> SEQ ID NO 382
<211> LENGTH: 16
```

```
<212> TYPE: RNA
<213> ORGANISM: artificial
<220> FEATURE:
<223> OTHER INFORMATION: oligonucleotide

<400> SEQUENCE: 382
ucugcuggca ucuugc                                                    16

<210> SEQ ID NO 383
<211> LENGTH: 22
<212> TYPE: RNA
<213> ORGANISM: artificial
<220> FEATURE:
<223> OTHER INFORMATION: oligonucleotide

<400> SEQUENCE: 383
gccgguugac uucauccugu gc                                             22

<210> SEQ ID NO 384
<211> LENGTH: 23
<212> TYPE: RNA
<213> ORGANISM: artificial
<220> FEATURE:
<223> OTHER INFORMATION: oligonucleotide

<400> SEQUENCE: 384
gucugcaucc aggaacaugg guc                                            23

<210> SEQ ID NO 385
<211> LENGTH: 24
<212> TYPE: RNA
<213> ORGANISM: artificial
<220> FEATURE:
<223> OTHER INFORMATION: oligonucleotide

<400> SEQUENCE: 385
uacuuacugu cuguagcucu uucu                                           24

<210> SEQ ID NO 386
<211> LENGTH: 22
<212> TYPE: RNA
<213> ORGANISM: artificial
<220> FEATURE:
<223> OTHER INFORMATION: oligonucleotide

<400> SEQUENCE: 386
cugcauccag gaacaugggu cc                                             22

<210> SEQ ID NO 387
<211> LENGTH: 24
<212> TYPE: RNA
<213> ORGANISM: artificial
<220> FEATURE:
<223> OTHER INFORMATION: oligonucleotide

<400> SEQUENCE: 387
guugaagauc ugauagccgg uuga                                           24

<210> SEQ ID NO 388
<211> LENGTH: 20
<212> TYPE: RNA
<213> ORGANISM: artificial
<220> FEATURE:
<223> OTHER INFORMATION: oligonucleotide

<400> SEQUENCE: 388
```
ucagcuucug uuagccacug                                                        20

<210> SEQ ID NO 389
<211> LENGTH: 20
<212> TYPE: RNA
<213> ORGANISM: artificial
<220> FEATURE:
<223> OTHER INFORMATION: oligonucleotide

<400> SEQUENCE: 389
uucagcuucu guuagccacu                                                        20

<210> SEQ ID NO 390
<211> LENGTH: 21
<212> TYPE: RNA
<213> ORGANISM: artificial
<220> FEATURE:
<223> OTHER INFORMATION: oligonucleotide

<400> SEQUENCE: 390
uucagcuucu guuagccacu g                                                      21

<210> SEQ ID NO 391
<211> LENGTH: 21
<212> TYPE: RNA
<213> ORGANISM: artificial
<220> FEATURE:
<223> OTHER INFORMATION: oligonucleotide

<400> SEQUENCE: 391
ucagcuucug uuagccacug a                                                      21

<210> SEQ ID NO 392
<211> LENGTH: 22
<212> TYPE: RNA
<213> ORGANISM: artificial
<220> FEATURE:
<223> OTHER INFORMATION: oligonucleotide

<400> SEQUENCE: 392
uucagcuucu guuagccacu ga                                                     22

<210> SEQ ID NO 393
<211> LENGTH: 21
<212> TYPE: RNA
<213> ORGANISM: artificial
<220> FEATURE:
<223> OTHER INFORMATION: oligonucleotide

<400> SEQUENCE: 393
ucagcuucug uuagccacug a                                                      21

<210> SEQ ID NO 394
<211> LENGTH: 22
<212> TYPE: RNA
<213> ORGANISM: artificial
<220> FEATURE:
<223> OTHER INFORMATION: oligonucleotide

<400> SEQUENCE: 394
uucagcuucu guuagccacu ga                                                     22

<210> SEQ ID NO 395
<211> LENGTH: 22
<212> TYPE: RNA
<213> ORGANISM: artificial

```
<220> FEATURE:
<223> OTHER INFORMATION: oligonucleotide

<400> SEQUENCE: 395
ucagcuucug uuagccacug au                                        22

<210> SEQ ID NO 396
<211> LENGTH: 23
<212> TYPE: RNA
<213> ORGANISM: artificial
<220> FEATURE:
<223> OTHER INFORMATION: oligonucleotide

<400> SEQUENCE: 396
uucagcuucu guuagccacu gau                                       23

<210> SEQ ID NO 397
<211> LENGTH: 23
<212> TYPE: RNA
<213> ORGANISM: artificial
<220> FEATURE:
<223> OTHER INFORMATION: oligonucleotide

<400> SEQUENCE: 397
ucagcuucug uuagccacug auu                                       23

<210> SEQ ID NO 398
<211> LENGTH: 24
<212> TYPE: RNA
<213> ORGANISM: artificial
<220> FEATURE:
<223> OTHER INFORMATION: oligonucleotide

<400> SEQUENCE: 398
uucagcuucu guuagccacu gauu                                      24

<210> SEQ ID NO 399
<211> LENGTH: 24
<212> TYPE: RNA
<213> ORGANISM: artificial
<220> FEATURE:
<223> OTHER INFORMATION: oligonucleotide

<400> SEQUENCE: 399
ucagcuucug uuagccacug auua                                      24

<210> SEQ ID NO 400
<211> LENGTH: 24
<212> TYPE: RNA
<213> ORGANISM: artificial
<220> FEATURE:
<223> OTHER INFORMATION: oligonucleotide

<400> SEQUENCE: 400
uucagcuucu guuagccacu gaua                                      24

<210> SEQ ID NO 401
<211> LENGTH: 25
<212> TYPE: RNA
<213> ORGANISM: artificial
<220> FEATURE:
<223> OTHER INFORMATION: oligonucleotide

<400> SEQUENCE: 401
ucagcuucug uuagccacug auuaa                                     25
```

```
<210> SEQ ID NO 402
<211> LENGTH: 26
<212> TYPE: RNA
<213> ORGANISM: artificial
<220> FEATURE:
<223> OTHER INFORMATION: oligonucleotide

<400> SEQUENCE: 402
uucagcuucu guuagccacu gauuaa                                              26

<210> SEQ ID NO 403
<211> LENGTH: 26
<212> TYPE: RNA
<213> ORGANISM: artificial
<220> FEATURE:
<223> OTHER INFORMATION: oligonucleotide

<400> SEQUENCE: 403
ucagcuucug uuagccacug auuaaa                                              26

<210> SEQ ID NO 404
<211> LENGTH: 27
<212> TYPE: RNA
<213> ORGANISM: artificial
<220> FEATURE:
<223> OTHER INFORMATION: oligonucleotide

<400> SEQUENCE: 404
uucagcuucu guuagccacu gauuaaa                                             27

<210> SEQ ID NO 405
<211> LENGTH: 19
<212> TYPE: RNA
<213> ORGANISM: artificial
<220> FEATURE:
<223> OTHER INFORMATION: oligonucleotide

<400> SEQUENCE: 405
cagcuucugu uagccacug                                                      19

<210> SEQ ID NO 406
<211> LENGTH: 21
<212> TYPE: RNA
<213> ORGANISM: artificial
<220> FEATURE:
<223> OTHER INFORMATION: oligonucleotide

<400> SEQUENCE: 406
cagcuucugu uagccacuga u                                                   21

<210> SEQ ID NO 407
<211> LENGTH: 21
<212> TYPE: RNA
<213> ORGANISM: artificial
<220> FEATURE:
<223> OTHER INFORMATION: oligonucleotide

<400> SEQUENCE: 407
agcuucuguu agccacugau u                                                   21

<210> SEQ ID NO 408
<211> LENGTH: 22
<212> TYPE: RNA
<213> ORGANISM: artificial
<220> FEATURE:
<223> OTHER INFORMATION: oligonucleotide
```

-continued

```
<400> SEQUENCE: 408
cagcuucugu uagccacuga uu                                              22

<210> SEQ ID NO 409
<211> LENGTH: 22
<212> TYPE: RNA
<213> ORGANISM: artificial
<220> FEATURE:
<223> OTHER INFORMATION: oligonucleotide

<400> SEQUENCE: 409
agcuucuguu agccacugau ua                                              22

<210> SEQ ID NO 410
<211> LENGTH: 23
<212> TYPE: RNA
<213> ORGANISM: artificial
<220> FEATURE:
<223> OTHER INFORMATION: oligonucleotide

<400> SEQUENCE: 410
cagcuucugu uagccacuga uua                                             23

<210> SEQ ID NO 411
<211> LENGTH: 23
<212> TYPE: RNA
<213> ORGANISM: artificial
<220> FEATURE:
<223> OTHER INFORMATION: oligonucleotide

<400> SEQUENCE: 411
agcuucuguu agccacugau uaa                                             23

<210> SEQ ID NO 412
<211> LENGTH: 24
<212> TYPE: RNA
<213> ORGANISM: artificial
<220> FEATURE:
<223> OTHER INFORMATION: oligonucleotide

<400> SEQUENCE: 412
cagcuucugu uagccacuga uuaa                                            24

<210> SEQ ID NO 413
<211> LENGTH: 24
<212> TYPE: RNA
<213> ORGANISM: artificial
<220> FEATURE:
<223> OTHER INFORMATION: oligonucleotide

<400> SEQUENCE: 413
agcuucuguu agccacugau uaaa                                            24

<210> SEQ ID NO 414
<211> LENGTH: 25
<212> TYPE: RNA
<213> ORGANISM: artificial
<220> FEATURE:
<223> OTHER INFORMATION: oligonucleotide

<400> SEQUENCE: 414
cagcuucugu uagccacuga uuaaa                                           25

<210> SEQ ID NO 415
```

```
<211> LENGTH: 24
<212> TYPE: RNA
<213> ORGANISM: artificial
<220> FEATURE:
<223> OTHER INFORMATION: oligonucleotide

<400> SEQUENCE: 415
agcuucuguu agccacugau uaaa                                             24

<210> SEQ ID NO 416
<211> LENGTH: 20
<212> TYPE: RNA
<213> ORGANISM: artificial
<220> FEATURE:
<223> OTHER INFORMATION: oligonucleotide

<400> SEQUENCE: 416
agcuucuguu agccacugau                                                  20

<210> SEQ ID NO 417
<211> LENGTH: 20
<212> TYPE: RNA
<213> ORGANISM: artificial
<220> FEATURE:
<223> OTHER INFORMATION: oligonucleotide

<400> SEQUENCE: 417 gcuucguua gccacugauu                                                   20

<210> SEQ ID NO 418
<211> LENGTH: 21
<212> TYPE: RNA
<213> ORGANISM: artificial
<220> FEATURE:
<223> OTHER INFORMATION: oligonucleotide

<400> SEQUENCE: 418
agcuucuguu agccacugau u                                                21

<210> SEQ ID NO 419
<211> LENGTH: 21
<212> TYPE: RNA
<213> ORGANISM: artificial
<220> FEATURE:
<223> OTHER INFORMATION: oligonucleotide

<400> SEQUENCE: 419
gcuucuguua gccacugauu a                                                21

<210> SEQ ID NO 420
<211> LENGTH: 22
<212> TYPE: RNA
<213> ORGANISM: artificial
<220> FEATURE:
<223> OTHER INFORMATION: oligonucleotide

<400> SEQUENCE: 420
agcuucuguu agccacugau ua                                               22

<210> SEQ ID NO 421
<211> LENGTH: 22
<212> TYPE: RNA
<213> ORGANISM: artificial
<220> FEATURE:
<223> OTHER INFORMATION: oligonucleotide

<400> SEQUENCE: 421
```

```
gcuucuguua gccacugauu aa                                                22

<210> SEQ ID NO 422
<211> LENGTH: 23
<212> TYPE: RNA
<213> ORGANISM: artificial
<220> FEATURE:
<223> OTHER INFORMATION: oligonucleotide

<400> SEQUENCE: 422
agcuucuguu agccacugau uaa                                               23

<210> SEQ ID NO 423
<211> LENGTH: 23
<212> TYPE: RNA
<213> ORGANISM: artificial
<220> FEATURE:
<223> OTHER INFORMATION: oligonucleotide

<400> SEQUENCE: 423
gcuucuguua gccacugauu aaa                                               23

<210> SEQ ID NO 424
<211> LENGTH: 24
<212> TYPE: RNA
<213> ORGANISM: artificial
<220> FEATURE:
<223> OTHER INFORMATION: oligonucleotide

<400> SEQUENCE: 424
agcuucuguu agccacugau uaaa                                              24

<210> SEQ ID NO 425
<211> LENGTH: 23
<212> TYPE: RNA
<213> ORGANISM: artificial
<220> FEATURE:
<223> OTHER INFORMATION: oligonucleotide

<400> SEQUENCE: 425
gcuucuguua gccacugauu aaa                                               23

<210> SEQ ID NO 426
<211> LENGTH: 23
<212> TYPE: RNA
<213> ORGANISM: artificial
<220> FEATURE:
<223> OTHER INFORMATION: oligonucleotide

<400> SEQUENCE: 426
ccauuuguau uuagcauguu ccc                                               23

<210> SEQ ID NO 427
<211> LENGTH: 20
<212> TYPE: RNA
<213> ORGANISM: artificial
<220> FEATURE:
<223> OTHER INFORMATION: oligoucleotide

<400> SEQUENCE: 427
agauaccauu uguauuuagc                                                   20

<210> SEQ ID NO 428
<211> LENGTH: 19
<212> TYPE: RNA
```

```
<213> ORGANISM: artificial
<220> FEATURE:
<223> OTHER INFORMATION: oligonucleotide

<400> SEQUENCE: 428
gccauuucuc aacagaucu                                                   19

<210> SEQ ID NO 429
<211> LENGTH: 23
<212> TYPE: RNA
<213> ORGANISM: artificial
<220> FEATURE:
<223> OTHER INFORMATION: oligonucleotide

<400> SEQUENCE: 429
gccauuucuc aacagaucug uca                                              23

<210> SEQ ID NO 430
<211> LENGTH: 23
<212> TYPE: RNA
<213> ORGANISM: artificial
<220> FEATURE:
<223> OTHER INFORMATION: oligonucleotide

<400> SEQUENCE: 430
auucucagga auugugucu uuc                                               23

<210> SEQ ID NO 431
<211> LENGTH: 21
<212> TYPE: RNA
<213> ORGANISM: artificial
<220> FEATURE:
<223> OTHER INFORMATION: oligonucleotide

<400> SEQUENCE: 431
ucucaggaau uugugucuuu c                                                21

<210> SEQ ID NO 432
<211> LENGTH: 18
<212> TYPE: RNA
<213> ORGANISM: artificial
<220> FEATURE:
<223> OTHER INFORMATION: oligonucleotide

<400> SEQUENCE: 432
guucagcuuc uguuagcc                                                    18

<210> SEQ ID NO 433
<211> LENGTH: 21
<212> TYPE: RNA
<213> ORGANISM: artificial
<220> FEATURE:
<223> OTHER INFORMATION: oligonucleotide

<400> SEQUENCE: 433
cugauuaaau aucuuuauau c                                                21

<210> SEQ ID NO 434
<211> LENGTH: 18
<212> TYPE: RNA
<213> ORGANISM: artificial
<220> FEATURE:
<223> OTHER INFORMATION: oligonucleotide

<400> SEQUENCE: 434
gccgccauuu cucaacag                                                    18
```

<210> SEQ ID NO 435
<211> LENGTH: 18
<212> TYPE: RNA
<213> ORGANISM: artificial
<220> FEATURE:
<223> OTHER INFORMATION: oligonucleotide

<400> SEQUENCE: 435
gccgccauuu cucaacag                                                 18

<210> SEQ ID NO 436
<211> LENGTH: 18
<212> TYPE: RNA
<213> ORGANISM: artificial
<220> FEATURE:
<223> OTHER INFORMATION: oligonucleotide

<400> SEQUENCE: 436
caggaauuug ugucuuuc                                                 18

<210> SEQ ID NO 437
<211> LENGTH: 25
<212> TYPE: RNA
<213> ORGANISM: artificial
<220> FEATURE:
<223> OTHER INFORMATION: oligonucleotide

<400> SEQUENCE: 437
uuugccgcug cccaaugcca uccug                                         25

<210> SEQ ID NO 438
<211> LENGTH: 25
<212> TYPE: RNA
<213> ORGANISM: artificial
<220> FEATURE:
<223> OTHER INFORMATION: oligonucleotide

<400> SEQUENCE: 438
auucaauguu cugacaacag uuugc                                         25

<210> SEQ ID NO 439
<211> LENGTH: 25
<212> TYPE: RNA
<213> ORGANISM: artificial
<220> FEATURE:
<223> OTHER INFORMATION: oligonucleotide

<400> SEQUENCE: 439
ccaguugcau ucaauguucu gacaa                                         25

<210> SEQ ID NO 440
<211> LENGTH: 22
<212> TYPE: RNA
<213> ORGANISM: artificial
<220> FEATURE:
<223> OTHER INFORMATION: oligonucleotide

<400> SEQUENCE: 440
caguugcauu caauguucug ac                                            22

<210> SEQ ID NO 441
<211> LENGTH: 20
<212> TYPE: RNA
<213> ORGANISM: artificial
<220> FEATURE:

<223> OTHER INFORMATION: oligonucleotide

<400> SEQUENCE: 441
aguugcauuc aauguucuga                                               20

<210> SEQ ID NO 442
<211> LENGTH: 21
<212> TYPE: RNA
<213> ORGANISM: artificial
<220> FEATURE:
<223> OTHER INFORMATION: oligonucleotide

<400> SEQUENCE: 442
gauugcugaa uuauuucuuc c                                             21

<210> SEQ ID NO 443
<211> LENGTH: 25
<212> TYPE: RNA
<213> ORGANISM: artificial
<220> FEATURE:
<223> OTHER INFORMATION: oligonucleotide

<400> SEQUENCE: 443
gauugcugaa uuauuucuuc cccag                                         25

<210> SEQ ID NO 444
<211> LENGTH: 25
<212> TYPE: RNA
<213> ORGANISM: artificial
<220> FEATURE:
<223> OTHER INFORMATION: oligonucleotide

<400> SEQUENCE: 444
auugcugaau uauuucuucc ccagu                                         25

<210> SEQ ID NO 445
<211> LENGTH: 25
<212> TYPE: RNA
<213> ORGANISM: artificial
<220> FEATURE:
<223> OTHER INFORMATION: oligonucleotide

<400> SEQUENCE: 445
uugcugaauu auuucuuccc caguu                                         25

<210> SEQ ID NO 446
<211> LENGTH: 25
<212> TYPE: RNA
<213> ORGANISM: artificial
<220> FEATURE:
<223> OTHER INFORMATION: oligonucleotide

<400> SEQUENCE: 446
ugcugaauua uuucuucccc aguug                                         25

<210> SEQ ID NO 447
<211> LENGTH: 25
<212> TYPE: RNA
<213> ORGANISM: artificial
<220> FEATURE:
<223> OTHER INFORMATION: oligonucleotide

<400> SEQUENCE: 447
gcugaauuau uucuucccca guugc                                         25

```
<210> SEQ ID NO 448
<211> LENGTH: 25
<212> TYPE: RNA
<213> ORGANISM: artificial
<220> FEATURE:
<223> OTHER INFORMATION: oligonucleotide

<400> SEQUENCE: 448
cugaauuauu ucuucccccag uugca                                              25

<210> SEQ ID NO 449
<211> LENGTH: 25
<212> TYPE: RNA
<213> ORGANISM: artificial
<220> FEATURE:
<223> OTHER INFORMATION: oligonucleotide

<400> SEQUENCE: 449
ugaauuauuu cuucccccagu ugcau                                              25

<210> SEQ ID NO 450
<211> LENGTH: 25
<212> TYPE: RNA
<213> ORGANISM: artificial
<220> FEATURE:
<223> OTHER INFORMATION: oligonucleotide

<400> SEQUENCE: 450
gaauuauuuc uucccccaguu gcauu                                              25

<210> SEQ ID NO 451
<211> LENGTH: 25
<212> TYPE: RNA
<213> ORGANISM: artificial
<220> FEATURE:
<223> OTHER INFORMATION: oligonucleotide

<400> SEQUENCE: 451
aauuauuucu ucccccaguug cauuc                                              25

<210> SEQ ID NO 452
<211> LENGTH: 25
<212> TYPE: RNA
<213> ORGANISM: artificial
<220> FEATURE:
<223> OTHER INFORMATION: oligonucleotide

<400> SEQUENCE: 452
auuauuucuu ccccaguugc auuca                                               25

<210> SEQ ID NO 453
<211> LENGTH: 25
<212> TYPE: RNA
<213> ORGANISM: artificial
<220> FEATURE:
<223> OTHER INFORMATION: oligonucleotide

<400> SEQUENCE: 453
uuauuucuuc cccaguugca uucaa                                               25

<210> SEQ ID NO 454
<211> LENGTH: 25
<212> TYPE: RNA
<213> ORGANISM: artificial
<220> FEATURE:
<223> OTHER INFORMATION: oligonucleotide
```

<400> SEQUENCE: 454
uauuucuucc ccaguugcau ucaau            25

<210> SEQ ID NO 455
<211> LENGTH: 25
<212> TYPE: RNA
<213> ORGANISM: artificial
<220> FEATURE:
<223> OTHER INFORMATION: oligonucleotide

<400> SEQUENCE: 455
auuucuuccc caguugcauu caaug            25

<210> SEQ ID NO 456
<211> LENGTH: 25
<212> TYPE: RNA
<213> ORGANISM: artificial
<220> FEATURE:
<223> OTHER INFORMATION: oligonucleotide

<400> SEQUENCE: 456
uuucuucccc aguugcauuc aaugu            25

<210> SEQ ID NO 457
<211> LENGTH: 25
<212> TYPE: RNA
<213> ORGANISM: artificial
<220> FEATURE:
<223> OTHER INFORMATION: oligonucleotide

<400> SEQUENCE: 457
uucuucccca guugcauuca auguu            25

<210> SEQ ID NO 458
<211> LENGTH: 25
<212> TYPE: RNA
<213> ORGANISM: artificial
<220> FEATURE:
<223> OTHER INFORMATION: oligonucleotide

<400> SEQUENCE: 458
ucuuccccag uugcauucaa uguuc            25

<210> SEQ ID NO 459
<211> LENGTH: 25
<212> TYPE: RNA
<213> ORGANISM: artificial
<220> FEATURE:
<223> OTHER INFORMATION: oligonucleotide

<400> SEQUENCE: 459
cuuccccagu ugcauucaau guucu            25

<210> SEQ ID NO 460
<211> LENGTH: 25
<212> TYPE: RNA
<213> ORGANISM: artificial
<220> FEATURE:
<223> OTHER INFORMATION: oligonucleotide

<400> SEQUENCE: 460
uuccccaguu gcauucaaug uucug            25

<210> SEQ ID NO 461
<211> LENGTH: 25

```
<212> TYPE: RNA
<213> ORGANISM: artificial
<220> FEATURE:
<223> OTHER INFORMATION: oligonucleotide

<400> SEQUENCE: 461
uccccaguug cauucaaugu ucuga                                              25

<210> SEQ ID NO 462
<211> LENGTH: 25
<212> TYPE: RNA
<213> ORGANISM: artificial
<220> FEATURE:
<223> OTHER INFORMATION: oligonucleotide

<400> SEQUENCE: 462
ccccaguugc auucaauguu cugac                                              25

<210> SEQ ID NO 463
<211> LENGTH: 25
<212> TYPE: RNA
<213> ORGANISM: artificial
<220> FEATURE:
<223> OTHER INFORMATION: oligonucleotide

<400> SEQUENCE: 463
cccaguugca uucaauguuc ugaca                                              25

<210> SEQ ID NO 464
<211> LENGTH: 25
<212> TYPE: RNA
<213> ORGANISM: artificial
<220> FEATURE:
<223> OTHER INFORMATION: oligonucleotide

<400> SEQUENCE: 464
ccaguugcau ucaauguucu gacaa                                              25

<210> SEQ ID NO 465
<211> LENGTH: 25
<212> TYPE: RNA
<213> ORGANISM: artificial
<220> FEATURE:
<223> OTHER INFORMATION: oligonucleotide

<400> SEQUENCE: 465
caguugcauu caauguucug acaac                                              25

<210> SEQ ID NO 466
<211> LENGTH: 25
<212> TYPE: RNA
<213> ORGANISM: artificial
<220> FEATURE:
<223> OTHER INFORMATION: oligonucleotide

<400> SEQUENCE: 466
aguugcauuc aauguucuga caaca                                              25

<210> SEQ ID NO 467
<211> LENGTH: 20
<212> TYPE: RNA
<213> ORGANISM: artificial
<220> FEATURE:
<223> OTHER INFORMATION: oligonucleotide

<400> SEQUENCE: 467
```
uccuguagaa uacuggcauc 20

<210> SEQ ID NO 468
<211> LENGTH: 27
<212> TYPE: RNA
<213> ORGANISM: artificial
<220> FEATURE:
<223> OTHER INFORMATION: oligonucleotide

<400> SEQUENCE: 468
ugcagaccuc cugccaccgc agauuca 27

<210> SEQ ID NO 469
<211> LENGTH: 34
<212> TYPE: RNA
<213> ORGANISM: artificial
<220> FEATURE:
<223> OTHER INFORMATION: oligonucleotide

<400> SEQUENCE: 469
uugcagaccu ccugccaccg cagauucagg cuuc 34

<210> SEQ ID NO 470
<211> LENGTH: 25
<212> TYPE: RNA
<213> ORGANISM: artificial
<220> FEATURE:
<223> OTHER INFORMATION: oligonucleotide

<400> SEQUENCE: 470
guugcauuca auguucugac aacag 25

<210> SEQ ID NO 471
<211> LENGTH: 25
<212> TYPE: RNA
<213> ORGANISM: artificial
<220> FEATURE:
<223> OTHER INFORMATION: oligonucleotide

<400> SEQUENCE: 471
uugcauucaa uguucugaca acagu 25

<210> SEQ ID NO 472
<211> LENGTH: 25
<212> TYPE: RNA
<213> ORGANISM: artificial
<220> FEATURE:
<223> OTHER INFORMATION: oligonucleotide

<400> SEQUENCE: 472
ugcauucaau guucugacaa caguu 25

<210> SEQ ID NO 473
<211> LENGTH: 25
<212> TYPE: RNA
<213> ORGANISM: artificial
<220> FEATURE:
<223> OTHER INFORMATION: oligonucleotide

<400> SEQUENCE: 473
gcauucaaug uucugacaac aguuu 25

<210> SEQ ID NO 474
<211> LENGTH: 25
<212> TYPE: RNA
<213> ORGANISM: artificial

```
<220> FEATURE:
<223> OTHER INFORMATION: oligonucleotide

<400> SEQUENCE: 474
cauucaaugu ucugacaaca guuug                                            25

<210> SEQ ID NO 475
<211> LENGTH: 25
<212> TYPE: RNA
<213> ORGANISM: artificial
<220> FEATURE:
<223> OTHER INFORMATION: oligonucleotide

<400> SEQUENCE: 475
auucaauguu cugacaacag uuugc                                            25

<210> SEQ ID NO 476
<211> LENGTH: 25
<212> TYPE: RNA
<213> ORGANISM: artificial
<220> FEATURE:
<223> OTHER INFORMATION: oligonucleotide

<400> SEQUENCE: 476
ucaauguucu gacaacaguu ugccg                                            25

<210> SEQ ID NO 477
<211> LENGTH: 25
<212> TYPE: RNA
<213> ORGANISM: artificial
<220> FEATURE:
<223> OTHER INFORMATION: oligonucleotide

<400> SEQUENCE: 477
caauguucug acaacaguuu gccgc                                            25

<210> SEQ ID NO 478
<211> LENGTH: 25
<212> TYPE: RNA
<213> ORGANISM: artificial
<220> FEATURE:
<223> OTHER INFORMATION: oligonucleotide

<400> SEQUENCE: 478
aauguucuga caacaguuug ccgcu                                            25

<210> SEQ ID NO 479
<211> LENGTH: 25
<212> TYPE: RNA
<213> ORGANISM: artificial
<220> FEATURE:
<223> OTHER INFORMATION: oligonucleotide

<400> SEQUENCE: 479
auguucugac aacaguuugc cgcug                                            25

<210> SEQ ID NO 480
<211> LENGTH: 25
<212> TYPE: RNA
<213> ORGANISM: artificial
<220> FEATURE:
<223> OTHER INFORMATION: oligonucleotide

<400> SEQUENCE: 480
uguucugaca acaguuugcc gcugc                                            25
```

<210> SEQ ID NO 481
<211> LENGTH: 25
<212> TYPE: RNA
<213> ORGANISM: artificial
<220> FEATURE:
<223> OTHER INFORMATION: oligonucleotide

<400> SEQUENCE: 481
guucugacaa caguuugccg cugcc                                              25

<210> SEQ ID NO 482
<211> LENGTH: 25
<212> TYPE: RNA
<213> ORGANISM: artificial
<220> FEATURE:
<223> OTHER INFORMATION: oligonucleotide

<400> SEQUENCE: 482
uucugacaac aguuugccgc ugccc                                              25

<210> SEQ ID NO 483
<211> LENGTH: 25
<212> TYPE: RNA
<213> ORGANISM: artificial
<220> FEATURE:
<223> OTHER INFORMATION: oligonucleotide

<400> SEQUENCE: 483
ucugacaaca guuugccgcu gccca                                              25

<210> SEQ ID NO 484
<211> LENGTH: 25
<212> TYPE: RNA
<213> ORGANISM: artificial
<220> FEATURE:
<223> OTHER INFORMATION: oligonucleotide

<400> SEQUENCE: 484
cugacaacag uuugccgcug cccaa                                              25

<210> SEQ ID NO 485
<211> LENGTH: 25
<212> TYPE: RNA
<213> ORGANISM: artificial
<220> FEATURE:
<223> OTHER INFORMATION: oligonucleotide

<400> SEQUENCE: 485
ugacaacagu uugccgcugc ccaau                                              25

<210> SEQ ID NO 486
<211> LENGTH: 25
<212> TYPE: RNA
<213> ORGANISM: artificial
<220> FEATURE:
<223> OTHER INFORMATION: oligonucleotide

<400> SEQUENCE: 486
gacaacaguu ugccgcugcc caaug                                              25

<210> SEQ ID NO 487
<211> LENGTH: 25
<212> TYPE: RNA
<213> ORGANISM: artificial
<220> FEATURE:
<223> OTHER INFORMATION: oligonucleotide

```
<400> SEQUENCE: 487
acaacaguuu gccgcugccc aaugc                                        25

<210> SEQ ID NO 488
<211> LENGTH: 25
<212> TYPE: RNA
<213> ORGANISM: artificial
<220> FEATURE:
<223> OTHER INFORMATION: oligonculeotide

<400> SEQUENCE: 488
caacaguuug ccgcugccca augcc                                        25

<210> SEQ ID NO 489
<211> LENGTH: 25
<212> TYPE: RNA
<213> ORGANISM: artificial
<220> FEATURE:
<223> OTHER INFORMATION: oligonucleotide

<400> SEQUENCE: 489
aacaguuugc cgcugcccaa ugcca                                        25

<210> SEQ ID NO 490
<211> LENGTH: 25
<212> TYPE: RNA
<213> ORGANISM: artificial
<220> FEATURE:
<223> OTHER INFORMATION: oligonucleotide

<400> SEQUENCE: 490
acaguuugcc gcugcccaau gccau                                        25

<210> SEQ ID NO 491
<211> LENGTH: 25
<212> TYPE: RNA
<213> ORGANISM: artificial
<220> FEATURE:
<223> OTHER INFORMATION: oligonucleotide

<400> SEQUENCE: 491
caguuugccg cugcccaaug ccauc                                        25

<210> SEQ ID NO 492
<211> LENGTH: 25
<212> TYPE: RNA
<213> ORGANISM: artificial
<220> FEATURE:
<223> OTHER INFORMATION: oligonucleotide

<400> SEQUENCE: 492
aguuugccgc ugcccaaugc caucc                                        25

<210> SEQ ID NO 493
<211> LENGTH: 25
<212> TYPE: RNA
<213> ORGANISM: artificial
<220> FEATURE:
<223> OTHER INFORMATION: oligonucleotide

<400> SEQUENCE: 493
guuugccgcu gcccaaugcc auccu                                        25

<210> SEQ ID NO 494
```

```
<211> LENGTH: 25
<212> TYPE: RNA
<213> ORGANISM: artificial
<220> FEATURE:
<223> OTHER INFORMATION: oligonucleotide

<400> SEQUENCE: 494
uuugccgcug cccaaugcca uccug                                           25

<210> SEQ ID NO 495
<211> LENGTH: 25
<212> TYPE: RNA
<213> ORGANISM: artificial
<220> FEATURE:
<223> OTHER INFORMATION: oligonucleotide

<400> SEQUENCE: 495
uugccgcugc ccaaugccau ccugg                                           25

<210> SEQ ID NO 496
<211> LENGTH: 25
<212> TYPE: RNA
<213> ORGANISM: artificial
<220> FEATURE:
<223> OTHER INFORMATION: oligonucleotide

<400> SEQUENCE: 496
ugccgcugcc caaugccauc cugga                                           25

<210> SEQ ID NO 497
<211> LENGTH: 25
<212> TYPE: RNA
<213> ORGANISM: artificial
<220> FEATURE:
<223> OTHER INFORMATION: oligonucleotide

<400> SEQUENCE: 497
gccgcugccc aaugccaucc uggag                                           25

<210> SEQ ID NO 498
<211> LENGTH: 25
<212> TYPE: RNA
<213> ORGANISM: artificial
<220> FEATURE:
<223> OTHER INFORMATION: oligonucleotide

<400> SEQUENCE: 498
ccgcugccca augccauccu ggagu                                           25

<210> SEQ ID NO 499
<211> LENGTH: 25
<212> TYPE: RNA
<213> ORGANISM: artificial
<220> FEATURE:
<223> OTHER INFORMATION: oligonucleotide

<400> SEQUENCE: 499
cgcugcccaa ugccauccug gaguu                                           25

<210> SEQ ID NO 500
<211> LENGTH: 20
<212> TYPE: RNA
<213> ORGANISM: artificial
<220> FEATURE:
<223> OTHER INFORMATION: oligonucleotide

<400> SEQUENCE: 500
```

```
uguuuuugag gauugcugaa                                         20

<210> SEQ ID NO 501
<211> LENGTH: 40
<212> TYPE: RNA
<213> ORGANISM: artificial
<220> FEATURE:
<223> OTHER INFORMATION: oligonucleotide

<400> SEQUENCE: 501
uguucugaca acaguuugcc gcugcccaau gccauccugg                   40

<210> SEQ ID NO 502
<211> LENGTH: 20
<212> TYPE: RNA
<213> ORGANISM: artificial
<220> FEATURE:
<223> OTHER INFORMATION: oligonucleotide

<400> SEQUENCE: 502
cuguugcagu aaucuaugag                                         20

<210> SEQ ID NO 503
<211> LENGTH: 20
<212> TYPE: RNA
<213> ORGANISM: artificial
<220> FEATURE:
<223> OTHER INFORMATION: oligonucleotide

<400> SEQUENCE: 503
ugcaguaauc uaugaguuuc                                         20

<210> SEQ ID NO 504
<211> LENGTH: 18
<212> TYPE: RNA
<213> ORGANISM: artificial
<220> FEATURE:
<223> OTHER INFORMATION: oligonucleotide

<400> SEQUENCE: 504
gagucuucua ggagccuu                                           18

<210> SEQ ID NO 505
<211> LENGTH: 23
<212> TYPE: RNA
<213> ORGANISM: artificial
<220> FEATURE:
<223> OTHER INFORMATION: oligonucleotide

<400> SEQUENCE: 505
ugccauuguu ucaucagcuc uuu                                     23

<210> SEQ ID NO 506
<211> LENGTH: 20
<212> TYPE: RNA
<213> ORGANISM: artificial
<220> FEATURE:
<223> OTHER INFORMATION: oligonucleotide

<400> SEQUENCE: 506
uccuguagga cauuggcagu                                         20

<210> SEQ ID NO 507
<211> LENGTH: 20
<212> TYPE: RNA
```

<213> ORGANISM: artificial
<220> FEATURE:
<223> OTHER INFORMATION: oligonucleotide

<400> SEQUENCE: 507
cuuggagucu ucuaggagcc                                                20

<210> SEQ ID NO 508
<211> LENGTH: 17
<212> TYPE: RNA
<213> ORGANISM: artificial
<220> FEATURE:
<223> OTHER INFORMATION: oligonucleotide

<400> SEQUENCE: 508
uaggugccug ccggcuu                                                   17

<210> SEQ ID NO 509
<211> LENGTH: 18
<212> TYPE: RNA
<213> ORGANISM: artificial
<220> FEATURE:
<223> OTHER INFORMATION: oligonucleotide

<400> SEQUENCE: 509
uucagcugua gccacacc                                                  18

<210> SEQ ID NO 510
<211> LENGTH: 21
<212> TYPE: RNA
<213> ORGANISM: artificial
<220> FEATURE:
<223> OTHER INFORMATION: oligonucleotide

<400> SEQUENCE: 510
cugaacugcu ggaaagucgc c                                              21

<210> SEQ ID NO 511
<211> LENGTH: 30
<212> TYPE: RNA
<213> ORGANISM: artificial
<220> FEATURE:
<223> OTHER INFORMATION: oligonucleotide

<400> SEQUENCE: 511
cuggcuucca aaugggaccu gaaaaagaac                                     30

<210> SEQ ID NO 512
<211> LENGTH: 21
<212> TYPE: RNA
<213> ORGANISM: artificial
<220> FEATURE:
<223> OTHER INFORMATION: oligonucleotide

<400> SEQUENCE: 512
caauuuuucc cacucaguau u                                              21

<210> SEQ ID NO 513
<211> LENGTH: 19
<212> TYPE: RNA
<213> ORGANISM: artificial
<220> FEATURE:
<223> OTHER INFORMATION: oligonucleotide

<400> SEQUENCE: 513
uugaaguucc uggagucuu                                                 19

<210> SEQ ID NO 514
<211> LENGTH: 22
<212> TYPE: RNA
<213> ORGANISM: artificial
<220> FEATURE:
<223> OTHER INFORMATION: oligonucleotide

<400> SEQUENCE: 514
uccucaggag gcagcucuaa au                                        22

<210> SEQ ID NO 515
<211> LENGTH: 16
<212> TYPE: RNA
<213> ORGANISM: artificial
<220> FEATURE:
<223> OTHER INFORMATION: oligonucleotide

<400> SEQUENCE: 515
uggcucucuc ccaggg                                               16

<210> SEQ ID NO 516
<211> LENGTH: 27
<212> TYPE: RNA
<213> ORGANISM: artificial
<220> FEATURE:
<223> OTHER INFORMATION: oligonucleotide

<400> SEQUENCE: 516
gagauggcuc ucucccaggg acccugg                                   27

<210> SEQ ID NO 517
<211> LENGTH: 17
<212> TYPE: RNA
<213> ORGANISM: artificial
<220> FEATURE:
<223> OTHER INFORMATION: oligonucleotide

<400> SEQUENCE: 517
gggcacuuug uuuggcg                                              17

<210> SEQ ID NO 518
<211> LENGTH: 19
<212> TYPE: RNA
<213> ORGANISM: artificial
<220> FEATURE:
<223> OTHER INFORMATION: oligonucleotide

<400> SEQUENCE: 518
ggucccagca aguuguuug                                            19

<210> SEQ ID NO 519
<211> LENGTH: 25
<212> TYPE: RNA
<213> ORGANISM: artificial
<220> FEATURE:
<223> OTHER INFORMATION: oligonucleotide

<400> SEQUENCE: 519
ugggaugguc ccagcaaguu guuug                                     25

<210> SEQ ID NO 520
<211> LENGTH: 21
<212> TYPE: RNA
<213> ORGANISM: artificial
<220> FEATURE:

<223> OTHER INFORMATION: oligonucleotide

<400> SEQUENCE: 520
guagagcucu gucauuugg g                                              21

<210> SEQ ID NO 521
<211> LENGTH: 25
<212> TYPE: RNA
<213> ORGANISM: artificial
<220> FEATURE:
<223> OTHER INFORMATION: oligonucleotide

<400> SEQUENCE: 521
gcucaagaga uccacugcaa aaaac                                         25

<210> SEQ ID NO 522
<211> LENGTH: 26
<212> TYPE: RNA
<213> ORGANISM: artificial
<220> FEATURE:
<223> OTHER INFORMATION: oligonucleotide

<400> SEQUENCE: 522
gccauacgua cguaucauaa acauuc                                        26

<210> SEQ ID NO 523
<211> LENGTH: 25
<212> TYPE: RNA
<213> ORGANISM: artificial
<220> FEATURE:
<223> OTHER INFORMATION: oligonucleotide

<400> SEQUENCE: 523
ucugcaggau auccaugggc ugguc                                         25

<210> SEQ ID NO 524
<211> LENGTH: 27
<212> TYPE: RNA
<213> ORGANISM: artificial
<220> FEATURE:
<223> OTHER INFORMATION: oligonucleotide

<400> SEQUENCE: 524
gauccucccu guucgucccc uauuaug                                       27

<210> SEQ ID NO 525
<211> LENGTH: 24
<212> TYPE: RNA
<213> ORGANISM: artificial
<220> FEATURE:
<223> OTHER INFORMATION: oligonucleotide

<400> SEQUENCE: 525
ugcuuuagac uccuguaccu gaua                                          24

<210> SEQ ID NO 526
<211> LENGTH: 18
<212> TYPE: RNA
<213> ORGANISM: artificial
<220> FEATURE:
<223> OTHER INFORMATION: oligonucleotide

<400> SEQUENCE: 526
ggcggccuuu guguugac                                                 18

```
<210> SEQ ID NO 527
<211> LENGTH: 25
<212> TYPE: RNA
<213> ORGANISM: artificial
<220> FEATURE:
<223> OTHER INFORMATION: oligonucleotide

<400> SEQUENCE: 527
ggacaggccu uuauguucgu gcugc                                              25

<210> SEQ ID NO 528
<211> LENGTH: 19
<212> TYPE: RNA
<213> ORGANISM: artificial
<220> FEATURE:
<223> OTHER INFORMATION: oligonucleotide

<400> SEQUENCE: 528
ccuuuauguu cgugcugcu                                                     19

<210> SEQ ID NO 529
<211> LENGTH: 25
<212> TYPE: RNA
<213> ORGANISM: artificial
<220> FEATURE:
<223> OTHER INFORMATION: oligonucleotide

<400> SEQUENCE: 529
ccucagcucu ugaaguaaac gguuu                                              25

<210> SEQ ID NO 530
<211> LENGTH: 25
<212> TYPE: RNA
<213> ORGANISM: artificial
<220> FEATURE:
<223> OTHER INFORMATION: oligonucleotide

<400> SEQUENCE: 530
cucagcucuu gaaguaaacg guuua                                              25

<210> SEQ ID NO 531
<211> LENGTH: 25
<212> TYPE: RNA
<213> ORGANISM: artificial
<220> FEATURE:
<223> OTHER INFORMATION: oligonucleotide

<400> SEQUENCE: 531
ucagcucuug aaguaaacgg uuuac                                              25

<210> SEQ ID NO 532
<211> LENGTH: 25
<212> TYPE: RNA
<213> ORGANISM: artificial
<220> FEATURE:
<223> OTHER INFORMATION: oligonucleotide

<400> SEQUENCE: 532
cagcucuuga aguaaacggu uuacc                                              25

<210> SEQ ID NO 533
<211> LENGTH: 25
<212> TYPE: RNA
<213> ORGANISM: artificial
<220> FEATURE:
<223> OTHER INFORMATION: oligonucleotide
```

```
<400> SEQUENCE: 533
agcucuugaa guaaacgguu uaccg                                  25

<210> SEQ ID NO 534
<211> LENGTH: 25
<212> TYPE: RNA
<213> ORGANISM: artificial
<220> FEATURE:
<223> OTHER INFORMATION: oligonucleotide

<400> SEQUENCE: 534
gcucuugaag uaaacgguuu accgc                                  25

<210> SEQ ID NO 535
<211> LENGTH: 25
<212> TYPE: RNA
<213> ORGANISM: artificial
<220> FEATURE:
<223> OTHER INFORMATION: oligonucleotide

<400> SEQUENCE: 535
cucuugaagu aaacgguuua ccgcc                                  25
```

METHODS AND MEANS FOR EFFICIENT SKIPPING OF AT LEAST ONE OF THE EXONS 51-53, 55, 57 AND 59 OF THE HUMAN DUCHENNE MUSCULAR DYSTROPHY GENE

This application is a continuation of U.S. application Ser. No. 13/094,571 filed Apr. 26, 2011, which is a continuation of International Application No. PCT/NL2009/050113, filed on Mar. 11, 2009, which claims priority to PCT/NL2008/050673, filed on Oct. 27, 2008, the contents of each of which are herein incorporated by reference in their entirety. The invention relates to the field of genetics, more specifically human genetics. The invention in particular relates to modulation of splicing of the human Duchenne Muscular Dystrophy pre-mRNA.

FIELD

The invention relates to the field of genetics, more specifically human genetics. The invention in particular relates to modulation of splicing of the human Duchenne Muscular Dystrophy pre-mRNA.

BACKGROUND OF THE INVENTION

Myopathies are disorders that result in functional impairment of muscles. Muscular dystrophy (MD) refers to genetic diseases that are characterized by progressive weakness and degeneration of skeletal muscles. Duchenne muscular dystrophy (DMD) and Becker muscular dystrophy (BMD) are the most common childhood forms of muscular dystrophy. They are recessive disorders and because the gene responsible for DMD and BMD resides on the X-chromosome, mutations mainly affect males with an incidence of about 1 in 3500 boys.

DMD and BMD are caused by genetic defects in the DMD gene encoding dystrophin, a muscle protein that is required for interactions between the cytoskeleton and the extracellular matrix to maintain muscle fiber stability during contraction. DMD is a severe, lethal neuromuscular disorder resulting in a dependency on wheelchair support before the age of 12 and DMD patients often die before the age of thirty due to respiratory- or heart failure. In contrast, BMD patients often remain ambulatory until later in life, and have near normal life expectancies. DMD mutations in the DMD gene are characterized by frame shifting insertions or deletions or nonsense point mutations, resulting in the absence of functional dystrophin. BMD mutations in general keep the reading frame intact, allowing synthesis of a partly functional dystrophin.

During the last decade, specific modification of splicing in order to restore the disrupted reading frame of the dystrophin transcript has emerged as a promising therapy for Duchenne muscular dystrophy (DMD) (van Ommen, van Deutekom, Aartsma-Rus, Curr Opin Mol Ther. 2008; 10(2): 140-9, Yokota, Duddy, Partidge, Acta Myol. 2007; 26(3): 179-84, van Deutekom et al., N Engl J Med. 2007; 357(26): 2677-86).

Using antisense oligonucleotides (AONs) interfering with splicing signals the skipping of specific exons can be induced in the DMD pre-mRNA, thus restoring the open reading frame and converting the severe DMD into a milder BMD phenotype (van Deutekom et al. Hum Mol Genet. 2001; 10: 1547-54; Aartsma-Rus et al., Hum Mol Genet 2003; 12(8):907-14). In vivo proof-of-concept was first obtained in the mdx mouse model, which is dystrophin-deficient due to a nonsense mutation in exon 23. Intramuscular and intravenous injections of AONs targeting the mutated exon 23 restored dystrophin expression for at least three months (Lu et al. Nat Med. 2003; 8: 1009-14; Lu et al., Proc Natl Acad Sci USA. 2005; 102(1):198-203). This was accompanied by restoration of dystrophin-associated proteins at the fiber membrane as well as functional improvement of the treated muscle. In vivo skipping of human exons has also been achieved in the hDMD mouse model, which contains a complete copy of the human DMD gene integrated in chromosome 5 of the mouse (Bremmer-Bout et al. Molecular Therapy. 2004; 10: 232-40; 't Hoen et al. J Biol Chem. 2008; 283: 5899-907).

Recently, a first-in-man study was successfully completed where an AON inducing the skipping of exon 51 was injected into a small area of the tibialis anterior muscle of four DMD patients. Novel dystrophin expression was observed in the majority of muscle fibers in all four patients treated, and the AON was safe and well tolerated (van Deutekom et al. N Engl J Med. 2007; 357: 2677-86).

DESCRIPTION OF THE INVENTION

Method

In a first aspect, the present invention provides a method for inducing, and/or promoting skipping of at least one of exons 43, 46, 50-53 of the DMD pre-mRNA in a patient, preferably in an isolated cell of a patient, the method comprising providing said cell and/or said patient with a molecule that binds to a continuous stretch of at least 8 nucleotides within said exon. It is to be understood that said method encompasses an in vitro, in vivo or ex vivo method.

Accordingly, a method is provided for inducing and/or promoting skipping of at least one of exons 43, 46, 50-53 of DMD pre-mRNA in a patient, preferably in an isolated cell of said patient, the method comprising providing said cell and/or said patient with a molecule that binds to a continuous stretch of at least 8 nucleotides within said exon.

As defined herein a DMD pre-mRNA preferably means the pre-mRNA of a DMD gene of a DMD or BMD patient.

A patient is preferably intended to mean a patient having DMD or BMD as later defined herein or a patient susceptible to develop DMD or BMD due to his or her genetic background. In the case of a DMD patient, an oligonucleotide used will preferably correct one mutation as present in the DMD gene of said patient and therefore will preferably create a DMD protein that will look like a BMD protein: said protein will preferably be a functional dystrophin as later defined herein. In the case of a BMD patient, an oligonucleotide as used will preferably correct one mutation as present in the BMD gene of said patient and therefore will preferably create a dystrophin which will be more functional than the dystrophin which was originally present in said BMD patient.

Exon skipping refers to the induction in a cell of a mature mRNA that does not contain a particular exon that is normally present therein. Exon skipping is performed by providing a cell expressing the pre-mRNA of said mRNA with a molecule capable of interfering with essential sequences such as for example the splice donor of splice acceptor sequence that required for splicing of said exon, or a molecule that is capable of interfering with an exon inclusion signal that is required for recognition of a stretch of nucleotides as an exon to be included in the mRNA. The term pre-mRNA refers to a non-processed or partly processed precursor mRNA that is synthesized from a DNA template in the cell nucleus by transcription.

Within the context of the invention, inducing and/or promoting skipping of an exon as indicated herein means that at least 1%, 10%, 20%, 30%, 40%, 50%, 60%, 70%, 80%, 90% or more of the DMD mRNA in one or more (muscle) cells of a treated patient will not contain said exon. This is preferably assessed by PCR as described in the examples.

Preferably, a method of the invention by inducing and/or promoting skipping of at least one of the following exons 43, 46, 50-53 of the DMD pre-mRNA in one or more (muscle) cells of a patient, provides said patient with a functional dystrophin protein and/or decreases the production of an aberrant dystrophin protein in said patient and/or increases the production of a functional dystrophin is said patient.

Providing a patient with a functional dystrophin protein and/or decreasing the production of an aberrant dystrophin protein in said patient is typically applied in a DMD patient. Increasing the production of a functional dystrophin is typically applied in a BMD patient.

Therefore a preferred method is a method, wherein a patient or one or more cells of said patient is provided with a functional dystrophin protein and/or wherein the production of an aberrant dystrophin protein in said patient is decreased and/or wherein the production of a functional dystrophin is increased in said patient, wherein the level of said aberrant or functional dystrophin is assessed by comparison to the level of said dystrophin in said patient at the onset of the method.

Decreasing the production of an aberrant dystrophin may be assessed at the mRNA level and preferably means that 99%, 90%, 80%, 70%, 60%, 50%, 40%, 30%, 20%, 10%, 5% or less of the initial amount of aberrant dystrophin mRNA, is still detectable by RT PCR. An aberrant dystrophin mRNA or protein is also referred to herein as a non-functional dystrophin mRNA or protein. A non functional dystrophin protein is preferably a dystrophin protein which is not able to bind actin and/or members of the DGC protein complex. A non-functional dystrophin protein or dystrophin mRNA does typically not have, or does not encode a dystrophin protein with an intact C-terminus of the protein.

Increasing the production of a functional dystrophin in said patient or in a cell of said patient may be assessed at the mRNA level (by RT-PCR analysis) and preferably means that a detectable amount of a functional dystrophin mRNA is detectable by RT PCR. In another embodiment, 1%, 5%, 10%, 20%, 30%, 40%, 50%, 60%, 70%, 80%, 90% or more of the detectable dystrophin mRNA is a functional dystrophin mRNA. Increasing the production of a functional dystrophin in said patient or in a cell of said patient may be assessed at the protein level (by immunofluorescence and western blot analyses) and preferably means that a detectable amount of a functional dystrophin protein is detectable by immunofluorescence or western blot analysis. In another embodiment, 1%, 5%, 10%, 20%, 30%, 40%, 50%, 60%, 70%, 80%, 90% or more of the detectable dystrophin protein is a functional dystrophin protein.

As defined herein, a functional dystrophin is preferably a wild type dystrophin corresponding to a protein having the amino acid sequence as identified in SEQ ID NO: 1. A functional dystrophin is preferably a dystrophin, which has an actin binding domain in its N terminal part (first 240 amino acids at the N terminus), a cystein-rich domain (amino acid 3361 till 3685) and a C terminal domain (last 325 amino acids at the C terminus) each of these domains being present in a wild type dystrophin as known to the skilled person. The amino acids indicated herein correspond to amino acids of the wild type dystrophin being represented by SEQ ID NO:1. In other words, a functional dystrophin is a dystrophin which exhibits at least to some extent an activity of a wild type dystrophin "At least to some extent" preferably means at least 10%, 20%, 30%, 40%, 50%, 60%, 70%, 80%, 90%, 95% or 100% of a corresponding activity of a wild type functional dystrophin. In this context, an activity of a functional dystrophin is preferably binding to actin and to the dystrophin-associated glycoprotein complex (DGC) (Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144). Binding of dystrophin to actin and to the DGC complex may be visualized by either co-immunoprecipitation using total protein extracts or immunofluorescence analysis of cross-sections, from a muscle biopsy, as known to the skilled person.

Individuals or patients suffering from Duchenne muscular dystrophy typically have a mutation in the gene encoding dystrophin that prevent synthesis of the complete protein, i.e of a premature stop prevents the synthesis of the C-terminus. In Becker muscular dystrophy the DMD gene also comprises a mutation compared tot the wild type gene but the mutation does typically not induce a premature stop and the C-terminus is typically synthesized. As a result a functional dystrophin protein is synthesized that has at least the same activity in kind as the wild type protein, not although not necessarily the same amount of activity. The genome of a BMD individual typically encodes a dystrophin protein comprising the N terminal part (first 240 amino acids at the N terminus), a cystein-rich domain (amino acid 3361 till 3685) and a C terminal domain (last 325 amino acids at the C terminus) but its central rod shaped domain may be shorter than the one of a wild type dystrophin (Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144). Exon skipping for the treatment of DMD is typically directed to overcome a premature stop in the pre-mRNA by skipping an exon in the rod-shaped domain to correct the reading frame and allow synthesis of remainder of the dystrophin protein including the C-terminus, albeit that the protein is somewhat smaller as a result of a smaller rod domain. In a preferred embodiment, an individual having DMD and being treated by a method as defined herein will be provided a dystrophin which exhibits at least to some extent an activity of a wild type dystrophin More preferably, if said individual is a Duchenne patient or is suspected to be a Duchenne patient, a functional dystrophin is a dystrophin of an individual having BMD: typically said dystrophin is able to interact with both actin and the DGC, but its central rod shaped domain may be shorter than the one of a wild type dystrophin (Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144). The central rod-shaped domain of wild type dystrophin comprises 24 spectrin-like repeats (Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144). For example, a central rod-shaped domain of a dystrophin as provided herein may comprise 5 to 23, 10 to 22 or 12 to 18 spectrin-like repeats as long as it can bind to actin and to DGC.

A method of the invention may alleviate one or more characteristics of a myogenic or muscle cell of a patient or alleviate one or more symptoms of a DMD patient having a deletion including but not limited to exons 44, 44-46, 44-47, 44-48, 44-49, 44-51, 44-53 (correctable by exon 43 skipping), 19-45, 21-45, 43-45, 45, 47-54, 47-56 (correctable by exon 46 skipping), 51, 51-53, 51-55, 51-57 (correctable by exon 50 skipping), 13-50, 19-50, 29-50, 43-50, 45-50, 47-50, 48-50, 49-50, 50, 52 (correctable by exon 51 skipping), exons 8-51, 51, 53, 53-55, 53-57, 53-59, 53-60, (correctable by exon 52 skipping) and exons 10-52, 42-52, 43-52, 45-52, 47-52, 48-52, 49-52, 50-52, 52 (correctable by exon 53 skipping) in the DMD gene, occurring in a total of 68% of all DMD patients with a deletion (Aartsma-Rus et al., Hum. Mut. 2009).

Alternatively, a method of the invention may improve one or more characteristics of a muscle cell of a patient or alleviate one or more symptoms of a DMD patient having small mutations in, or single exon duplications of exon 43, 46, 50-53 in the DMD gene, occurring in a total of 36% of all DMD patients with a deletion (Aartsma-Rus et al, Hum. Mut. 2009)

Furthermore, for some patients the simultaneous skipping of one of more exons in addition to exon 43, exon 46 and/or exon 50-53 is required to restore the open reading frame, including patients with specific deletions, small (point) mutations, or double or multiple exon duplications, such as (but not limited to) a deletion of exons 44-50 requiring the co-skipping of exons 43 and 51, with a deletion of exons 46-50 requiring the co-skipping of exons 45 and 51, with a deletion of exons 44-52 requiring the co-skipping of exons 43 and 53, with a deletion of exons 46-52 requiring the co-skipping of exons 45 and 53, with a deletion of exons 51-54 requiring the co-skipping of exons 50 and 55, with a deletion of exons 53-54 requiring the co-skipping of exons 52 and 55, with a deletion of exons 53-56 requiring the co-skipping of exons 52 and 57, with a nonsense mutation in exon 43 or exon 44 requiring the co-skipping of exon 43 and 44, with a nonsense mutation in exon 45 or exon 46 requiring the co-skipping of exon 45 and 46, with a nonsense mutation in exon 50 or exon 51 requiring the co-skipping of exon 50 and 51, with a nonsense mutation in exon 51 or exon 52 requiring the co-skipping of exon 51 and 52, with a nonsense mutation in exon 52 or exon 53 requiring the co-skipping of exon 52 and 53, or with a double or multiple exon duplication involving exons 43, 46, 50, 51, 52, and/or 53.

In a preferred method, the skipping of exon 43 is induced, or the skipping of exon 46 is induced, or the skipping of exon 50 is induced or the skipping of exon 51 is induced or the skipping of exon 52 is induced or the skipping of exon 53 is induced. An induction of the skipping of two of these exons is also encompassed by a method of the invention. For example, preferably skipping of exons 50 and 51, or 52 and 53, or 43 and 51, or 43 and 53, or 51 and 52. Depending on the type and the identity (the specific exons involved) of mutation identified in a patient, the skilled person will know which combination of exons needs to be skipped in said patient.

In a preferred method, one or more symptom(s) of a DMD or a BMD patient is/are alleviated and/or one or more characteristic(s) of one or more muscle cells from a DMD or a BMD patient is/are improved. Such symptoms or characteristics may be assessed at the cellular, tissue level or on the patient self.

An alleviation of one or more characteristics may be assessed by any of the following assays on a myogenic cell or muscle cell from a patient: reduced calcium uptake by muscle cells, decreased collagen synthesis, altered morphology, altered lipid biosynthesis, decreased oxidative stress, and/or improved muscle fiber function, integrity, and/or survival. These parameters are usually assessed using immunofluorescence and/or histochemical analyses of cross sections of muscle biopsies.

The improvement of muscle fiber function, integrity and/or survival may be assessed using at least one of the following assays: a detectable decrease of creatine kinase in blood, a detectable decrease of necrosis of muscle fibers in a biopsy cross-section of a muscle suspected to be dystrophic, and/or a detectable increase of the homogeneity of the diameter of muscle fibers in a biopsy cross-section of a muscle suspected to be dystrophic. Each of these assays is known to the skilled person.

Creatine kinase may be detected in blood as described in Hodgetts et al (Hodgetts S., et al, (2006), Neuromuscular Disorders, 16: 591-602.2006). A detectable decrease in creatine kinase may mean a decrease of 5%, 10%, 20%, 30%, 40%, 50%, 60%, 70%, 80%, 90% or more compared to the concentration of creatine kinase in a same DMD or BMD patient before treatment.

A detectable decrease of necrosis of muscle fibers is preferably assessed in a muscle biopsy, more preferably as described in Hodgetts et al (Hodgetts S., et al, (2006), Neuromuscular Disorders, 16: 591-602.2006) using biopsy cross-sections. A detectable decrease of necrosis may be a decrease of 5%, 10%, 20%, 30%, 40%, 50%, 60%, 70%, 80%, 90% or more of the area wherein necrosis has been identified using biopsy cross-sections. The decrease is measured by comparison to the necrosis as assessed in a same DMD or BMD patient before treatment.

A detectable increase of the homogeneity of the diameter of a muscle fiber is preferably assessed in a muscle biopsy cross-section, more preferably as described in Hodgetts et al (Hodgetts S., et al, (2006), Neuromuscular Disorders, 16: 591-602.2006). The increase is measured by comparison to the homogeneity of the diameter of a muscle fiber in a same DMD or BMD patient before treatment An alleviation of one or more symptoms may be assessed by any of the following assays on the patient self: prolongation of time to loss of walking, improvement of muscle strength, improvement of the ability to lift weight, improvement of the time taken to rise from the floor, improvement in the nine-meter walking time, improvement in the time taken for four-stairs climbing, improvement of the leg function grade, improvement of the pulmonary function, improvement of cardiac function, improvement of the quality of life. Each of these assays is known to the skilled person. As an example, the publication of Manzur at al (Manzur A Y et al, (2008), Glucocorticoid corticosteroids for Duchenne muscular dystrophy (review), Wiley publishers, The Cochrane collaboration.) gives an extensive explanation of each of these assays. For each of these assays, as soon as a detectable improvement or prolongation of a parameter measured in an assay has been found, it will preferably mean that one or more symptoms of Duchenne Muscular Dystrophy or Becker Muscular Dystrophy has been alleviated in an individual using a method of the invention. Detectable improvement or prolongation is preferably a statistically significant improvement or prolongation as described in Hodgetts et al (Hodgetts S., et al, (2006), Neuromuscular Disorders, 16: 591-602.2006). Alternatively, the alleviation of one or more symptom(s) of Duchenne Muscular Dystrophy or Becker Muscular Dystrophy may be assessed by measuring an improvement of a muscle fiber function, integrity and/or survival as later defined herein.

A treatment in a method according to the invention may have a duration of at least one week, at least one month, at least several months, at least one year, at least 2, 3, 4, 5, 6 years or more.

Each molecule or oligonucleotide or equivalent thereof as defined herein for use according to the invention may be suitable for direct administration to a cell, tissue and/or an organ in vivo of individuals affected by or at risk of developing DMD or BMD, and may be administered directly in vivo, ex vivo or in vitro. The frequency of administration of a molecule or an oligonucleotide or a composition of the invention may depend on several parameters such as the age of the patient, the mutation of the patient, the number of molecules (dose), the formulation of said molecule. The frequency may be ranged between at least once in a two weeks, or three weeks or four weeks or five weeks or a longer time period.

A molecule or oligonucleotide or equivalent thereof can be delivered as is to a cell. When administering said molecule, oligonucleotide or equivalent thereof to an individual, it is preferred that it is dissolved in a solution that is compatible with the delivery method. For intravenous, subcutaneous, intramuscular, intrathecal and/or intraventricular administration it is preferred that the solution is a physiological salt solution. Particularly preferred for a method of the invention is the use of an excipient that will further enhance delivery of said molecule, oligonucleotide or functional equivalent thereof as defined herein, to a cell and into a cell, preferably a muscle cell. Preferred excipient are defined in the section entitled "pharmaceutical composition".

In a preferred method of the invention, an additional molecule is used which is able to induce and/or promote skipping of another exon of the DMD pre-mRNA of a patient. Preferably, the second exon is selected from: exon 6, 7, 11, 17, 19, 21, 43, 44, 45, 50, 51, 52, 53, 55, 57, 59, 62, 63, 65, 66, 69, or 75 of the DMD pre-mRNA of a patient. Molecules which can be used are depicted in any one of Table 1 to 7. This way, inclusion of two or more exons of a DMD pre-mRNA in mRNA produced from this pre-mRNA is prevented. This embodiment is further referred to as double- or multi-exon skipping (Aartsma-Rus A, Janson A A, Kaman W E, et al. Antisense-induced multiexon skipping for Duchenne muscular dystrophy makes more sense. Am J Hum Genet 2004; 74(1):83-92, Aartsma-Rus A, Kaman W E, Weij R, den Dunnen J T, van Ommen G J, van Deutekom J C. Exploring the frontiers of therapeutic exon skipping for Duchenne muscular dystrophy by double targeting within one or multiple exons. Mol Ther 2006; 14(3):401-7). In most cases double-exon skipping results in the exclusion of only the two targeted exons from the DMD pre-mRNA. However, in other cases it was found that the targeted exons and the entire region in between said exons in said pre-mRNA were not present in the produced mRNA even when other exons (intervening exons) were present in such region. This multi-skipping was notably so for the combination of oligonucleotides derived from the DMD gene, wherein one oligonucleotide for exon 45 and one oligonucleotide for exon 51 was added to a cell transcribing the DMD gene. Such a set-up resulted in mRNA being produced that did not contain exons 45 to 51. Apparently, the structure of the pre-mRNA in the presence of the mentioned oligonucleotides was such that the splicing machinery was stimulated to connect exons 44 and 52 to each other.

It is possible to specifically promote the skipping of also the intervening exons by providing a linkage between the two complementary oligonucleotides. Hence, in one embodiment stretches of nucleotides complementary to at least two dystrophin exons are separated by a linking moiety. The at least two stretches of nucleotides are thus linked in this embodiment so as to form a single molecule.

In case, more than one compounds or molecules are used in a method of the invention, said compounds can be administered to an individual in any order. In one embodiment, said compounds are administered simultaneously (meaning that said compounds are administered within 10 hours, preferably within one hour). This is however not necessary. In another embodiment, said compounds are administered sequentially.

Molecule

In a second aspect, there is provided a molecule for use in a method as described in the previous section entitled "Method". A molecule as defined herein is preferably an oligonucleotide or antisense oligonucleotide (AON).

It was found by the present investigators that any of exon 43, 46, 50-53 is specifically skipped at a high frequency using a molecule that preferably binds to a continuous stretch of at least 8 nucleotides within said exon. Although this effect can be associated with a higher binding affinity of said molecule, compared to a molecule that binds to a continuous stretch of less than 8 nucleotides, there could be other intracellular parameters involved that favor thermodynamic, kinetic, or structural characteristics of the hybrid duplex. In a preferred embodiment, a molecule that binds to a continuous stretch of at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides within said exon is used.

In a preferred embodiment, a molecule or an oligonucleotide of the invention which comprises a sequence that is complementary to a part of any of exon 43, 46, 50-53 of DMD pre-mRNA is such that the complementary part is at least 50% of the length of the oligonucleotide of the invention, more preferably at least 60%, even more preferably at least 70%, even more preferably at least 80%, even more preferably at least 90% or even more preferably at least 95%, or even more preferably 98% and most preferably up to 100%. "A part of said exon" preferably means a stretch of at least 8 nucleotides. In a most preferred embodiment, an oligonucleotide of the invention consists of a sequence that is complementary to part of said exon DMD pre-mRNA as defined herein. For example, an oligonucleotide may comprise a sequence that is complementary to part of said exon DMD pre-mRNA as defined herein and additional flanking sequences. In a more preferred embodiment, the length of said complementary part of said oligonucleotide is of at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides. Preferably, additional flanking sequences are used to modify the binding of a protein to said molecule or oligonucleotide, or to modify a thermodynamic property of the oligonucleotide, more preferably to modify target RNA binding affinity.

A preferred molecule to be used in a method of the invention binds or is complementary to a continuous stretch of at least 8 nucleotides within one of the following nucleotide sequences selected from:
5'-AGAUAGUCUACAACAAAGCUCAGGUCG-GAUUGACAUUAUUCAU AGCAAGAAGACAGCAG-CAUUGCAAAGUGAACGCCUGUGG-3' (SEQ ID NO: 2) for skipping of exon 43;

5'-UUAUGGUUGGAGGAAGCAGAUAACAUUGCUAGUAUCCCACUUG AACCUGGAAAAGAGCAGCAACUAAAAGAAAAGC-3' (SEQ ID NO: 3) for skipping of exon 46;
5'-GGCGGTAAACCGUUUACUUCAAGAGCUGAGGGCAAAGCAGCCUG ACCUAGCUCCUGGACUGACCACUAUUGG-3' (SEQ ID NO: 4) for skipping of exon 50;
5'-CUCCUACUCAGACUGUUACUCUGGUGACACAACCUGUGGUUACU AAGGAAACUGCCAUCUCCAAACUAGAAAUGCCAUCUUCCUUGAUG UUGGAGGUAC-3' (SEQ ID NO: 5) for skipping of exon 51;
5'-AUGCAGGAUUUGGAACAGAGGCGUCCCCAGUUGGAAGAACUCAU UACCGCUGCCCAAAAUUUGAAAAACAAGACCAGCAAUCAAGAGGCU-3' (SEQ ID NO:6) for skipping of exon 52, and
5'-AAAUGUUAAAGGAUUCAACACAAUGGCUGGAAGCUAAGGAAGAA GCUGAGCAGGUCUUAGGACAGGCCAGAG-3' (SEQ ID NO:7) for skipping of exon 53.

Of the numerous molecules that theoretically can be prepared to bind to the continuous nucleotide stretches as defined by SEQ ID NO 2-7 within one of said exons, the invention provides distinct molecules that can be used in a method for efficiently skipping of at least one of exon 43, exon 46 and/or exon 50-53. Although the skipping effect can be addressed to the relatively high density of putative SR protein binding sites within said stretches, there could be other parameters involved that favor uptake of the molecule or other, intracellular parameters such as thermodynamic, kinetic, or structural characteristics of the hybrid duplex.

It was found that a molecule that binds to a continuous stretch comprised within or consisting of any of SEQ ID NO 2-7 results in highly efficient skipping of exon 43, exon 46 and/or exon 50-53 respectively in a cell and/or in a patient provided with this molecule. Therefore, in a preferred embodiment, a method is provided wherein a molecule binds to a continuous stretch of at least 8, 10, 12, 15, 18, 20, 25, 30, 35, 40, 45, 50 nucleotides within SEQ ID NO 2-7.

In a preferred embodiment for inducing and/or promoting the skipping of any of exon 43, exon 46 and/or exon 50-53, the invention provides a molecule comprising or consisting of an antisense nucleotide sequence selected from the antisense nucleotide sequences depicted in any of Tables 1 to 6. A molecule of the invention preferably comprises or consist of the antisense nucleotide sequence of SEQ ID NO 16, SEQ ID NO 65, SEQ ID NO 70, SEQ ID NO 91, SEQ ID NO 110, SEQ ID NO 117, SEQ ID NO 127, SEQ ID NO 165, SEQ ID NO 166, SEQ ID NO 167, SEQ ID NO 246, SEQ ID NO 299, SEQ ID NO:357.

A preferred molecule of the invention comprises a nucleotide-based or nucleotide or an antisense oligonucleotide sequence of between 8 and 50 nucleotides or bases, more preferred between 10 and 50 nucleotides, more preferred between 20 and 40 nucleotides, more preferred between 20 and 30 nucleotides, such as 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, 31 nucleotides, 32 nucleotides, 33 nucleotides, 34 nucleotides, 35 nucleotides, 36 nucleotides, 37 nucleotides, 38 nucleotides, 39 nucleotides, 40 nucleotides, 41 nucleotides, 42 nucleotides, 43 nucleotides, 44 nucleotides, 45 nucleotides, 46 nucleotides, 47 nucleotides, 48 nucleotides, 49 nucleotides or 50 nucleotides. A most preferred molecule of the invention comprises a nucleotide-based sequence of 25 nucleotides.

Furthermore, none of the indicated sequences is derived from conserved parts of splice-junction sites. Therefore, said molecule is not likely to mediate differential splicing of other exons from the DMD pre-mRNA or exons from other genes.

In one embodiment, a molecule of the invention is a compound molecule that binds to the specified sequence, or a protein such as an RNA-binding protein or a non-natural zinc-finger protein that has been modified to be able to bind to the corresponding nucleotide sequence on a DMD pre-RNA molecule. Methods for screening compound molecules that bind specific nucleotide sequences are, for example, disclosed in PCT/NL01/00697 and U.S. Pat. No. 6,875,736, which are herein incorporated by reference. Methods for designing RNA-binding Zinc-finger proteins that bind specific nucleotide sequences are disclosed by Friesen and Darby, Nature Structural Biology 5: 543-546 (1998) which is herein incorporated by reference.

A preferred molecule of the invention binds to at least part of the sequence of SEQ ID NO 2: 5'-AGAUAGUCUACAACAAAGCUCAGGUCGGAUUGACAUUAUUCAU AGCAAGAAGACAGCAGCAUUGCAAAGUGCAACGCCUGUGG-3' which is present in exon 43 of the DMD gene. More preferably, the invention provides a molecule comprising or consisting of the antisense nucleotide sequence of SEQ ID NO 8 to SEQ ID NO 69.

In an even more preferred embodiment, the invention provides a molecule comprising or consisting of the antisense nucleotide sequence of SEQ ID NO 16 and/or SEQ ID NO 65.

In a most preferred embodiment, the invention provides a molecule comprising or consisting of the antisense nucleotide sequence of SEQ ID NO 65. It was found that this molecule is very efficient in modulating splicing of exon 43 of the DMD pre-mRNA in a muscle cell and/or in a patient.

Another preferred molecule of the invention binds to at least part of the sequence of SEQ ID NO 3: 5'-UUAUGGUUGGAGGAAGCAGAUAACAUUGCUAGUAUCCCACUUG AACCUGGAAAAGAGCAGCAACUAAAAGAAAAGC-3' which is present in exon 46 of the DMD gene. More preferably, the invention provides a molecule comprising or consisting of the antisense nucleotide sequence of SEQ ID NO 70 to SEQ ID NO 122. In an even more preferred embodiment, the invention provides a molecule comprising or consisting of the antisense nucleotide sequence of SEQ ID NO 70, SEQ ID NO 91, SEQ ID NO 110, and/or SEQ ID N0117.

In a most preferred embodiment, the invention provides a molecule comprising or consisting of the antisense nucleotide sequence of SEQ ID NO 117. It was found that this molecule is very efficient in modulating splicing of exon 46 of the DMD pre-mRNA in a muscle cell or in a patient.

Another preferred molecule of the invention binds to at least part of the sequence of SEQ ID NO 4: 5'-GGCGGTAAACCGUUUACUUCAAGAGCU GAGGGCAAAGCAGCCUGACCUAGCUCCUGGACUGACCACUAUUGG-3' which is present in exon 50 of the DMD gene. More preferably, the invention provides a molecule comprising or consisting of the antisense nucleotide sequence of SEQ ID NO 123 to SEQ ID NO 167 and/or SEQ ID NO 529 to SEQ ID NO 535.

In an even more preferred embodiment, the invention provides a molecule comprising or consisting of the antisense nucleotide sequence of SEQ ID NO 127, or SEQ ID NO 165, or SEQ ID NO 166 and/or SEQ ID NO 167.

In a most preferred embodiment, the invention provides a molecule comprising or consisting of the antisense nucleotide sequence of SEQ ID NO 127. It was found that this molecule is very efficient in modulating splicing of exon 50 of the DMD pre-mRNA in a muscle cell and/or in a patient.

Another preferred molecule of the invention binds to at least part of the sequence of SEQ ID NO 5: 5'-CUCCUA-CUCAGACUGUUACUCUGGUGACACAACCUGUG-GUUACU AAGGAAACUGCCAUCUCCAAACUA-GAAAUGCCAUCUUCCUUGAUG UUGGGAGGUAC-3' which is present in exon 51 of the DMD gene. More preferably, the invention provides a molecule comprising or consisting of the antisense nucleotide sequence of SEQ ID NO 168 to SEQ ID NO 241.

Another preferred molecule of the invention binds to at least part of the sequence of SEQ ID NO 6: 5'-AUG-CAGGAUUUGGAACAGAGGCGUCCCCAGUUGGAA-GAACUCAUUACCGCUGCCCAAAAUUUGAAAAAC-AAGACCAGCAAUCAAGAGGCU-3' which is present in exon 52 of the DMD gene. More preferably, the invention provides a molecule comprising or consisting of the antisense nucleotide sequence of SEQ ID NO 242 to SEQ ID NO 310. In an even more preferred embodiment, the invention provides a molecule comprising or consisting of the antisense nucleotide sequence of SEQ ID NO 246 and/or SEQ ID NO 299. In a most preferred embodiment, the invention provides a molecule comprising or consisting of the antisense nucleotide sequence of SEQ ID NO 299. It was found that this molecule is very efficient in modulating splicing of exon 52 of the DMD pre-mRNA in a muscle cell and/or in a patient.

Another preferred molecule of the invention binds to at least part of the sequence of SEQ ID NO 7: 5'-AAAU-GUUAAAGGAUUCAACACAAUGGCUGGAAGC-UAAGGAAGAAGCUGAGCAGGUCUUAGGACAGGC-CAGAG-3' which is present in exon 53 of the DMD gene. More preferably, the invention provides a molecule comprising or consisting of the antisense nucleotide sequence of SEQ ID NO 311 to SEQ ID NO 358.

In a most preferred embodiment, the invention provides a molecule comprising or consisting of the antisense nucleotide sequence of SEQ ID NO 357. It was found that this molecule is very efficient in modulating splicing of exon 53 of the DMD pre-mRNA in a muscle cell and/or in a patient.

A nucleotide sequence of a molecule of the invention may contain RNA residues, or one or more DNA residues, and/or one or more nucleotide analogues or equivalents, as will be further detailed herein below.

It is preferred that a molecule of the invention comprises one or more residues that are modified to increase nuclease resistance, and/or to increase the affinity of the antisense nucleotide for the target sequence. Therefore, in a preferred embodiment, the antisense nucleotide sequence comprises at least one nucleotide analogue or equivalent, wherein a nucleotide analogue or equivalent is defined as a residue having a modified base, and/or a modified backbone, and/or a non-natural internucleoside linkage, or a combination of these modifications.

In a preferred embodiment, the nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery; however, because the morpholino backbone is uncharged, cationic lipids are not effective mediators of morpholino oligonucleotide uptake in cells. A recent report demonstrated triplex formation by a morpholino oligonucleotide and, because of the non-ionic backbone, these studies showed that the morpholino oligonucleotide was capable of triplex formation in the absence of magnesium.

It is further preferred that that the linkage between the residues in a backbone do not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent comprises a Peptide Nucleic Acid (PNA), having a modified polyamide backbone (Nielsen, et al. (1991) Science 254, 1497-1500). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar (2005) Chem. Commun, 495-497). Since the backbone of a PNA molecule contains no charged phosphate groups, PNA-RNA hybrids are usually more stable than RNA-RNA or RNA-DNA hybrids, respectively (Egholm et al (1993) Nature 365, 566-568).

A further preferred backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, a nucleotide analogue or equivalent of the invention comprises a substitution of one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent of the invention comprises one or more sugar moieties that are mono- or disubstituted at the 2', 3' and/or 5' position such as a —OH; —F; substituted or unsubstituted, linear or branched lower (C1-C10) alkyl, alkenyl, alkynyl, alkaryl, allyl, aryl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; -aminoxy; methoxyethoxy; -dimethylaminooxyethoxy; and -dimethylaminoethoxyethoxy. The sugar moiety can be a pyranose or derivative thereof, or a deoxypyranose or derivative thereof, preferably a ribose or a derivative thereof, or a deoxyribose or a derivative thereof. Such preferred derivatized sugar moieties comprise Locked Nucleic Acid (LNA), in which the 2'-carbon atom is linked to the 3' or 4' carbon atom of the sugar ring thereby forming a bicyclic sugar moiety. A preferred LNA comprises 2'-O, 4'-C-ethylene-bridged nucleic acid (Morita et al. 2001. Nucleic Acid Res Supplement No. 1: 241-242). These substitutions render the nucleotide analogue or equivalent RNase H and nuclease resistant and increase the affinity for the target RNA.

It is understood by a skilled person that it is not necessary for all positions in an antisense oligonucleotide to be modified uniformly. In addition, more than one of the aforementioned analogues or equivalents may be incorporated in a single antisense oligonucleotide or even at a single position within an antisense oligonucleotide. In certain embodiments, an antisense oligonucleotide of the invention has at least two different types of analogues or equivalents.

A preferred antisense oligonucleotide according to the invention comprises a 2'-O alkyl phosphorothioate antisense oligonucleotide, such as 2'-O-methyl modified ribose (RNA), 2'-O-ethyl modified ribose, 2'-O-propyl modified ribose, and/or substituted derivatives of these modifications such as halogenated derivatives.

A most preferred antisense oligonucleotide according to the invention comprises of 2'-O-methyl phosphorothioate ribose.

A functional equivalent of a molecule of the invention may be defined as an oligonucleotide as defined herein wherein an activity of said functional equivalent is retained to at least some extent. Preferably, an activity of said functional equivalent is inducing exon 43, 46, 50, 51, 52, or 53 skipping and providing a functional dystrophin protein. Said activity of said functional equivalent is therefore preferably assessed by detection of exon 43, 46, 50, 51, 52, or 53 skipping and by quantifying the amount of functional dystrophin protein. A functional dystrophin is herein preferably defined as being a dystrophin able to bind actin and members of the DGC protein complex. The assessment of said activity of an oligonucleotide is preferably done by RT-PCR or by immunofluorescence or Western blot analyses. Said activity is preferably retained to at least some extent when it represents at least 50%, or at least 60%, or at least 70% or at least 80% or at least 90% or at least 95% or more of corresponding activity of said oligonucleotide the functional equivalent derives from. Throughout this application, when the word oligonucleotide is used it may be replaced by a functional equivalent thereof as defined herein.

It will be understood by a skilled person that distinct antisense oligonucleotides can be combined for efficiently skipping any of exon 43, exon 46, exon 50, exon 51, exon 52 and/or exon 53 of the human DMD pre-mRNA. It is encompassed by the present invention to use one, two, three, four, five or more oligonucleotides for skipping one of said exons (i.e. exon, 43, 46, 50, 51, 52, or 53). It is also encompassed to use at least two oligonucleotides for skipping at least two, of said exons. Preferably two of said exons are skipped. More preferably, these two exons are:
43 and 51, or
43 and 53, or
50 and 51, or
51 and 52, or
52 and 53.

The skilled person will know which combination of exons is preferred to be skipped depending on the type, the number and the location of the mutation present in a DMD or BMD patient.

An antisense oligonucleotide can be linked to a moiety that enhances uptake of the antisense oligonucleotide in cells, preferably muscle cells. Examples of such moieties are cholesterols, carbohydrates, vitamins, biotin, lipids, phospholipids, cell-penetrating peptides including but not limited to antennapedia, TAT, transportan and positively charged amino acids such as oligoarginine, poly-arginine, oligolysine or polylysine, antigen-binding domains such as provided by an antibody, a Fab fragment of an antibody, or a single chain antigen binding domain such as a cameloid single domain antigen-binding domain.

A preferred antisense oligonucleotide comprises a peptide-linked PMO.

A preferred antisense oligonucleotide comprising one or more nucleotide analogs or equivalents of the invention modulates splicing in one or more muscle cells, including heart muscle cells, upon systemic delivery. In this respect, systemic delivery of an antisense oligonucleotide comprising a specific nucleotide analog or equivalent might result in targeting a subset of muscle cells, while an antisense oligonucleotide comprising a distinct nucleotide analog or equivalent might result in targeting of a different subset of muscle cells. Therefore, in one embodiment it is preferred to use a combination of antisense oligonucleotides comprising different nucleotide analogs or equivalents for inducing skipping of exon 43, 46, 50, 51, 52, or 53 of the human DMD pre-mRNA.

A cell can be provided with a molecule capable of interfering with essential sequences that result in highly efficient skipping of exon 43, exon 46, exon 50, exon 51, exon 52 or exon 53 of the human DMD pre-mRNA by plasmid-derived antisense oligonucleotide expression or viral expression provided by adenovirus- or adeno-associated virus-based vectors. In a preferred embodiment, there is provided a viral-based expression vector comprising an expression cassette that drives expression of a molecule as identified herein. Expression is preferably driven by a polymerase III promoter, such as a U1, a U6, or a U7 RNA promoter. A muscle or myogenic cell can be provided with a plasmid for antisense oligonucleotide expression by providing the plasmid in an aqueous solution. Alternatively, a plasmid can be provided by transfection using known transfection agentia such as, for example, LipofectAMINE™ 2000 (Invitrogen) or polyethyleneimine (PEI; ExGen500 (MBI Fermentas)), or derivatives thereof.

One preferred antisense oligonucleotide expression system is an adenovirus associated virus (AAV)-based vector. Single chain and double chain AAV-based vectors have been developed that can be used for prolonged expression of small antisense nucleotide sequences for highly efficient skipping of exon 43, 46, 50, 51, 52 or 53 of the DMD pre-mRNA.

A preferred AAV-based vector comprises an expression cassette that is driven by a polymerase III-promoter (Pol III). A preferred Pol III promoter is, for example, a U1, a U6, or a U7 RNA promoter.

The invention therefore also provides a viral-based vector, comprising a Pol III-promoter driven expression cassette for expression of one or more antisense sequences of the invention for inducing skipping of exon 43, exon 46, exon 50, exon 51, exon 52 or exon 53 of the human DMD pre-mRNA.

Pharmaceutical Composition

If required, a molecule or a vector expressing an antisense oligonucleotide of the invention can be incorporated into a pharmaceutically active mixture or composition by adding a pharmaceutically acceptable carrier.

Therefore, in a further aspect, the invention provides a composition, preferably a pharmaceutical composition comprising a molecule comprising an antisense oligonucleotide according to the invention, and/or a viral-based vector expressing the antisense sequence(s) according to the invention and a pharmaceutically acceptable carrier.

A preferred pharmaceutical composition comprises a molecule as defined herein and/or a vector as defined herein, and a pharmaceutical acceptable carrier or excipient, optionally combined with a molecule and/or a vector as defined herein which is able to induce skipping of exon 6, 7, 11, 17, 19, 21, 43, 44, 45, 50, 51, 52, 53, 55, 57, 59, 62, 63, 65, 66, 69, or 75 of the DMD pre-mRNA. Preferred molecules able to induce skipping of any of these exon are identified in any one of Tables 1 to 7.

Preferred excipients include excipients capable of forming complexes, vesicles and/or liposomes that deliver such a molecule as defined herein, preferably an oligonucleotide complexed or trapped in a vesicle or liposome through a cell membrane. Many of these excipients are known in the art. Suitable excipients comprise polyethylenimine and derivatives, or similar cationic polymers, including polypropyleneimine or polyethylenimine copolymers (PECs) and derivatives, ExGen 500, synthetic amphiphils (SAINT-18), Lipofectin™, DOTAP and/or viral capsid proteins that are capable of self assembly into particles that can deliver such molecule, preferably an oligonucleotide as defined herein to a cell, preferably a muscle cell. Such excipients have been shown to efficiently deliver (oligonucleotide such as antisense) nucleic acids to a wide variety of cultured cells, including muscle cells. Their high transfection potential is combined with an excepted low to moderate toxicity in terms of overall cell survival. The ease of structural modification can be used to allow further modifications and the analysis of their further (in vivo) nucleic acid transfer characteristics and toxicity.

Lipofectin represents an example of a liposomal transfection agent. It consists of two lipid components, a cationic lipid N-[1-(2,3 dioleoyloxy)propyl]-N,N,N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such like diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver a molecule or a compound as defined herein, preferably an oligonucleotide across cell membranes into cells.

In addition to these common nanoparticle materials, the cationic peptide protamine offers an alternative approach to formulate a compound as defined herein, preferably an oligonucleotide as colloids. This colloidal nanoparticle system can form so called proticles, which can be prepared by a simple self-assembly process to package and mediate intracellular release of a compound as defined herein, preferably an oligonucleotide. The skilled person may select and adapt any of the above or other commercially available alternative excipients and delivery systems to package and deliver a compound as defined herein, preferably an oligonucleotide for use in the current invention to deliver said compound for the treatment of Duchenne Muscular Dystrophy or Becker Muscular Dystrophy in humans.

In addition, a compound as defined herein, preferably an oligonucleotide could be covalently or non-covalently linked to a targeting ligand specifically designed to facilitate the uptake in to the cell, cytoplasm and/or its nucleus. Such ligand could comprise (i) a compound (including but not limited to peptide(-like) structures) recognising cell, tissue or organ specific elements facilitating cellular uptake and/or (ii) a chemical compound able to facilitate the uptake in to cells and/or the intracellular release of an a compound as defined herein, preferably an oligonucleotide from vesicles, e.g. endosomes or lysosomes.

Therefore, in a preferred embodiment, a compound as defined herein, preferably an oligonucleotide are formulated in a medicament which is provided with at least an excipient and/or a targeting ligand for delivery and/or a delivery device of said compound to a cell and/or enhancing its intracellular delivery. Accordingly, the invention also encompasses a pharmaceutically acceptable composition comprising a compound as defined herein, preferably an oligonucleotide and further comprising at least one excipient and/or a targeting ligand for delivery and/or a delivery device of said compound to a cell and/or enhancing its intracellular delivery.

It is to be understood that a molecule or compound or oligonucleotide may not be formulated in one single composition or preparation. Depending on their identity, the skilled person will know which type of formulation is the most appropriate for each compound.

In a preferred embodiment, an in vitro concentration of a molecule or an oligonucleotide as defined herein, which is ranged between 0.1 nM and 1 µM is used. More preferably, the concentration used is ranged between 0.3 to 400 nM, even more preferably between 1 to 200 nM. A molecule or an oligonucleotide as defined herein may be used at a dose which is ranged between 0.1 and 20 mg/kg, preferably 0.5 and 10 mg/kg. If several molecules or oligonucleotides are used, these concentrations may refer to the total concentration of oligonucleotides or the concentration of each oligonucleotide added. The ranges of concentration of oligonucleotide(s) as given above are preferred concentrations for in vitro or ex vivo uses. The skilled person will understand that depending on the oligonucleotide(s) used, the target cell to be treated, the gene target and its expression levels, the medium used and the transfection and incubation conditions, the concentration of oligonucleotide(s) used may further vary and may need to be optimised any further.

More preferably, a compound preferably an oligonucleotide to be used in the invention to prevent, treat DMD or BMD are synthetically produced and administered directly to a cell, a tissue, an organ and/or patients in formulated form in a pharmaceutically acceptable composition or preparation. The delivery of a pharmaceutical composition to the subject is preferably carried out by one or more parenteral injections, e.g. intravenous and/or subcutaneous and/or intramuscular and/or intrathecal and/or intraventricular administrations, preferably injections, at one or at multiple sites in the human body.

A preferred oligonucleotide as defined herein optionally comprising one or more nucleotide analogs or equivalents of the invention modulates splicing in one or more muscle cells, including heart muscle cells, upon systemic delivery. In this respect, systemic delivery of an oligonucleotide comprising a specific nucleotide analog or equivalent might result in targeting a subset of muscle cells, while an oligonucleotide comprising a distinct nucleotide analog or equivalent might result in targeting of a different subset of muscle cells.

In this respect, systemic delivery of an oligonucleotide comprising a specific nucleotide analog or equivalent might result in targeting a subset of muscle cells, while an oligonucleotide comprising a distinct nucleotide analog or equivalent might result in targeting a different subset of muscle cells. Therefore, in this embodiment, it is preferred to use a combination of oligonucleotides comprising different nucleotide analogs or equivalents for modulating splicing of the DMD mRNA in at least one type of muscle cells.

In a preferred embodiment, there is provided a molecule or a viral-based vector for use as a medicament, preferably for modulating splicing of the DMD pre-mRNA, more preferably for promoting or inducing skipping of any of exon 43, 46, 50-53 as identified herein.

Use

In yet a further aspect, the invention provides the use of an antisense oligonucleotide or molecule according to the invention, and/or a viral-based vector that expresses one or more antisense sequences according to the invention and/or a pharmaceutical composition, for modulating splicing of the DMD pre-mRNA. The splicing is preferably modulated in a human myogenic cell or muscle cell in vitro. More preferred is that splicing is modulated in a human muscle cell in vivo. Accordingly, the invention further relates to the use of the molecule as defined herein and/or the vector as defined herein and/or or the pharmaceutical composition as defined herein for modulating splicing of the DMD pre-mRNA or for the preparation of a medicament for the treatment of a DMD or BMD patient.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a molecule or a viral-based vector or a composition as defined herein may comprise additional component(s) than the ones specifically identified, said additional component(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

Each embodiment as identified herein may be combined together unless otherwise indicated. All patent and literature references cited in the present specification are hereby incorporated by reference in their entirety.

The following examples are offered for illustrative purposes only, and are not intended to limit the scope of the present invention in any way.

FIGURE LEGENDS

FIG. 1. In human control myotubes, a series of AONs (PS237, PS238, and PS240; SEQ ID NO 65, 66, 16 respectively) targeting exon 43 was tested at 500 nM. PS237 (SEQ ID NO 65) reproducibly induced highest levels of exon43 skipping. (M: DNA size marker; NT: non-treated cells)

Figure 2:
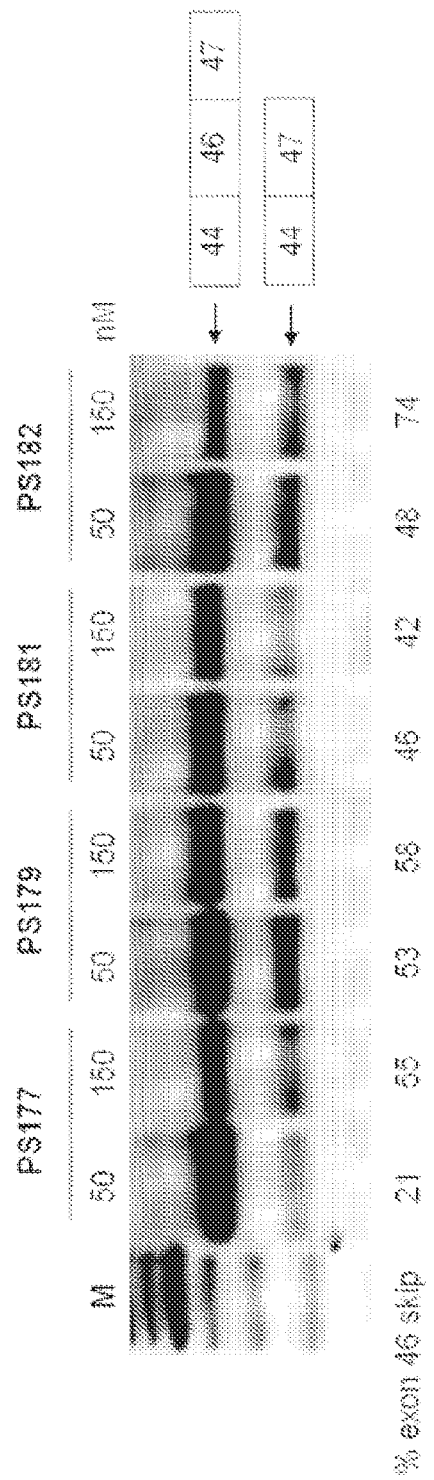

FIG. 2. In myotubes from a DMD patient with an exon 45 deletion, a series of AONs (PS177, PS179, PS181, and PS182; SEQ ID NO 91, 70, 110, and 117 respectively) targeting exon 46 was tested at two different concentrations (50 and 150 nM). PS182 (SEQ ID NO 117) reproducibly induced highest levels of exon 46 skipping. (M: DNA size marker)

Figure 3:
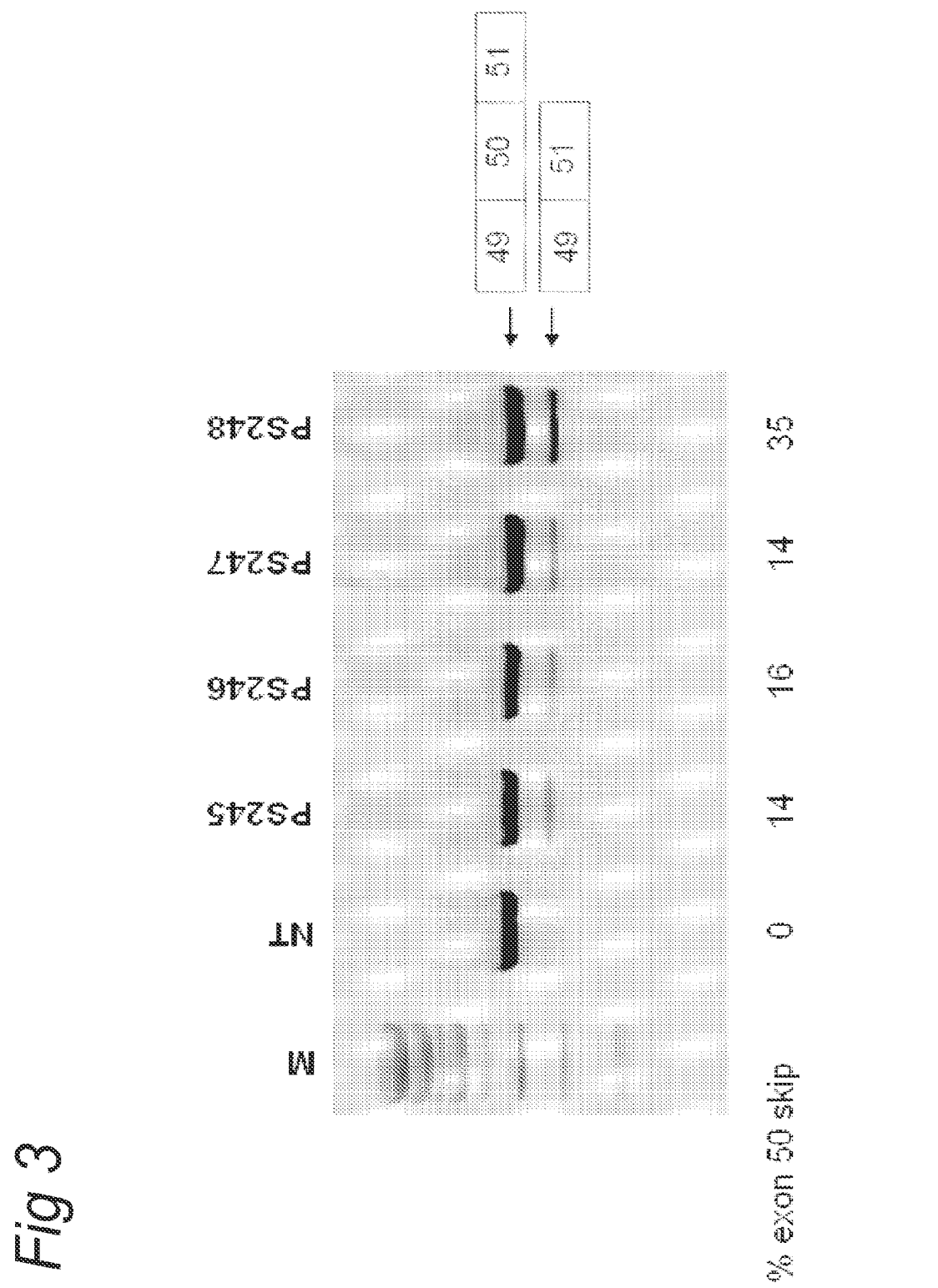

FIG. 3. In human control myotubes, a series of AONs (PS245, PS246, PS247, and PS248; SEQ ID NO 167, 165, 166, and 127 respectively) targeting exon 50 was tested at 500 nM. PS248 (SEQ ID NO 127) reproducibly induced highest levels of exon 50 skipping. (M: DNA size marker; NT: non-treated cells).

Figure 4:
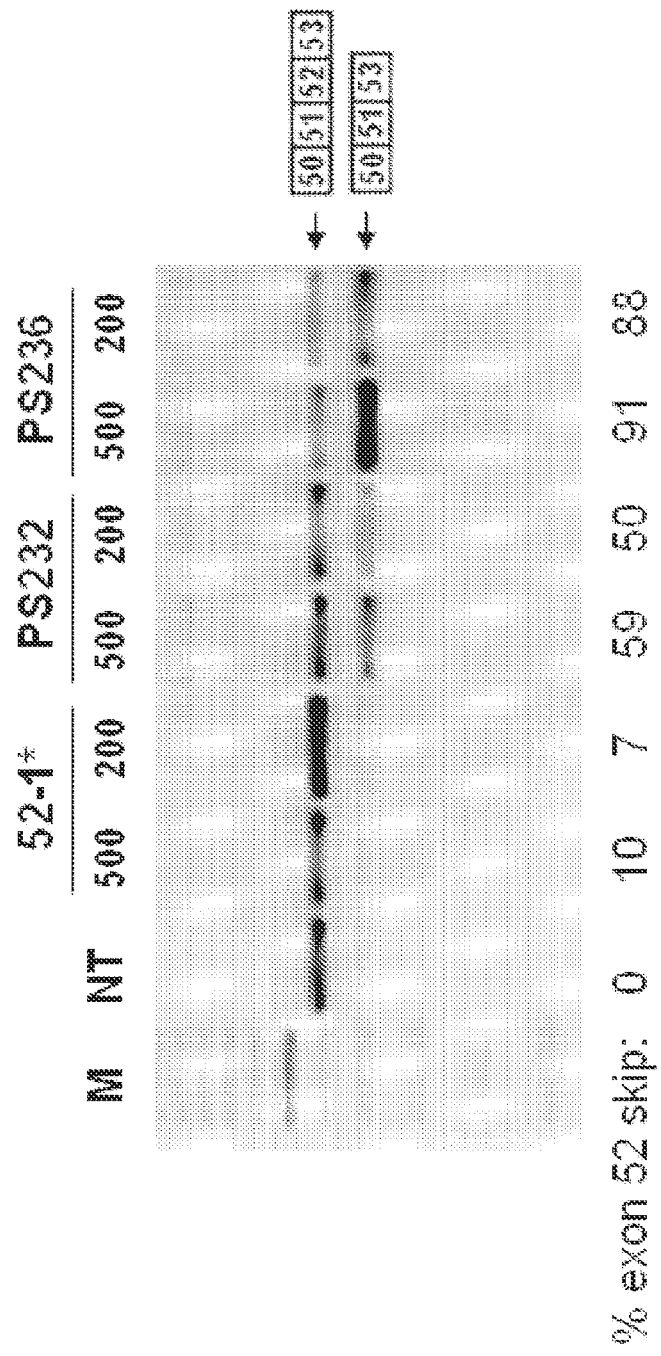

FIG. 4. In human control myotubes, two novel AONs (PS232 and PS236; SEQ ID NO 246 and 299 respectively) targeting exon 52 were tested at two different concentrations (200 and 500 nM) and directly compared to a previously described AON (52-1). PS236 (SEQ ID NO 299) reproducibly induced highest levels of exon 52 skipping. (M: DNA size marker; NT: non-treated cells).

EXAMPLES

Examples 1-4

Materials and Methods

AON design was based on (partly) overlapping open secondary structures of the target exon RNA as predicted by the m-fold program, on (partly) overlapping putative SR-protein binding sites as predicted by the ESE-finder software. AONs were synthesized by Prosensa Therapeutics B.V. (Leiden, Netherlands), and contain 2'-O-methyl RNA and full-length phosphorothioate (PS) backbones.

Tissue Culturing, Transfection and RT-PCR Analysis

Myotube cultures derived from a healthy individual ("human control") (examples 1, 3, and 4; exon 43, 50, 52 skipping) or a DMD patient carrying an exon 45 deletion (example 2; exon 46 skipping) were processed as described previously (Aartsma-Rus et al., Neuromuscul. Disord. 2002; 12: S71-77 and Hum Mol Genet 2003; 12(8): 907-14). For the screening of AONs, myotube cultures were transfected with 50 nM and 150 nM (example 2), 200 nM and 500 nM (example 4) or 500 nM only (examples 1 and 3) of each AON. Transfection reagent UNIFectylin (Prosensa Therapeutics BV, Netherlands) was used, with 2 µl UNIFectylin per µg AON. Exon skipping efficiencies were determined by nested RT-PCR analysis using primers in the exons flanking the targeted exons (43, 46, 50, 51, 52, or 53). PCR fragments were isolated from agarose gels for sequence verification. For quantification, the PCR products were analyzed using the DNA 1000 LabChips Kit on the Agilent 2100 bioanalyzer (Agilent Technologies, USA).

Results

DMD Exon 43 Skipping.

A series of AONs targeting sequences within exon 43 were designed and transfected in healthy control myotube cultures. Subsequent RT-PCR and sequence analysis of isolated RNA demonstrated that almost all AONs targeting a continuous nucleotide stretch within exon 43 herein defined as SEQ ID NO 2, was indeed capable of inducing exon 43 skipping. PS237 (SEQ ID NO: 65) reproducibly induced highest levels of exon 43 skipping (up to 66%) at 500 nM, as shown in FIG. 1. For comparison, also PS238 and PS240 are shown, inducing exon 43 skipping levels up to 13% and 36% respectively (FIG. 1). The precise skipping of exon 43 was confirmed by sequence analysis of the novel smaller transcript fragments. No exon 43 skipping was observed in non-treated cells (NT).

DMD Exon 46 Skipping.

A series of AONs targeting sequences within exon 46 were designed and transfected in myotube cultures derived from a DMD patient carrying an exon 45 deletion in the DMD gene. For patients with such mutation antisense-induced exon 46 skipping would induce the synthesis of a novel, BMD-like dystrophin protein that may indeed alleviate one or more symptoms of the disease. Subsequent RT-PCR and sequence analysis of isolated RNA demonstrated that almost all AONs targeting a continuous nucleotide stretch within exon 46 herein defined as SEQ ID NO 3, was indeed capable of inducing exon 46 skipping, even at relatively low AON concentrations of 50 nM. PS182 (SEQ ID NO: 117) reproducibly induced highest levels of exon 46 skipping (up to 50% at 50 nM and 74% at 150 nM), as shown in FIG. 2. For comparison, also PS177, PS179, and PS181 are shown, inducing exon 46 skipping levels up to 55%, 58% and 42% respectively at 150 nM (FIG. 2). The precise skipping of exon 46 was confirmed by sequence analysis of the novel smaller transcript fragments. No exon 46 skipping was observed in non-treated cells (NT).

DMD Exon 50 Skipping.

A series of AONs targeting sequences within exon 50 were designed and transfected in healthy control myotube cultures. Subsequent RT-PCR and sequence analysis of isolated RNA demonstrated that almost all AONs targeting a continuous nucleotide stretch within exon 50 herein defined as SEQ ID NO 4, was indeed capable of inducing exon 50 skipping. PS248 (SEQ ID NO: 127) reproducibly induced highest levels of exon 50 skipping (up to 35% at 500 nM), as shown in FIG. 3. For comparison, also PS245, PS246, and PS247 are shown, inducing exon 50 skipping levels up to 14-16% at 500 nM (FIG. 3). The precise skipping of exon 50 was confirmed by sequence analysis of the novel smaller transcript fragments. No exon 50 skipping was observed in non-treated cells (NT).

DMD Exon 51 Skipping.

A series of AONs targeting sequences within exon 51 were designed and transfected in healthy control myotube cultures. Subsequent RT-PCR and sequence analysis of isolated RNA demonstrated that almost all AONs targeting a continuous nucleotide stretch within exon 51 herein defined as SEQ ID NO 5, was indeed capable of inducing exon 51 skipping. The AON with SEQ ID NO 180 reproducibly induced highest levels of exon 51 skipping (not shown).

DMD Exon 52 Skipping.

A series of AONs targeting sequences within exon 52 were designed and transfected in healthy control myotube cultures. Subsequent RT-PCR and sequence analysis of isolated RNA demonstrated that almost all AONs targeting a continuous nucleotide stretch within exon 52 herein defined as SEQ ID NO 6, was indeed capable of inducing exon 52 skipping. PS236 (SEQ ID NO: 299) reproducibly induced highest levels of exon 52 skipping (up to 88% at 200 nM and 91% at 500 nM), as shown in FIG. 4. For comparison, also PS232 and AON 52-1 (previously published by Aartsma-Rus et al. *Oligonucleotides* 2005) are shown, inducing exon 52 skipping at levels up to 59% and 10% respectively when applied at 500 nM (FIG. 4). The precise skipping of exon 52 was confirmed by sequence analysis of the novel smaller transcript fragments. No exon 52 skipping was observed in non-treated cells (NT).

DMD Exon 53 Skipping.

A series of AONs targeting sequences within exon 53 were designed and transfected in healthy control myotube cultures. Subsequent RT-PCR and sequence analysis of isolated RNA demonstrated that almost all AONs targeting a continuous nucleotide stretch within exon 53 herein defined as SEQ ID NO 7, was indeed capable of inducing exon 53 skipping. The AON with SEQ ID NO 328 reproducibly induced highest levels of exon 53 skipping (not shown).

```
Sequence listing:
DMD gene amino acid sequence
SEQ ID NO 1:
MLWWEEVEDCYEREDVQKKTFTKWVNAQFSKFGKQHIENLFSDLQDGRRLLDLLEGLTGQKL

PKEKGSTRVHALNNVNKALRVLQNNNVDLVNIGSTDIVDGNHKLTLGLIWNIILHWQVKNVMK

NIMAGLQQTNSEKILLSWVRQSTRNYPQVNVINFTTSWSDGLALNALIHSHRPDLFDWNSVVCQ

QSATQRLEHAFNIARYQLGIEKLLDPEDVDTTYPDKKSILMYITSLFQVLPQQVSIEAIQEVEMLP

RPPKVTKEEHFQLHHQMHYSQQITVSLAQGYERTSSPKPRFKSYAYTQAAYVTTSDPTRSPFPSQ

HLEAPEDKSFGSSLMESEVNLDRYQTALEEVLSWLLSAEDTLQAQGEISNDVEVVKDQFHTHEG

YMMDLTAHQGRVGNILQLGSKLIGTGKLSEDEETEVQEQMNLLNSRWECLRVASMEKQSNLH

RVLMDLQNQKLKELNDWLTKTEERTRKMEEEPLGPDLEDLKRQVQQHKVLQEDLEQEQVRVN

SLTHMVVVVDESSGDHATAALEEQLKVLGDRWANICRWTEDRWVLLQDILLKWQRLTEEQCL

FSAWLSEKEDAVNKIHTTGFKDQNEMLSSLQKLAVLKADLEKKKQSMGKLYSLKQDLLSTLKN

KSVTQKTEAWLDNFARCWDNLVQKLEKSTAQISQAVTTTQPSLTQTTVMETVTTVTTREQILV

KHAQEELPPPPPQKKRQITVDSEIRKRLDVDITELHSWITRSEAVLQSPEFAIFRKEGNFSDLKEK

VNAIEREKAEKFRKLQDASRSAQALVEQMVNEGVNADSIKQASEQLNSRWIEFCQLLSERLNW

LEYQNNIIAFYNQLQQLEQMTTTAENWLKIQPTTPSEPTAIKSQLKICKDEVNRLSGLQPQIERLK

IQSIALKEKGQGPMFLDADFVAFTNHFKQVFSDVQAREKELQTIFDTLPPMRYQETMSAIRTWV

QQSETKLSIPQLSVTDYEIMEQRLGELQALQSSLQEQQSGLYYLSTTVKEMSKKAPSEISRKYQS

EFEEIEGRWKKLSSQLVEHCQKLEEQMNKLRKIQNHIQTLKKWMAEVDVFLKEEWPALGDSEI
```

```
-continued
LKKQLKQCRLLVSDIQTIQPSLNSVNEGGQKIKNEAEPEFASRLETELKELNTQWDHMCQQVYA

RKEALKGGLEKTVSLQKDLSEMHEWMTQAEEEYLERDFEYKTPDELQKAVEEMKRAKEEAQQ

KEAKVKLLTESVNSVIAQAPPVAQEALKKELETLTTNYQWLCTRLNGKCKTLEEVWACWHELL

SYLEKANKWLNEVEFKLKTTENIPGGAEEISEVLDSLENLMRHSEDNPNQIRILAQTLTDGGVM

DELINEELETFNSRWRELHEEAVRRQKLLEQSIQSAQETEKSLHLIQESLTFIDKQLAAYIADKVD

AAQMPQEAQKIQSDLTSHEISLEEMKKHNQGKEAAQRVLSQIDVAQKKLQDVSMKFRLFQKPA

NFEQRLQESKMILDEVKMHLPALETKSVEQEVVQSQLNHCVNLYKSLSEVKSEVEMVIKTGRQI

VQKKQTENPKELDERVTALKLHYNELGAKVTERKQQLEKCLKLSRKMRKEMNVLTEWLAAT

DMELTKRSAVEGMPSNLDSEVAWGKATQKEIEKQKVHLKSITEVGEALKTVLGKKETLVEDKL

SLLNSNWIAVTSRAEEWLNLLLEYQKHMETFDQNVDHITKWIIQADTLLDESEKKKPQQKEDVL

KRLKAELNDIRPKVDSTRDQAANLMANRGDHCRKLVEPQISELNHRFAAISHRIKTGKASIPLKE

LEQFNSDIQKLLEPLEAEIQQGVLKEEDFNKDMNEDNEGTVKELLQRGDNLQQRITDERKREEI

KIKQQLLQTKHNALKDLRSQRRKKALEISHQWYQYKRQADDLLKCLDDIEKKLASLPEPRDER

KIKEIDRELQKKKEELNAVRRQAEGLSEDGAAMAVEPTQIQLSKRWREIESKFAQFRRLNFAQIH

TVREETMMVMTEDMPLEISYVPSTYLTEITHVSQALLEVEQLLNAPDLCAKDFEDLFKQEESLK

NIKDSLQQSSGRIDIIHSKKTAALQSATPVERVKLQEALSQLDFQWEKVNKMYKDRQGRFDRSV

EKWRRFHYDIKIFNQWLTEAEQFLRKTQIPENWEHAKYKWYLKELQDGIGQRQTVVRTLNATG

EEIIQQSSKTDASILQEKLGSLNLRWQEVCKQLSDRKKRLEEQKNILSEFQRDLNEFVLWLEEAD

NIASIPLEPGKEQQLKEKLEQVKLLVEELPLRQGILKQLNETGGPVLVSAPISPEEQDKLENKLKQ

TNLQWIKVSRALPEKQGEIEAQIKDLGQLEKKLEDLEEQLNHLLLWLSPIRNQLEIYNQPNQEGP

FDVQETEIAVQAKQPDVEEILSKGQHLYKEKPATQPVKRKLEDLSSEWKAVNRLLQELRAKQP

DLAPGLTTIGASPTQTVTLVTQPVVTKETAISKLEMPSSLMLEVPALADFNRAWTELTDWLSLL

DQVIKSQRVMVGDLEDINEMIIKQKATMQDLEQRRPQLEELITAAQNLKNKTSNQEARTIITDRI

ERIQNQWDEVQEHLQNRRQQLNEMLKDSTQWLEAKEEAEQVLGQARAKLESWKEGPYTVDAI

QKKITETKQLAKDLRQWQTNVDVANDLALKLLRDYSADDTRKVHMITENINASWRSIHKRVSE

REAALEETHRLLQQFPLDLEKFLAWLTEAETTANVLQDATRKERLLEDSKGVKELMKQWQDL

QGEIEAHTDVYHNLDENSQKILRSLEGSDDAVLLQRRLDNMNFKWSELRKKSLNIRSHLEASSD

QWKRLHLSLQELLVWLQLKDDELSRQAPIGGDFPAVQKQNDVHRAFKRELKTKEPVIMSTLET

VRIFLTEQPLEGLEKLYQEPRELPPEERAQNVTRLLRKQAEEVNTEWEKLNLHSADWQRKIDET

LERLQELQEATDELDLKLRQAEVIKGSWQPVGDLLIDSLQDHLEKVKALRGEIAPLKENVSHVN

DLARQLTTLGIQLSPYNLSTLEDLNTRWKLLQVAVEDRVRQLHEAHRDFGPASQHFLSTSVQGP

WERAISPNKVPYYINHETQTTCWDHPKMTELYQSLADLNNVRFSAYRTAMKLRRLQKALCLDL

LSLSAACDALDQHNLKQNDQPMDILQIINCLTTIYDRLEQEHNNLVNVPLCVDMCLNWLLNVY

DTGRTGRIRVLSHKTGIISLCKAHLEDKYRYLFKQVASSTGFCDQRRLGLLLHDSIQIPRQLGEVA

SFGGSNIEPSVRSCFQFANNKPEIEAALFLDWMRLEPQSMVWLPVLHRVAAAETAKHQAKCNIC

KECPIIGFRYRSLKFHFNYDICQSCFFSGRVAKGHMHYPMVEYCTPTTSGEDVRDFAKVLKNKF

RTKRYFAKHPRMGYLPVQTVLEGDNMETPVTLINFWPVDSAPASSPQLSHDDTHSRIEHYASRL

AEMENSNGSYLNDSISPNESIDDEHLLIQHYCQSLNQDSPLSQPRSPAQILISLESEERGELERILAD

LEEENRNLQAEYDRLKQQHEHKGLSPLPSPPEMMPTSPQSPRDAELIAEAKLLRQHKGRLEARM

QILEDHNKQLESQLHRLRQLLEQPQAEAKVNGTTVSSPSTSLQRSDSSQPMLLRVVGSQTSDSM

GEEDLLSPPQDTSTGLEEVMEQLNNSFPSSRGRNTPGKPMREDTM
```

-continued

SEQ ID NO 2 (exon 43):
AGAUAGUCUACAACAAAGCUCAGGUCGGAUUGACAUUAUUCAUAGCAAGAAGACAGCAG

CAUUGCAAAGUGCAACGCCUGUGG

SEQ ID NO 3 (exon 46):
UUAUGGUUGGAGGAAGCAGAUAACAUUGCUAGUAUCCCACUUGAACCUGGAAAAGAGCA

GCAACUAAAAGAAAAGC

SEQ ID NO 4 (exon 50):
'GGCGGTAAACCGUUUACUUCAAGAGCUGAGGGCAAAGCAGCCUGACCUAGC

UCCUGGACUGACCACUAUUGG

SEQ ID NO 5 (exon 51):
CUCCUACUCAGACUGUUACUCUGGUGACACAACCUGUGGUUACUAAGGAAACUGCCAUC

UCCAAACUAGAAAUGCCAUCUUCCUUGAUGUUGGAGGUAC

SEQ ID NO 6 (exon 52):
AUGCAGGAUUUGGAACAGAGGCGUCCCCAGUUGGAAGAACUCAUUACCGCUGCCCAAAA

UUUGAAAAACAAGACCAGCAAUCAAGAGGCU

SEQ ID NO 7 (exon 53):
AAAUGUUAAAGGAUUCAACACAAUGGCUGGAAGCUAAGGAAGAAGCUGAGCAGGUCUUA

GGACAGGCCAGAG

TABLE 1

| | oligonucleotides for skipping DMD Gene Exon 43 |
|---|---|
| SEQ ID NO 8 | CCACAGGCGUUGCACUUUGCAAUGC |
| SEQ ID NO 9 | CACAGGCGUUGCACUUUGCAAUGCU |
| SEQ ID NO 10 | ACAGGCGUUGCACUUUGCAAUGCUG |
| SEQ ID NO 11 | CAGGCGUUGCACUUUGCAAUGCUGC |
| SEQ ID NO 12 | AGGCGUUGCACUUUGCAAUGCUGCU |
| SEQ ID NO 13 | GGCGUUGCACUUUGCAAUGCUGCUG |
| SEQ ID NO 14 | GCGUUGCACUUUGCAAUGCUGCUGU |
| SEQ ID NO 15 | CGUUGCACUUUGCAAUGCUGCUGUC |
| SEQ ID NO 16 PS240 | CGUUGCACUUUGCAAUGCUGCUG |
| SEQ ID NO 17 | GUUGCACUUUGCAAUGCUGCUGUCU |
| SEQ ID NO 18 | UUGCACUUUGCAAUGCUGCUGUCUU |
| SEQ ID NO 19 | UGCACUUUGCAAUGCUGCUGUCUUC |
| SEQ ID NO 20 | GCACUUUGCAAUGCUGCUGUCUUCU |
| SEQ ID NO 21 | CACUUUGCAAUGCUGCUGUCUUCUU |
| SEQ ID NO 22 | ACUUUGCAAUGCUGCUGUCUUCUUG |
| SEQ ID NO 23 | CUUUGCAAUGCUGCUGUCUUCUUGC |
| SEQ ID NO 24 | UUUGCAAUGCUGCUGUCUUCUUGCU |
| SEQ ID NO 25 | UUGCAAUGCUGCUGUCUUCUUGCUA |
| SEQ ID NO 26 | UGCAAUGCUGCUGUCUUCUUGCUAU |
| SEQ ID NO 27 | GCAAUGCUGCUGUCUUCUUGCUAUG |
| SEQ ID NO 28 | CAAUGCUGCUGUCUUCUUGCUAUGA |
| SEQ ID NO 29 | AAUGCUGCUGUCUUCUUGCUAUGAA |

TABLE 1-continued

| | oligonucleotides for skipping DMD Gene Exon 43 |
|---|---|
| SEQ ID NO 30 | AUGCUGCUGUCUUCUUGCUAUGAAU |
| SEQ ID NO 31 | UGCUGCUGUCUUCUUGCUAUGAAUA |
| SEQ ID NO 32 | GCUGCUGUCUUCUUGCUAUGAAUAA |
| SEQ ID NO 33 | CUGCUGUCUUCUUGCUAUGAAUAAU |
| SEQ ID NO 34 | UGCUGUCUUCUUGCUAUGAAUAAUG |
| SEQ ID NO 35 | GCUGUCUUCUUGCUAUGAAUAAUGU |
| SEQ ID NO 36 | CUGUCUUCUUGCUAUGAAUAAUGUC |
| SEQ ID NO 37 | UGUCUUCUUGCUAUGAAUAAUGUCA |
| SEQ ID NO 38 | GUCUUCUUGCUAUGAAUAAUGUCAA |
| SEQ ID NO 39 | UCUUCUUGCUAUGAAUAAUGUCAAU |
| SEQ ID NO 40 | CUUCUUGCUAUGAAUAAUGUCAAUC |
| SEQ ID NO 41 | UUCUUGCUAUGAAUAAUGUCAAUCC |
| SEQ ID NO 42 | UCUUGCUAUGAAUAAUGUCAAUCCG |
| SEQ ID NO 43 | CUUGCUAUGAAUAAUGUCAAUCCGA |
| SEQ ID NO 44 | UUGCUAUGAAUAAUGUCAAUCCGAC |
| SEQ ID NO 45 | UGCUAUGAAUAAUGUCAAUCCGACC |
| SEQ ID NO 46 | GCUAUGAAUAAUGUCAAUCCGACCU |
| SEQ ID NO 47 | CUAUGAAUAAUGUCAAUCCGACCUG |
| SEQ ID NO 48 | UAUGAAUAAUGUCAAUCCGACCUGA |
| SEQ ID NO 49 | AUGAAUAAUGUCAAUCCGACCUGAG |
| SEQ ID NO 50 | UGAAUAAUGUCAAUCCGACCUGAGC |
| SEQ ID NO 51 | GAAUAAUGUCAAUCCGACCUGAGCU |
| SEQ ID NO 52 | AAUAAUGUCAAUCCGACCUGAGCUU |

TABLE 1-continued

| oligonucleotides for skipping DMD Gene Exon 43 | |
|---|---|
| SEQ ID NO 53 | AUAAUGUCAAUCCGACCUGAGCUUU |
| SEQ ID NO 54 | UAAUGUCAAUCCGACCUGAGCUUUG |
| SEQ ID NO 55 | AAUGUCAAUCCGACCUGAGCUUUGU |
| SEQ ID NO 56 | AUGUCAAUCCGACCUGAGCUUUGUU |
| SEQ ID NO 57 | UGUCAAUCCGACCUGAGCUUUGUUG |
| SEQ ID NO 58 | GUCAAUCCGACCUGAGCUUUGUUGU |
| SEQ ID NO 59 | UCAAUCCGACCUGAGCUUUGUUGUA |
| SEQ ID NO 60 | CAAUCCGACCUGAGCUUUGUUGUAG |
| SEQ ID NO 61 | AAUCCGACCUGAGCUUUGUUGUAGA |
| SEQ ID NO 62 | AUCCGACCUGAGCUUUGUUGUAGAC |
| SEQ ID NO 63 | UCCGACCUGAGCUUUGUUGUAGACU |
| SEQ ID NO 64 | CCGACCUGAGCUUUGUUGUAGACUA |
| SEQ ID NO 65 PS237 | CGACCUGAGCUUUGUUGUAG |
| SEQ ID NO 66 PS238 | CGACCUGAGCUUUGUUGUAGACUAU |
| SEQ ID NO 67 | GACCUGAGCUUUGUUGUAGACUAUC |
| SEQ ID NO 68 | ACCUGAGCUUUGUUGUAGACUAUCA |
| SEQ ID NO 69 | CCUGA GCUUU GUUGU AGACU AUC |

TABLE 2

| oligonucleotides for skipping DMD Gene Exon 46 | |
|---|---|
| SEQ ID NO 70 PS179 | GCUUUUCUUUUAGUUGCUGCUCUUU |
| SEQ ID NO 71 | CUUUUCUUUUAGUUGCUGCUCUUUU |
| SEQ ID NO 72 | UUUUCUUUUAGUUGCUGCUCUUUUC |
| SEQ ID NO 73 | UUUCUUUUAGUUGCUGCUCUUUUCC |
| SEQ ID NO 74 | UUCUUUUAGUUGCUGCUCUUUUCCA |
| SEQ ID NO 75 | UCUUUUAGUUGCUGCUCUUUUCCAG |
| SEQ ID NO 76 | CUUUUAGUUGCUGCUCUUUUCCAGG |
| SEQ ID NO 77 | UUUUAGUUGCUGCUCUUUUCCAGGU |
| SEQ ID NO 78 | UUUAGUUGCUGCUCUUUUCCAGGUU |
| SEQ ID NO 79 | UUAGUUGCUGCUCUUUUCCAGGUUC |
| SEQ ID NO 80 | UAGUUGCUGCUCUUUUCCAGGUUCA |
| SEQ ID NO 81 | AGUUGCUGCUCUUUUCCAGGUUCAA |
| SEQ ID NO 82 | GUUGCUGCUCUUUUCCAGGUUCAAG |
| SEQ ID NO 83 | UUGCUGCUCUUUUCCAGGUUCAAGU |
| SEQ ID NO 84 | UGCUGCUCUUUUCCAGGUUCAAGUG |
| SEQ ID NO 85 | GCUGCUCUUUUCCAGGUUCAAGUGG |
| SEQ ID NO 86 | CUGCUCUUUUCCAGGUUCAAGUGGG |

TABLE 2-continued

| oligonucleotides for skipping DMD Gene Exon 46 | |
|---|---|
| SEQ ID NO 87 | UGCUCUUUUCCAGGUUCAAGUGGGA |
| SEQ ID NO 88 | GCUCUUUUCCAGGUUCAAGUGGGAC |
| SEQ ID NO 89 | CUCUUUUCCAGGUUCAAGUGGGAUA |
| SEQ ID NO 90 | UCUUUUCCAGGUUCAAGUGGGAUAC |
| SEQ ID NO 91 PS177 | UCUUUUCCAGGUUCAAGUGG |
| SEQ ID NO 92 | CUUUUCCAGGUUCAAGUGGGAUACU |
| SEQ ID NO 93 | UUUUCCAGGUUCAAGUGGGAUACUA |
| SEQ ID NO 94 | UUUCCAGGUUCAAGUGGGAUACUAG |
| SEQ ID NO 95 | UUCCAGGUUCAAGUGGGAUACUAGC |
| SEQ ID NO 96 | UCCAGGUUCAAGUGGGAUACUAGCA |
| SEQ ID NO 97 | CCAGGUUCAAGUGGGAUACUAGCAA |
| SEQ ID NO 98 | CAGGUUCAAGUGGGAUACUAGCAAU |
| SEQ ID NO 99 | AGGUUCAAGUGGGAUACUAGCAAUG |
| SEQ ID NO 100 | GGUUCAAGUGGGAUACUAGCAAUGU |
| SEQ ID NO 101 | GUUCAAGUGGGAUACUAGCAAUGUU |
| SEQ ID NO 102 | UUCAAGUGGGAUACUAGCAAUGUUA |
| SEQ ID NO 103 | UCAAGUGGGAUACUAGCAAUGUUAU |
| SEQ ID NO 104 | CAAGUGGGAUACUAGCAAUGUUAUC |
| SEQ ID NO 105 | AAGUGGGAUACUAGCAAUGUUAUCU |
| SEQ ID NO 106 | AGUGGGAUACUAGCAAUGUUAUCUG |
| SEQ ID NO 107 | GUGGGAUACUAGCAAUGUUAUCUGC |
| SEQ ID NO 108 | UGGGAUACUAGCAAUGUUAUCUGCU |
| SEQ ID NO 109 | GGGAUACUAGCAAUGUUAUCUGCUU |
| SEQ ID NO 110 PS181 | GGAUACUAGCAAUGUUAUCUGCUUC |
| SEQ ID NO 111 | GAUACUAGCAAUGUUAUCUGCUUCC |
| SEQ ID NO 112 | AUACUAGCAAUGUUAUCUGCUUCCU |
| SEQ ID NO 113 | UACUAGCAAUGUUAUCUGCUUCCUC |
| SEQ ID NO 114 | ACUAGCAAUGUUAUCUGCUUCCUCC |
| SEQ ID NO 115 | CUAGCAAUGUUAUCUGCUUCCUCCA |
| SEQ ID NO 116 | UAGCAAUGUUAUCUGCUUCCUCCAA |
| SEQ ID NO 117 PS182 | AGCAAUGUUAUCUGCUUCCUCCAAC |
| SEQ ID NO 118 | GCAAUGUUAUCUGCUUCCUCCAACC |
| SEQ ID NO 119 | CAAUGUUAUCUGCUUCCUCCAACCA |
| SEQ ID NO 120 | AAUGUUAUCUGCUUCCUCCAACCAU |
| SEQ ID NO 121 | AUGUUAUCUGCUUCCUCCAACCAUA |
| SEQ ID NO 122 | UGUUAUCUGCUUCCUCCAACCAUAA |

TABLE 3

| | oligonucleotides for skipping DMD Gene Exon 50 |
|---|---|
| SEQ ID NO 123 | CCAAUAGUGGUCAGUCCAGGAGCUA |
| SEQ ID NO 124 | CAAUAGUGGUCAGUCCAGGAGCUAG |
| SEQ ID NO 125 | AAUAGUGGUCAGUCCAGGAGCUAGG |
| SEQ ID NO 126 | AUAGUGGUCAGUCCAGGAGCUAGGU |
| SEQ ID NO 127 PS248 | AUAGUGGUCAGUCCAGGAGCU |
| SEQ ID NO 128 | UAGUGGUCAGUCCAGGAGCUAGGUC |
| SEQ ID NO 129 | AGUGGUCAGUCCAGGAGCUAGGUCA |
| SEQ ID NO 130 | GUGGUCAGUCCAGGAGCUAGGUCAG |
| SEQ ID NO 131 | UGGUCAGUCCAGGAGCUAGGUCAGG |
| SEQ ID NO 132 | GGUCAGUCCAGGAGCUAGGUCAGGC |
| SEQ ID NO 133 | GUCAGUCCAGGAGCUAGGUCAGGCU |
| SEQ ID NO 134 | UCAGUCCAGGAGCUAGGUCAGGCUG |
| SEQ ID NO 135 | CAGUCCAGGAGCUAGGUCAGGCUGC |
| SEQ ID NO 136 | AGUCCAGGAGCUAGGUCAGGCUGCU |
| SEQ ID NO 137 | GUCCAGGAGCUAGGUCAGGCUGCUU |
| SEQ ID NO 138 | UCCAGGAGCUAGGUCAGGCUGCUUU |
| SEQ ID NO 139 | CCAGGAGCUAGGUCAGGCUGCUUUG |
| SEQ ID NO 140 | CAGGAGCUAGGUCAGGCUGCUUUGC |
| SEQ ID NO 141 | AGGAGCUAGGUCAGGCUGCUUUGCC |
| SEQ ID NO 142 | GGAGCUAGGUCAGGCUGCUUUGCCC |
| SEQ ID NO 143 | GAGCUAGGUCAGGCUGCUUUGCCCU |
| SEQ ID NO 144 | AGCUAGGUCAGGCUGCUUUGCCCUC |
| SEQ ID NO 145 | GCUAGGUCAGGCUGCUUUGCCCUCA |
| SEQ ID NO 146 | CUAGGUCAGGCUGCUUUGCCCUCAG |
| SEQ ID NO 147 | UAGGUCAGGCUGCUUUGCCCUCAGC |
| SEQ ID NO 148 | AGGUCAGGCUGCUUUGCCCUCAGCU |
| SEQ ID NO 149 | GGUCAGGCUGCUUUGCCCUCAGCUC |
| SEQ ID NO 150 | GUCAGGCUGCUUUGCCCUCAGCUCU |
| SEQ ID NO 151 | UCAGGCUGCUUUGCCCUCAGCUCUU |
| SEQ ID NO 152 | CAGGCUGCUUUGCCCUCAGCUCUUG |
| SEQ ID NO 153 | AGGCUGCUUUGCCCUCAGCUCUUGA |
| SEQ ID NO 154 | GGCUGCUUUGCCCUCAGCUCUUGAA |
| SEQ ID NO 155 | GCUGCUUUGCCCUCAGCUCUUGAAG |
| SEQ ID NO 156 | CUGCUUUGCCCUCAGCUCUUGAAGU |
| SEQ ID NO 157 | UGCUUUGCCCUCAGCUCUUGAAGUA |
| SEQ ID NO 158 | GCUUUGCCCUCAGCUCUUGAAGUAA |
| SEQ ID NO 159 | CUUUGCCCUCAGCUCUUGAAGUAAA |
| SEQ ID NO 160 | UUUGCCCUCAGCUCUUGAAGUAAAC |
| SEQ ID NO 161 | UUGCCCUCAGCUCUUGAAGUAAACG |

TABLE 3-continued

| | oligonucleotides for skipping DMD Gene Exon 50 |
|---|---|
| SEQ ID NO 162 | UGCCCUCAGCUCUUGAAGUAAACGG |
| SEQ ID NO 163 | GCCCUCAGCUCUUGAAGUAAACGGU |
| SEQ ID NO 164 | CCCUCAGCUCUUGAAGUAAACGGUU |
| SEQ ID NO 165 PS246 | CCUCAGCUCUUGAAGUAAAC |
| SEQ ID NO 166 PS247 | CCUCAGCUCUUGAAGUAAACG |
| SEQ ID NO 167 PS245 | CUCAGCUCUUGAAGUAAACG |
| SEQ ID NO 529 | CCUCAGCUCUUGAAGUAAACGGUUU |
| SEQ ID NO 530 | CUGAGCUCUUGAAGUAAACGGUUUA |
| SEQ ID NO 531 | UCAGCUCUUGAAGUAAACGGUUUAC |
| SEQ ID NO 532 | CAGCUCUUGAAGUAAACGGUUUACC |
| SEQ ID NO 533 | AGCUCUUGAAGUAAACGGUUUACCG |
| SEQ ID NO 534 | GCUCUUGAAGUAAACGGUUUACCGC |
| SEQ ID NO 535 | CUCUUGAAGUAAACGGUUUACCGCC |

TABLE 4

| | oligonucleotides for skipping DMD Gene Exon 51 |
|---|---|
| SEQ ID NO 168 | GUACCUCCAACAUCAAGGAAGAUGG |
| SEQ ID NO 169 | UACCUCCAACAUCAAGGAAGAUGGC |
| SEQ ID NO 170 | ACCUCCAACAUCAAGGAAGAUGGCA |
| SEQ ID NO 171 | CCUCCAACAUCAAGGAAGAUGGCAU |
| SEQ ID NO 172 | CUCCAACAUCAAGGAAGAUGGCAUU |
| SEQ ID NO 173 | UCCAACAUCAAGGAAGAUGGCAUUU |
| SEQ ID NO 174 | CCAACAUCAAGGAAGAUGGCAUUUC |
| SEQ ID NO 175 | CAACAUCAAGGAAGAUGGCAUUUCU |
| SEQ ID NO 176 | AACAUCAAGGAAGAUGGCAUUUCUA |
| SEQ ID NO 177 | ACAUCAAGGAAGAUGGCAUUUCUAG |
| SEQ ID NO 178 | CAUCAAGGAAGAUGGCAUUUCUAGU |
| SEQ ID NO 179 | AUCAAGGAAGAUGGCAUUUCUAGUU |
| SEQ ID NO 180 | UCAAGGAAGAUGGCAUUUCUAGUUU |
| SEQ ID NO 181 | CAAGGAAGAUGGCAUUUCUAGUUUG |
| SEQ ID NO 182 | AAGGAAGAUGGCAUUUCUAGUUUGG |
| SEQ ID NO 183 | AGGAAGAUGGCAUUUCUAGUUUGGA |
| SEQ ID NO 184 | GGAAGAUGGCAUUUCUAGUUUGGAG |
| SEQ ID NO 185 | GAAGAUGGCAUUUCUAGUUUGGAGA |
| SEQ ID NO 186 | AAGAUGGCAUUUCUAGUUUGGAGAU |
| SEQ ID NO 187 | AGAUGGCAUUUCUAGUUUGGAGAUG |
| SEQ ID NO 188 | GAUGGCAUUUCUAGUUUGGAGAUGG |

TABLE 4-continued oligonucleotides for skipping DMD Gene Exon 51

| | |
|---|---|
| SEQ ID NO 189 | AUGGCAUUUCUAGUUUGGAGAUGGC |
| SEQ ID NO 190 | UGGCAUUUCUAGUUUGGAGAUGGCA |
| SEQ ID NO 191 | GGCAUUUCUAGUUUGGAGAUGGCAG |
| SEQ ID NO 192 | GCAUUUCUAGUUUGGAGAUGGCAGU |
| SEQ ID NO 193 | CAUUUCUAGUUUGGAGAUGGCAGUU |
| SEQ ID NO 194 | AUUUCUAGUUUGGAGAUGGCAGUUU |
| SEQ ID NO 195 | UUUCUAGUUUGGAGAUGGCAGUUUC |
| SEQ ID NO 196 | UUCUAGUUUGGAGAUGGCAGUUUCC |
| SEQ ID NO 197 | UCUAGUUUGGAGAUGGCAGUUUCCU |
| SEQ ID NO 198 | CUAGUUUGGAGAUGGCAGUUUCCUU |
| SEQ ID NO 199 | UAGUUUGGAGAUGGCAGUUUCCUUA |
| SEQ ID NO 200 | AGUUUGGAGAUGGCAGUUUCCUUAG |
| SEQ ID NO 201 | GUUUGGAGAUGGCAGUUUCCUUAGU |
| SEQ ID NO 202 | UUUGGAGAUGGCAGUUUCCUUAGUA |
| SEQ ID NO 203 | UUGGAGAUGGCAGUUUCCUUAGUAA |
| SEQ ID NO 204 | UGGAGAUGGCAGUUUCCUUAGUAAC |
| SEQ ID NO 205 | GAGAUGGCAGUUUCCUUAGUAACCA |
| SEQ ID NO 206 | AGAUGGCAGUUUCCUUAGUAACCAC |
| SEQ ID NO 207 | GAUGGCAGUUUCCUUAGUAACCACA |
| SEQ ID NO 208 | AUGGCAGUUUCCUUAGUAACCACAG |
| SEQ ID NO 209 | UGGCAGUUUCCUUAGUAACCACAGG |
| SEQ ID NO 210 | GGCAGUUUCCUUAGUAACCACAGGU |
| SEQ ID NO 211 | GCAGUUUCCUUAGUAACCACAGGUU |
| SEQ ID NO 212 | CAGUUUCCUUAGUAACCACAGGUUG |
| SEQ ID NO 213 | AGUUUCCUUAGUAACCACAGGUUGU |
| SEQ ID NO 214 | GUUUCCUUAGUAACCACAGGUUGUG |
| SEQ ID NO 215 | UUUCCUUAGUAACCACAGGUUGUGU |
| SEQ ID NO 216 | UUCCUUAGUAACCACAGGUUGUGUC |
| SEQ ID NO 217 | UCCUUAGUAACCACAGGUUGUGUCA |
| SEQ ID NO 218 | CCUUAGUAACCACAGGUUGUGUCAC |
| SEQ ID NO 219 | CUUAGUAACCACAGGUUGUGUCACC |
| SEQ ID NO 220 | UUAGUAACCACAGGUUGUGUCACCA |
| SEQ ID NO 221 | UAGUAACCACAGGUUGUGUCACCAG |
| SEQ ID NO 222 | AGUAACCACAGGUUGUGUCACCAGA |
| SEQ ID NO 223 | GUAACCACAGGUUGUGUCACCAGAG |
| SEQ ID NO 224 | UAACCACAGGUUGUGUCACCAGAGU |
| SEQ ID NO 225 | AACCACAGGUUGUGUCACCAGAGUA |
| SEQ ID NO 226 | ACCACAGGUUGUGUCACCAGAGUAA |
| SEQ ID NO 227 | CCACAGGUUGUGUCACCAGAGUAAC |

TABLE 4-continued oligonucleotides for skipping DMD Gene Exon 51

| | |
|---|---|
| SEQ ID NO 228 | CACAGGUUGUGUCACCAGAGUAACA |
| SEQ ID NO 229 | ACAGGUUGUGUCACCAGAGUAACAG |
| SEQ ID NO 230 | CAGGUUGUGUCACCAGAGUAACAGU |
| SEQ ID NO 231 | AGGUUGUGUCACCAGAGUAACAGUC |
| SEQ ID NO 232 | GGUUGUGUCACCAGAGUAACAGUCU |
| SEQ ID NO 233 | GUUGUGUCACCAGAGUAACAGUCUG |
| SEQ ID NO 234 | UUGUGUCACCAGAGUAACAGUCUGA |
| SEQ ID NO 235 | UGUGUCACCAGAGUAACAGUCUGAG |
| SEQ ID NO 236 | GUGUCACCAGAGUAACAGUCUGAGU |
| SEQ ID NO 237 | UGUCACCAGAGUAACAGUCUGAGUA |
| SEQ ID NO 238 | GUCACCAGAGUAACAGUCUGAGUAG |
| SEQ ID NO 239 | UCACCAGAGUAACAGUCUGAGUAGG |
| SEQ ID NO 240 | CACCAGAGUAACAGUCUGAGUAGGA |
| SEQ ID NO 241 | ACCAGAGUAACAGUCUGAGUAGGAG |

TABLE 5 oligonucleotides for skipping DMD Gene Exon 52

| | |
|---|---|
| SEQ ID NO 242 | AGCCUCUUGAUUGCUGGUCUUGUUU |
| SEQ ID NO 243 | GCCUCUUGAUUGCUGGUCUUGUUUU |
| SEQ ID NO 244 | CCUCUUGAUUGCUGGUCUUGUUUUU |
| SEQ ID NO 245 | CCUCUUGAUUGCUGGUCUUG |
| SEQ ID NO 246 PS232 | CUCUUGAUUGCUGGUCUUGUUUUUC |
| SEQ ID NO 247 | UCUUGAUUGCUGGUCUUGUUUUUCA |
| SEQ ID NO 248 | CUUGAUUGCUGGUCUUGUUUUUCAA |
| SEQ ID NO 249 | UUGAUUGCUGGUCUUGUUUUUCAAA |
| SEQ ID NO 250 | UGAUUGCUGGUCUUGUUUUUCAAAU |
| SEQ ID NO 251 | GAUUGCUGGUCUUGUUUUUCAAAUU |
| SEQ ID NO 252 | GAUUGCUGGUCUUGUUUUUC |
| SEQ ID NO 253 | AUUGCUGGUCUUGUUUUUCAAAUUU |
| SEQ ID NO 254 | UUGCUGGUCUUGUUUUUCAAAUUUU |
| SEQ ID NO 255 | UGCUGGUCUUGUUUUUCAAAUUUUG |
| SEQ ID NO 256 | GCUGGUCUUGUUUUUCAAAUUUUGG |
| SEQ ID NO 257 | CUGGUCUUGUUUUUCAAAUUUUGGG |
| SEQ ID NO 258 | UGGUCUUGUUUUUCAAAUUUUGGGC |
| SEQ ID NO 259 | GGUCUUGUUUUUCAAAUUUUGGGCA |
| SEQ ID NO 260 | GUCUUGUUUUUCAAAUUUUGGGCAG |
| SEQ ID NO 261 | UCUUGUUUUUCAAAUUUUGGGCAGC |
| SEQ ID NO 262 | CUUGUUUUUCAAAUUUUGGGCAGCG |

TABLE 5-continued oligonucleotides for skipping DMD Gene Exon 52

| | |
|---|---|
| SEQ ID NO 263 | UUGUUUUCAAAUUUUGGGCAGCGG |
| SEQ ID NO 264 | UGUUUUCAAAUUUUGGGCAGCGGU |
| SEQ ID NO 265 | GUUUUCAAAUUUUGGGCAGCGGUA |
| SEQ ID NO 266 | UUUUCAAAUUUUGGGCAGCGGUAA |
| SEQ ID NO 267 | UUUCAAAUUUUGGGCAGCGGUAAU |
| SEQ ID NO 268 | UUCAAAUUUUGGGCAGCGGUAAUG |
| SEQ ID NO 269 | UCAAAUUUUGGGCAGCGGUAAUGA |
| SEQ ID NO 270 | CAAAUUUUGGGCAGCGGUAAUGAG |
| SEQ ID NO 271 | AAAUUUUGGGCAGCGGUAAUGAGU |
| SEQ ID NO 272 | AAUUUUGGGCAGCGGUAAUGAGUU |
| SEQ ID NO 273 | AUUUUGGGCAGCGGUAAUGAGUUC |
| SEQ ID NO 274 | UUUUGGGCAGCGGUAAUGAGUUCU |
| SEQ ID NO 275 | UUUGGGCAGCGGUAAUGAGUUCUU |
| SEQ ID NO 276 | UUGGGCAGCGGUAAUGAGUUCUUC |
| SEQ ID NO 277 | UGGGCAGCGGUAAUGAGUUCUUCC |
| SEQ ID NO 278 | GGGCAGCGGUAAUGAGUUCUUCCA |
| SEQ ID NO 279 | GGCAGCGGUAAUGAGUUCUUCCAA |
| SEQ ID NO 280 | GCAGCGGUAAUGAGUUCUUCCAAC |
| SEQ ID NO 281 | CAGCGGUAAUGAGUUCUUCCAACU |
| SEQ ID NO 282 | AGCGGUAAUGAGUUCUUCCAACUG |
| SEQ ID NO 283 | GCGGUAAUGAGUUCUUCCAACUGG |
| SEQ ID NO 284 | CGGUAAUGAGUUCUUCCAACUGGG |
| SEQ ID NO 285 | GGUAAUGAGUUCUUCCAACUGGGG |
| SEQ ID NO 286 | GUAAUGAGUUCUUCCAACUGGGGA |
| SEQ ID NO 287 | GGUAAUGAGUUCUUCCAACUGG |
| SEQ ID NO 288 | GUAAUGAGUUCUUCCAACUGGGAC |
| SEQ ID NO 289 | UAAUGAGUUCUUCCAACUGGGGACG |
| SEQ ID NO 290 | AAUGAGUUCUUCCAACUGGGGACGC |
| SEQ ID NO 291 | AUGAGUUCUUCCAACUGGGGACGCC |
| SEQ ID NO 292 | UGAGUUCUUCCAACUGGGGACGCCU |
| SEQ ID NO 293 | GAGUUCUUCCAACUGGGGACGCCUC |
| SEQ ID NO 294 | AGUUCUUCCAACUGGGGACGCCUCU |
| SEQ ID NO 295 | GUUCUUCCAACUGGGGACGCCUCUG |
| SEQ ID NO 296 | UUCUUCCAACUGGGGACGCCUCUGU |
| SEQ ID NO 297 | UCUUCCAACUGGGGACGCCUCUGUU |
| SEQ ID NO 298 | CUUCCAACUGGGGACGCCUCUGUUC |
| SEQ ID NO 299 PS236 | UUCCAACUGGGGACGCCUCUGUUCC |
| SEQ ID NO 300 | UCCAACUGGGGACGCCUCUGUUCCA |
| SEQ ID NO 301 | CCAACUGGGGACGCCUCUGUUCCAA |
| SEQ ID NO 302 | CAACUGGGGACGCCUCUGUUCCAAA |
| SEQ ID NO 303 | AACUGGGGACGCCUCUGUUCCAAAU |
| SEQ ID NO 304 | ACUGGGGACGCCUCUGUUCCAAAUC |
| SEQ ID NO 305 | CUGGGGACGCCUCUGUUCCAAAUCC |
| SEQ ID NO 306 | UGGGGACGCCUCUGUUCCAAAUCCU |
| SEQ ID NO 307 | GGGGACGCCUCUGUUCCAAAUCCUG |
| SEQ ID NO 308 | GGGACGCCUCUGUUCCAAAUCCUGC |
| SEQ ID NO 309 | GGACGCCUCUGUUCCAAAUCCUGCA |
| SEQ ID NO 310 | GACGCCUCUGUUCCAAAUCCUGCAU |

TABLE 6 oligonucleotides for skipping DMD Gene Exon 53

| | |
|---|---|
| SEQ ID NO 311 | CUCUGGCCUGUCCUAAGACCUGCUC |
| SEQ ID NO 312 | UCUGGCCUGUCCUAAGACCUGCUCA |
| SEQ ID NO 313 | CUGGCCUGUCCUAAGACCUGCUCAG |
| SEQ ID NO 314 | UGGCCUGUCCUAAGACCUGCUCAGC |
| SEQ ID NO 315 | GGCCUGUCCUAAGACCUGCUCAGCU |
| SEQ ID NO 316 | GCCUGUCCUAAGACCUGCUCAGCUU |
| SEQ ID NO 317 | CCUGUCCUAAGACCUGCUCAGCUUC |
| SEQ ID NO 318 | CUGUCCUAAGACCUGCUCAGCUUCU |
| SEQ ID NO 319 | UGUCCUAAGACCUGCUCAGCUUCUU |
| SEQ ID NO 320 | GUCCUAAGACCUGCUCAGCUUCUUC |
| SEQ ID NO 321 | UCCUAAGACCUGCUCAGCUUCUUCC |
| SEQ ID NO 322 | CCUAAGACCUGCUCAGCUUCUUCCU |
| SEQ ID NO 323 | CUAAGACCUGCUCAGCUUCUUCCUU |
| SEQ ID NO 324 | UAAGACCUGCUCAGCUUCUUCCUUA |
| SEQ ID NO 325 | AAGACCUGCUCAGCUUCUUCCUUAG |
| SEQ ID NO 326 | AGACCUGCUCAGCUUCUUCCUUAGC |
| SEQ ID NO 327 | GACCUGCUCAGCUUCUUCCUUAGCU |
| SEQ ID NO 328 | ACCUGCUCAGCUUCUUCCUUAGCUU |
| SEQ ID NO 329 | CCUGCUCAGCUUCUUCCUUAGCUUC |
| SEQ ID NO 330 | CUGCUCAGCUUCUUCCUUAGCUUCC |
| SEQ ID NO 331 | UGCUCAGCUUCUUCCUUAGCUUCCA |
| SEQ ID NO 332 | GCUCAGCUUCUUCCUUAGCUUCCAG |
| SEQ ID NO 333 | CUCAGCUUCUUCCUUAGCUUCCAGC |
| SEQ ID NO 334 | UCAGCUUCUUCCUUAGCUUCCAGCC |
| SEQ ID NO 335 | CAGCUUCUUCCUUAGCUUCCAGCCA |
| SEQ ID NO 336 | AGCUUCUUCCUUAGCUUCCAGCCAU |
| SEQ ID NO 337 | GCUUCUUCCUUAGCUUCCAGCCAUU |

TABLE 6-continued oligonucleotides for skipping DMD Gene Exon 53

| | |
|---|---|
| SEQ ID NO 338 | CUUCUUCCUUAGCUUCCAGCCAUUG |
| SEQ ID NO 339 | UUCUUCCUUAGCUUCCAGCCAUUGU |
| SEQ ID NO 340 | UCUUCCUUAGCUUCCAGCCAUUGUG |
| SEQ ID NO 341 | CUUCCUUAGCUUCCAGCCAUUGUGU |
| SEQ ID NO 342 | UUCCUUAGCUUCCAGCCAUUGUGUU |
| SEQ ID NO 343 | UCCUUAGCUUCCAGCCAUUGUGUUG |
| SEQ ID NO 344 | CCUUAGCUUCCAGCCAUUGUGUUGA |
| SEQ ID NO 345 | CUUAGCUUCCAGCCAUUGUGUUGAA |
| SEQ ID NO 346 | UUAGCUUCCAGCCAUUGUGUUGAAU |
| SEQ ID NO 347 | UAGCUUCCAGCCAUUGUGUUGAAUC |
| SEQ ID NO 348 | AGCUUCCAGCCAUUGUGUUGAAUCC |
| SEQ ID NO 349 | GCUUCCAGCCAUUGUGUUGAAUCCU |
| SEQ ID NO 350 | CUUCCAGCCAUUGUGUUGAAUCCUU |
| SEQ ID NO 351 | UUCCAGCCAUUGUGUUGAAUCCUUU |
| SEQ ID NO 352 | UCCAGCCAUUGUGUUGAAUCCUUUA |
| SEQ ID NO 353 | CCAGCCAUUGUGUUGAAUCCUUUAA |
| SEQ ID NO 354 | CAGCCAUUGUGUUGAAUCCUUUAAC |
| SEQ ID NO 355 | AGCCAUUGUGUUGAAUCCUUUAACA |
| SEQ ID NO 356 | GCCAUUGUGUUGAAUCCUUUAACAU |
| SEQ ID NO 357 | CCAUUGUGUUGAAUCCUUUAACAUU |
| SEQ ID NO 358 | CAUUGUGUUGAAUCCUUUAACAUUU |

TABLE 7 oligonucleotides for skipping other exons of the DMD gene as identified

DMD Gene Exon 6

| | |
|---|---|
| SEQ ID NO 359 | CAUUUUUGACCUACAUGUGG |
| SEQ ID NO 360 | UUUGACCUACAUGUGGAAAG |
| SEQ ID NO 361 | UACAUUUUUGACCUACAUGUGGAAAG |
| SEQ ID NO 362 | GGUCUCCUUACCUAUGA |
| SEQ ID NO 363 | UCUUACCUAUGACUAUGGAUGAGA |
| SEQ ID NO 364 | AUUUUUGACCUACAUGGGAAAG |
| SEQ ID NO 365 | UACGAGUUGAUUGUCGGACCCAG |
| SEQ ID NO 366 | GUGGUCUCCUUACCUAUGACUGUGG |
| SEQ ID NO 367 | UGUCUCAGUAAUCUUCUUACCUAU |

DMD Gene Exon 7

| | |
|---|---|
| SEQ ID NO 368 | UGCAUGUUCCAGUCGUUGUGUGG |
| SEQ ID NO 369 | CACUAUUCCAGUCAAAUAGGUCUGG |

TABLE 7-continued oligonucleotides for skipping other exons of the DMD gene as identified

| | |
|---|---|
| SEQ ID NO 370 | AUUUACCAACCUUCAGGAUCGAGUA |
| SEQ ID NO 371 | GGCCUAAAACACAUACACAUA |

DMD Gene Exon 11

| | |
|---|---|
| SEQ ID NO 372 | CCCUGAGGCAUUCCCAUCUUGAAU |
| SEQ ID NO 373 | AGGACUUACUUGCUUUGUUU |
| SEQ ID NO 374 | CUUGAAUUUAGGAGAUUCAUCUG |
| SEQ ID NO 375 | CAUCUUCUGAUAAUUUUCCUGUU |

DMD Gene Exon 17

| | |
|---|---|
| SEQ ID NO 376 | CCAUUACAGUUGUCUGUGUU |
| SEQ ID NO 377 | UGACAGCCUGUGAAAUCUGUGAG |
| SEQ ID NO 378 | UAAUCUGCCUCUUCUUUUGG |

DMD Gene Exon 19

| | |
|---|---|
| SEQ ID NO 379 | CAGCAGUAGUUGUCAUCUGC |
| SEQ ID NO 380 | GCCUGAGCUGAUCUGCUGGCAUCUUGC |
| SEQ ID NO 381 | GCCUGAGCUGAUCUGCUGGCAUCUUGCAGUU |
| SEQ ID NO 382 | UCUGCUGGCAUCUUGC |

DMD Gene Exon 21

| | |
|---|---|
| SEQ ID NO 383 | GCCGGUUGACUUCAUCCUGUGC |
| SEQ ID NO 384 | GUCUGCAUCCAGGAACAUGGGUC |
| SEQ ID NO 385 | UACUUACUGUCUGUAGCUCUUUCU |
| SEQ ID NO 386 | CUGCAUCCAGGAACAUGGGUCC |
| SEQ ID NO 387 | GUUGAAGAUCUGAUAGCCGGUUGA |

DMD Gene Exon 44

| | |
|---|---|
| SEQ ID NO 388 | UCAGCUUCUGUUAGCCACUG |
| SEQ ID NO 389 | UUCAGCUUCUGUUAGCCACU |
| SEQ ID NO 390 | UUCAGCUUCUGUUAGCCACUG |
| SEQ ID NO 391 | UCAGCUUCUGUUAGCCACUGA |
| SEQ ID NO 392 | UUCAGCUUCUGUUAGCCACUGA |
| SEQ ID NO 393 | UCAGCUUCUGUUAGCCACUGA |
| SEQ ID NO 394 | UUCAGCUUCUGUUAGCCACUGA |
| SEQ ID NO 395 | UCAGCUUCUGUUAGCCACUGAU |
| SEQ ID NO 396 | UUCAGCUUCUGUUAGCCACUGAU |
| SEQ ID NO 397 | UCAGCUUCUGUUAGCCACUGAUU |
| SEQ ID NO 398 | UUCAGCUUCUGUUAGCCACUGAUU |
| SEQ ID NO 399 | UCAGCUUCUGUUAGCCACUGAUUA |
| SEQ ID NO 400 | UUCAGCUUCUGUUAGCCACUGAUA |
| SEQ ID NO 401 | UCAGCUUCUGUUAGCCACUGAUUAA |
| SEQ ID NO 402 | UUCAGCUUCUGUUAGCCACUGAUUAA |
| SEQ ID NO 403 | UCAGCUUCUGUUAGCCACUGAUUAAA |

TABLE 7-continued oligonucleotides for skipping other exons of the DMD gene as identified

| SEQ ID NO | Sequence |
|---|---|
| SEQ ID NO 404 | UUCAGCUUCUGUUAGCCACUGAUUAAA |
| SEQ ID NO 405 | CAGCUUCUGUUAGCCACUG |
| SEQ ID NO 406 | CAGCUUCUGUUAGCCACUGAU |
| SEQ ID NO 407 | AGCUUCUGUUAGCCACUGAUU |
| SEQ ID NO 408 | CAGCUUCUGUUAGCCACUGAUU |
| SEQ ID NO 409 | AGCUUCUGUUAGCCACUGAUUA |
| SEQ ID NO 410 | CAGCUUCUGUUAGCCACUGAUUA |
| SEQ ID NO 411 | AGCUUCUGUUAGCCACUGAUUAA |
| SEQ ID NO 412 | CAGCUUCUGUUAGCCACUGAUUAA |
| SEQ ID NO 413 | AGCUUCUGUUAGCCACUGAUUAAA |
| SEQ ID NO 414 | CAGCUUCUGUUAGCCACUGAUUAAA |
| SEQ ID NO 415 | AGCUUCUGUUAGCCACUGAUUAAA |
| SEQ ID NO 416 | AGCUUCUGUUAGCCACUGAU |
| SEQ ID NO 417 | GCUUCUGUUAGCCACUGAUU |
| SEQ ID NO 418 | AGCUUCUGUUAGCCACUGAUU |
| SEQ ID NO 419 | GCUUCUGUUAGCCACUGAUUA |
| SEQ ID NO 420 | AGCUUCUGUUAGCCACUGAUUA |
| SEQ ID NO 421 | GCUUCUGUUAGCCACUGAUUAA |
| SEQ ID NO 422 | AGCUUCUGUUAGCCACUGAUUAA |
| SEQ ID NO 423 | GCUUCUGUUAGCCACUGAUUAAA |
| SEQ ID NO 424 | AGCUUCUGUUAGCCACUGAUUAAA |
| SEQ ID NO 425 | GCUUCUGUUAGCCACUGAUUAAA |
| SEQ ID NO 426 | CCAUUUGUAUUUAGCAUGUUCCC |
| SEQ ID NO 427 | AGAUACCAUUUGUAUUUAGC |
| SEQ ID NO 428 | GCCAUUUCUCAACAGAUCU |
| SEQ ID NO 429 | GCCAUUUCUCAACAGAUCUGUCA |
| SEQ ID NO 430 | AUUCUCAGGAAUUUGUGUCUUUC |
| SEQ ID NO 431 | UCUCAGGAAUUUGUGUCUUUC |
| SEQ ID NO 432 | GUUCAGCUUCUGUUAGCC |
| SEQ ID NO 433 | CUGAUUAAAUAUCUUUAUAU C |
| SEQ ID NO 434 | GCCGCCAUUUCUCAACAG |
| SEQ ID NO 435 | GUAUUUAGCAUGUUCCCA |
| SEQ ID NO 436 | CAGGAAUUUGUGUCUUUC |

DMD Gene Exon 45

| SEQ ID NO | Sequence |
|---|---|
| SEQ ID NO 437 | UUUGCCGCUGCCCAAUGCCAUCCUG |
| SEQ ID NO 438 | AUUCAAUGUUCUGACAACAGUUUGC |
| SEQ ID NO 439 | CCAGUUGCAUUCAAUGUUCUGACAA |
| SEQ ID NO 440 | CAGUUGCAUUCAAUGUUCUGAC |
| SEQ ID NO 441 | AGUUGCAUUCAAUGUUCUGA |
| SEQ ID NO 442 | GAUUGCUGAAUUAUUUCUUCC |
| SEQ ID NO 443 | GAUUGCUGAAUUAUUUCUUCCCCAG |
| SEQ ID NO 444 | AUUGCUGAAUUAUUUCUUCCCCAGU |
| SEQ ID NO 445 | UUGCUGAAUUAUUUCUUCCCCAGUU |
| SEQ ID NO 446 | UGCUGAAUUAUUUCUUCCCCAGUUG |
| SEQ ID NO 447 | GCUGAAUUAUUUCUUCCCCAGUUGC |
| SEQ ID NO 448 | CUGAAUUAUUUCUUCCCCAGUUGCA |
| SEQ ID NO 449 | UGAAUUAUUUCUUCCCCAGUUGCAU |
| SEQ ID NO 450 | GAAUUAUUUCUUCCCCAGUUGCAUU |
| SEQ ID NO 451 | AAUUAUUUCUUCCCCAGUUGCAUUC |
| SEQ ID NO 452 | AUUAUUUCUUCCCCAGUUGCAUUCA |
| SEQ ID NO 453 | UUAUUUCUUCCCCAGUUGCAUUCAA |
| SEQ ID NO 454 | UAUUUCUUCCCCAGUUGCAUUCAAU |
| SEQ ID NO 455 | AUUUCUUCCCCAGUUGCAUUCAAUG |
| SEQ ID NO 456 | UUUCUUCCCCAGUUGCAUUCAAUGU |
| SEQ ID NO 457 | UUCUUCCCCAGUUGCAUUCAAUGUU |
| SEQ ID NO 458 | UCUUCCCCAGUUGCAUUCAAUGUUC |
| SEQ ID NO 459 | CUUCCCCAGUUGCAUUCAAUGUUCU |
| SEQ ID NO 460 | UUCCCCAGUUGCAUUCAAUGUUCUG |
| SEQ ID NO 461 | UCCCCAGUUGCAUUCAAUGUUCUGA |
| SEQ ID NO 462 | CCCCAGUUGCAUUCAAUGUUCUGAC |
| SEQ ID NO 463 | CCCAGUUGCAUUCAAUGUUCUGACA |
| SEQ ID NO 464 | CCAGUUGCAUUCAAUGUUCUGACAA |
| SEQ ID NO 465 | CAGUUGCAUUCAAUGUUCUGACAAC |
| SEQ ID NO 466 | AGUUGCAUUCAAUGUUCUGACAACA |
| SEQ ID NO 467 | UCC UGU AGA AUA CUG GCA UC |
| SEQ ID NO 468 | UGCAGACCUCCUGCCACCGCAGAUUCA |
| SEQ ID NO 469 | UUGCAGACCUCCUGCCACCGCAGAUUCAGGCUUC |
| SEQ ID NO 470 | GUUGCAUUCAAUGUUCUGACAACAG |
| SEQ ID NO 471 | UUGCAUUCAAUGUUCUGACAACAGU |
| SEQ ID NO 472 | UGCAUUCAAUGUUCUGACAACAGUU |
| SEQ ID NO 473 | GCAUUCAAUGUUCUGACAACAGUUU |
| SEQ ID NO 474 | CAUUCAAUGUUCUGACAACAGUUUG |
| SEQ ID NO 475 | AUUCAAUGUUCUGACAACAGUUUGC |
| SEQ ID NO 476 | UCAAUGUUCUGACAACAGUUUGCCG |
| SEQ ID NO 477 | CAAUGUUCUGACAACAGUUUGCCGC |
| SEQ ID NO 478 | AAUGUUCUGACAACAGUUUGCCGCU |
| SEQ ID NO 479 | AUGUUCUGACAACAGUUUGCCGCUG |
| SEQ ID NO 480 | UGUUCUGACAACAGUUUGCCGCUGC |

TABLE 7-continued oligonucleotides for skipping other exons of the DMD gene as identified

| | |
|---|---|
| SEQ ID NO 481 | GUUCUGACAACAGUUUGCCGCUGCC |
| SEQ ID NO 482 | UUCUGACAACAGUUUGCCGCUGCCC |
| SEQ ID NO 483 | UCUGACAACAGUUUGCCGCUGCCCA |
| SEQ ID NO 484 | CUGACAACAGUUUGCCGCUGCCCAA |
| SEQ ID NO 485 | UGACAACAGUUUGCCGCUGCCCAAU |
| SEQ ID NO 486 | GACAACAGUUUGCCGCUGCCCAAUG |
| SEQ ID NO 487 | ACAACAGUUUGCCGCUGCCCAAUGC |
| SEQ ID NO 488 | CAACAGUUUGCCGCUGCCCAAUGCC |
| SEQ ID NO 489 | AACAGUUUGCCGCUGCCCAAUGCCA |
| SEQ ID NO 490 | ACAGUUUGCCGCUGCCCAAUGCCAU |
| SEQ ID NO 491 | CAGUUUGCCGCUGCCCAAUGCCAUC |
| SEQ ID NO 492 | AGUUUGCCGCUGCCCAAUGCCAUCC |
| SEQ ID NO 493 | GUUUGCCGCUGCCCAAUGCCAUCCU |
| SEQ ID NO 494 | UUUGCCGCUGCCCAAUGCCAUCCUG |
| SEQ ID NO 495 | UUGCCGCUGCCCAAUGCCAUCCUGG |
| SEQ ID NO 496 | UGCCGCUGCCCAAUGCCAUCCUGGA |
| SEQ ID NO 497 | GCCGCUGCCCAAUGCCAUCCUGGAG |
| SEQ ID NO 498 | CCGCUGCCCAAUGCCAUCCUGGAGU |
| SEQ ID NO 499 | CGCUGCCCAAUGCCAUCCUGGAGUU |
| SEQ ID NO 500 | UGUUUUUGAGGAUUGCUGAA |
| SEQ ID NO 501 | UGUUCUGACAACAGUUUGCCGCUGCCCAAUGCCAUCCUGG |
| DMD Gene Exon 55 | |
| SEQ ID NO 502 | CUGUUGCAGUAAUCUAUGAG |
| SEQ ID NO 503 | UGCAGUAAUCUAUGAGUUUC |
| SEQ ID NO 504 | GAGUCUUCUAGGAGCCUU |
| SEQ ID NO 505 | UGCCAUUGUUUCAUCAGCUCUUU |
| SEQ ID NO 506 | UCCUGUAGGACAUUGGCAGU |
| SEQ ID NO 507 | CUUGGAGUCUUCUAGGAGCC |
| DMD Gene Exon 57 | |
| SEQ ID NO 508 | UAGGUGCCUGCCGGCUU |
| SEQ ID NO 509 | UUCAGCUGUAGCCACACC |
| SEQ ID NO 510 | CUGAACUGCUGGAAAGUCGCC |
| SEQ ID NO 511 | CUGGCUUCCAAAUGGGACCUGAAAAGAAC |
| DMD Gene Exon 59 | |
| SEQ ID NO 512 | CAAUUUUUCCCACUCAGUAUU |
| SEQ ID NO 513 | UUGAAGUUCCUGGAGUCUU |
| SEQ ID NO 514 | UCCUCAGGAGGCAGCUCUAAAU |
| DMD Gene Exon 62 | |
| SEQ ID NO 515 | UGGCUCUCUCCCAGGG |
| SEQ ID NO 516 | GAGAUGGCUCUCUCCCAGGGACCUGG |
| SEQ ID NO 517 | GGGCACUUUGUUUGGCG |
| DMD Gene Exon 63 | |
| SEQ ID NO 518 | GGUCCCAGCAAGUUGUUUG |
| SEQ ID NO 519 | UGGGAUGGUCCCAGCAAGUUGUUUG |
| SEQ ID NO 520 | GUAGAGCUCUGUCAUUUUGGG |
| DMD Gene Exon 65 | |
| SEQ ID NO 521 | GCUCAAGAGAUCCACUGCAAAAAAC |
| SEQ ID NO 522 | GCCAUACGUACGUAUCAUAAACAUUC |
| SEQ ID NO 523 | UCUGCAGGAUAUCCAUGGGCUGGUC |
| DMD Gene Exon 66 | |
| SEQ ID NO 524 | GAUCCUCCCUGUUCGUCCCCUAUUAUG |
| DMD Gene Exon 69 | |
| SEQ ID NO 525 | UGCUUUAGACUCCUGUACCUGAUA |
| DMD Gene Exon 75 | |
| SEQ ID NO 526 | GGCGGCCUUUGUGUUGAC |
| SEQ ID NO 527 | GGACAGGCCUUUAUGUUCGUGCUGC |
| SEQ ID NO 528 | CCUUUAUGUUCGUGCUGCU |

The invention claimed is:

1. An isolated antisense oligonucleotide whose base sequence consists of the base sequence 5'-GGUAAUGAGUUCUUCCAACUGG-3' (SEQ ID NO: 287), said oligonucleotide comprising a modification.

2. The oligonucleotide of claim 1, wherein the modified-oligonucleotide comprises at least one nucleotide analogue, wherein the nucleotide analogue comprises a modified base and/or, a modified sugar moiety and/or a modified internucleoside linkage.

3. The oligonucleotide of claim 1, wherein the modified oligonucleotide comprises a modified internucleoside linkage.

4. The oligonucleotide of claim 2, wherein all the sugar moieties are modified.

5. The oligonucleotide of claim 2, wherein all the internucleoside linkages are modified.

6. The oligonucleotide of claim 2 or 4, wherein the modified sugar moiety is mono- or di-substituted at the 2', 3' and/or 5' position.

7. The oligonucleotide of claim 6, wherein the modified sugar moiety is a 2'-O-methyl ribose.

8. The oligonucleotide of claim 3, wherein the modified backbone is a morpholino backbone.

9. The oligonucleotide of claim 2 or 4, comprising a 2'-O-substituted phosphorothioate moiety.

10. The oligonucleotide of claim 3 or 5, wherein the modified internucleoside linkage is a phosphorothioate linkage.

11. The oligonucleotide of claim 1, wherein all sugar moieties are 2'-O-methyl substituted ribose moieties and all internucleoside linkages are phosphorothioate moieties.

12. The oligonucleotide according to claim 3, comprising: a morpholino backbone, a carbamate backbone, a siloxane backbone, a sulfide backbone, a sulfoxide backbone, a sulfone backbone, a formacetyl backbone, a thioformacetyl backbone, a methyleneformacetyl backbone, a riboacetyl backbone, an alkene containing backbone, a sulfamate backbone, a sulfonate backbone, a sulfonamide backbone, a methyleneimino backbone, a methylenehydrazino backbone and/or an amide backbone.

13. The oligonucleotide of claim 3, wherein the oligonucleotide comprises a morpholine ring and/or a phosphorodiamidate internucleoside linkage and/or a peptide nucleic acid, and/or a locked nucleic acid.

14. The oligonucleotide of claim 1, comprising a phosphorothioate internucleoside linkage, and wherein a sugar moiety is 2'-O-methyl substituted.

15. The oligonucleotide of claim 1, which is a phosphorodiamidate morpholino oligomer (PMO).

16. The oligonucleotide of claim 2, wherein said oligonucleotide comprises a modified base.

17. The oligonucleotide of claim 1, said oligonucleotide comprising a locked nucleic acid (LNA).

* * * * *